United States Patent [19]

Mueller et al.

[11] Patent Number: 6,051,610
[45] Date of Patent: Apr. 18, 2000

[54] COMPOUNDS ACTIVE AT A NOVEL SITE ON RECEPTOR-OPERATED CALCIUM CHANNELS USEFUL FOR TREATMENT OF NEUROLOGICAL DISORDERS AND DISEASES

[75] Inventors: Alan L. Mueller, Salt Lake City; Manuel F. Balandrin, Sandy; Bradford C. Van Wagenen, Salt Lake City; Eric G. DelMar, Salt Lake City; Scott T. Moe, Salt Lake City; Linda D. Artman, Salt Lake City; Robert M. Barmore, Salt Lake City, all of Utah

[73] Assignee: NPS Pharmaceuticals, Inc., Salt Lake City, Utah

[21] Appl. No.: 09/252,433

[22] Filed: Feb. 18, 1999

Related U.S. Application Data

[63] Continuation of application No. 08/485,038, Jun. 7, 1995, which is a continuation-in-part of application No. PCT/US94/12293, Oct. 26, 1994, which is a continuation-in-part of application No. 08/288,668, Aug. 9, 1994, abandoned, which is a continuation-in-part of application No. 08/194,210, Feb. 8, 1994, abandoned, which is a continuation-in-part of application No. 08/014,813, Feb. 8, 1993, abandoned.

[51] Int. Cl.⁷ ........................ A61K 31/135; C07C 211/35
[52] U.S. Cl. ............................................. 514/628; 564/315
[58] Field of Search ................................... 564/316, 319, 564/315; 514/648

[56] References Cited

U.S. PATENT DOCUMENTS

| | | | |
|---|---|---|---|
| 2,894,033 | 7/1959 | Janssen et al. | 260/567.6 |
| 3,238,242 | 3/1966 | Harsanyi et al. | 260/465 |
| 3,372,193 | 3/1968 | Moffett et al. | 260/566 |
| 4,018,895 | 4/1977 | Molloy et al. | 424/330 |
| 4,028,415 | 6/1977 | Clark | 260/570 |
| 4,313,896 | 2/1982 | Molloy et al. | 260/501.18 |
| 4,988,730 | 1/1991 | Korbonits et al. | 514/466 |
| 5,037,846 | 8/1991 | Saccomano et al. | 514/419 |
| 5,145,870 | 9/1992 | Jakobsen et al. | 514/524 |
| 5,185,369 | 2/1993 | Saccomano et al. | 514/502 |
| 5,310,756 | 5/1994 | Jakobsen et al. | 514/524 |
| 5,382,600 | 1/1995 | Jönsson et al. | 514/603 |

FOREIGN PATENT DOCUMENTS

| | | |
|---|---|---|
| 0 005 658 | 11/1979 | European Pat. Off. |
| 0 208 523 A2 | 1/1987 | European Pat. Off. |
| 0 399 504 A2 | 11/1990 | European Pat. Off. |
| 0 436 332 A2 | 7/1991 | European Pat. Off. |
| 1051281 | 7/1959 | Germany . |
| 33285 | 12/1964 | Germany . |
| 1 793 735 | 7/1973 | Germany . |
| 42 39 816 A1 | 6/1994 | Germany . |
| 300541 | 6/1964 | Netherlands . |
| 1169944 | 7/1967 | United Kingdom . |
| 1134715 | 11/1968 | United Kingdom . |
| 1135926 | 12/1968 | United Kingdom . |
| 92/14709 | 3/1992 | WIPO . |
| 93/04036 | 3/1993 | WIPO . |
| 93/04041 | 3/1993 | WIPO . |
| 93/04373 | 3/1993 | WIPO . |
| 95/21612 | 8/1995 | WIPO . |
| 96/05818 | 2/1996 | WIPO . |
| 96/40097 | 12/1996 | WIPO . |

OTHER PUBLICATIONS

Akaike et al., "Spider Toxin Blocks Excitatory Amino Acid Responses in Isolated Hippocampal Pyramidal Neurons," *Neuroscience Letters* 79:326–330 (1987).

Anis et al., "Structure–Activity Relationships of Philanthotoxin Analogs and Polyamines on N–Methyl–D–Aspartate and Nicotinic Acetylcholine Receptors," *Journal of Pharmacology and Experimental Therapeutics* 254:764–773 (1990).

Artman et al., "Preferential Inhibitory Effects of Arylamine Spider Toxins on NMDA Receptor–Mediated Increases in Cytosolic Calcium," *Society for Neuroscience Abstracts* 17(Part 1):394 at abstract No. 163.19 (1991).

Ashe et al., "Argiotoxin–636 Blocks Excitatory Synaptic Transmission in Rat Hippocampal CA1 Pyramidal Neurons," *Brain Research* 480:234–240 (1989).

Beckett and Casy, "Configurational Studies in Synthetic Analgesics," *J. Chem. Soc.* pp. 900–904 (1955).

Blagbrough and Usherwood, "Polyamine amide toxins as pharmacological tools and pharmaceutical agents," *Proceedings of the Royal Society of Edinburgh* 99B(1–2):67–81 (1992).

Blagbrough et al., "Arthropod Toxins as Leads for Novel Insecticides: An Assessment of Polyamine Amides as Glutamate Antagonists," *Toxicon* 30:303–322 (1992).

Blake et al., "2–Methyl–3,3–Diphenyl–3–Propanolamine (2–MDP) Selectively Antagonises N–Methyl–Aspartate (NMA)," *Pharmacology Biochemistry & Behavior* 24:23–25 (1986).

Blaschke et al., "A Single Amino Acid Determines the Subunit–Specific Spider Toxin Block of Amino–3–Hydroxy–5–Methylisoxazole–4–Propionate/ Kainate Receptor Channels," *Proc. Natl. Acad. Sci. USA* 90:6528–6532 (1993).

Brackley et al., "Selective Antagonism of Native and Cloned Kainate and NMDA Receptors by Polyamine–Containing Toxins," *Journal of Pharmacology and Experimental Therapeutics* 266:1573–1580 (1993).

Bruce et al., "Structure–Activity Relationships of Analogues of The WASP Toxin Philanthotoxin: Non–Competetive Antagonists of Quisqualate Receptors," *Toxicon* 28(11):1333–1346 (1990).

(List continued on next page.)

*Primary Examiner*—Richard L. Raymond
*Attorney, Agent, or Firm*—Lyon & Lyon LLP

[57] ABSTRACT

Method and compositions for treating a patient having a neurological disease or disorder, such as stroke, head trauma, spinal cord injury, epilepsy, anxiety, or neurodegenerative diseases such as Alzheimer's Disease, Huntington's Disease, Parkinson's Disease, or amyotrophic lateral sclerosis (ALS).

24 Claims, No Drawings

OTHER PUBLICATIONS

Burtsev and Savkov, "Calcium Antagonists (Finoptin and Senzit) in the Treatment of Cerebrovascular Disorders," *Klinicheskaia Meditsina* 67(9):51–54 (1989) (abstract from Medline).

Buschauer et al., "Synthesis and histamine $H_2$ agonistic activity of arpromidine analogues: replacement of the pheniramine–like moiety by non–heterocyclic groups," *Eur. J. Med. Chem.* 27:321–330 (1992).

Camps et al., "A New and Efficient One–Pot Preparation of Alkyl Halides From Alcohols," *Synthesis Communications* pp. 511–512 (May 1987).

*Chemical Abstracts* 5:423 (1911).

*Chemical Abstracts* 54:24555i (1960), 24555–24556.

*Chemical Abstracts* 54:424a (1960).

*Chemical Abstracts* 66:4375 (1967).

*Chemical Abstracts* 67:3059 (1967).

*Chemical Abstracts* 69:3322 (1968).

Chemical Abstracts Service, Registry Handbook Reg. No. 114272–62–7 through 116231–28–8, 1988 Supplement.

Choi et al., "Glutamate Neurotoxicity in Cortical Cell Culture," *J. Neuroscience* 7:357–368 (1987).

Choi et al., "Synthesis and Assay of Hybrid Analogs of Argiotoxin–636 and Philanthotoxin–433: Glutamate Receptor Antagonists," *Tetrahedron* 49:5777–5790 (1993).

Choi, "Glutamate Neurotoxicity and Diseases of the Nervous System," *Neuron* 1:623–634 (1988).

Collingridge and Davis, "Ch. 9—NMDA receptors and long–term potentiation in the hippocampus," in *The NMDA Receptor*, edited by Watkins and Collingridge, IRL Press, pp. 123–135 (1989).

Cramer et al., "Kainic Acid and 4–Aminopyridine Seizure Models in Mice: Evaluation of Efficacy of Anti–Epileptic Agents and Calcium Antagonists," *Life Sciences* 54:PL271–PL275 (1994).

Davies et al., "Polyamine Spider Toxins Are Potent Un–competitive Antagonists of Rat Cortex Excitatory Amino Acid Receptors," *European Journal of Pharmacology—Molecular Pharmacology Section* 227:51–56 (1992).

Deneris et al., "Pharmacological and Functional Diversity of Neuronal Nicotinic Acetylcholine Receptors," *TiPS* 12:34–40 (1991).

Dickenson, "A Cure for Wind–Up: NMDA Receptor Antagonists as Potential Analgesics," *TiPS* 11:307–309 (1990).

Dingledine et al., "Excitatory Amino Acid Receptors in Epilepsy," *TiPS* 11:334–338 (1990).

Donevan and Rogawski, "GYKI 52466, a 2,3–Benzodiazepine, is a Highly Selective, Noncompetitive Antagonist of AMPA/Kainate Receptor Responses," *Neuron* 10:51–59 (1993).

Donevan et al., "Arcaine Blocks N–Methyl–D–Aspartate Receptor Responses by an Open Channel Mechanism: Whole–Cell and Single–Channel Recording Studies in Cultured Hippocampal Neurons," *Molecular Pharmacology* 41:727–735 (1992).

Draguhn et al., "Argiotoxin$_{636}$ inhibits NMDA–activated ion channels expressed in Xenopus oocytes," *Neuroscience Letters* 132:187–190 (1991).

Fiedler et al., "66. Synthetische Analoga von niedermolekularen Spinnentoxinen mit Acyl–polyamin–Struktur," *Helvetica Chimica Acta* 76:1167–1181 (1993).

Fiedler et al., "98. Synthese von selektiv N–funktionalisierten Polyamin–Derivaten," *Helvetica Chimica Acta* 76:1511–1519 (1993).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Fisher and Bogousslavsky, "Evolving Toward Effective Therapy for Acute Ischemic Stroke," *JAMA* 270:360–364 (1993).

Foye et al., *Principals of Medicinal Chemistry*, 4th edition, Lea & Febiger/Williams and Wilkins, Philadelphia, PA, pp. 233, 265, 281–282, 340–341, 418–427 and 430 (1995).

Ginsberg and Busto, "Rodent Models of Cerebral Ischemia," *Stroke* 20:1627–1642 (1989).

Gisvold and Steen, "Drug Therapy in Brain Ischaemia," *Br. J. Anaesth.* 57:96–109 (1985).

Grishin et al., "Isolation and Structure Analysis of Components from Venom of the Spider *Argiope lobata*," *Toxicon* 27:451–549 (1989).

Gullak et al., "CNS Binding Sites of the Novel NMDA Antagonist Arg–636," *Soc. Neurosci. Abst.* 15:1168 at abstract No. 463.23 (1989).

Hayes et al., "Anticonvulsant Properties of Phencyclidine––Like Drugs in Mice," *European Journal of Pharmacology* 117:121–125 (1985).

Helke and Raines, "Antiextensor Effects of 3,3–Diphenyl––n–Propylamine in the Mouse," *European Journal of Pharmacology* 48:231–235 (1978).

Herlitze et al., "Argiotoxin Detects Molecular Differences in AMPA Receptor Channels," *Neuron* 10:1131–1140 (1993).

Herold and Yaksh, "Anesthesia and Muscle Relaxation with Intrathecal Injections of AR636 and AG489, Two Acylpolyamine Spider Toxins, in Rat," *Anesthesiology* 77:507–512 (1992).

Honore et al., "Quinoxalinediones: Potent Competitive Non––NMDA Glutamate Receptor Antagonists," *Science* 241:701–703 (1988).

Hughes, "Merz Novel Approach to the Treatment of Dementia," Script No. 1666:24–25 (1991).

Jackson and Parks, "Spider Toxins: Recent Applications In Neurobiology," *Ann. Rev. Neurosci.* 12:405–414 (1989).

Jackson and Usherwood, "Spider Toxins as Tools for Dissecting Elements of Excitatory Amino Acid Transmission," *TINS* 11:278–283 (1988).

Janssen et al., *Synthetic Analgesics: Part I—Diphenylpropylamines*, Pergamon Press, pp. 1–109 (1960).

Jasys et al., "Isolation, Structure Elucidation, and Synthesis of Novel Hydroxylamine–Containing Polyamines From the Venom of the *Agelenopsis aperta* Spider," *J. Amer. Chem. Soc.* 112:6696–6704 (1990).

Jasys et al., "The Total Synthesis of Argiotoxins 636, 659 and 673," *Tetrahedron Letters* 29:6223–6226 (1988).

Jones and Lodge, "Comparison of Some Arthropod Toxins and Toxin Fragments as Antagonists of Excitatory Amino Acid–Induced Excitation of Rat Spinal Neurones," *European Journal of Pharmacology* 204:203–209 (1991).

Jones et al., "Philanthotoxin Blocks Quisqualate–, AMPA– and Kainate–, but not NMDA–, Induced Excitation of Rat Brainstem Neurones in vivo," *Br. J. Pharmacol.* 101:968–970 (1990).

Jones et al., "Sutstituted 1,1–Diphenyl–3–aminoprop–l–enes and 1,1–Diphenyl–3–aminopropanes as Potential Antidepressant Agents," *J. Med. Chem.* 14(2):161–164 (1971).

Kalman et al., "Difenil–propil–amin–szarmazekok," *Magyar Kemiai Folyirat* 78:46–49 (1972).

Kanai et al., "An Analogue of Joro Spider Toxin Selectively Suppresses Hippocampal Epileptic Discharges Induced by Quisqualate," *Brain Research* 581:161–164 (1992).

Karpiak et al., "Animal Models for the Study of Drugs in Ischemic Stroke," *Annu. Rev. Pharmocol. Toxicol.* 29:403–414 (1989).

Kasuya, Yutaka, "Chemicopharmacological Studies on Antispasmodic Action. XII. Structure–Activity Relationship of Aralkylamines," *Chem. Pharm.* 6(2):147–154 (1958).

Kawai et al., "Effect of a Spider Toxin on Glutaminergic Synapses in the Mammalian Brain," *Biomedical Research* 3:353–355 (1982).

Kawai et al., "Spider Toxin and the Glutamate Receptors," *Comp. Biochem. Physiol.* 98C:87–95 (1991).

Kawai, "Neuroactive Toxins of Spider Venoms," *J. Toxicol.—Toxin Reviews* 10:131–167 (1991).

Keasling and Moffett, "Central Nervous System Agents. 3. Structure–Activity Relationship of a Series of Diphenylaminopropanols," *Journal of Medicinal Chemistry* 14(11):1106–1111 (1971).

Kiskin et al., "A Highly Potent and Selective N–Methyl-–D–Aspartate Receptor Antagonist From the Venom of the *Agelenopsis aperta* Spider," *Neuroscience* 51:11–18 (1992).

Kiskin et al., "Argiopine, Argiopinines and Pseudoargiopinines as Glutamate Receptor Blockers in Hippocampal Neurons," *Neurophysiology* 21:748–754 (1989) (in Russian).

Kovacs and Hesse, "Synthetic Analogues of Naturally Occurring Spider Toxins," *Helvetica Chimica Acta* 75:1909–1924 (1992).

Leszkovsky et al., "The Pharmacology of Diphenylalkyl Derivatives," *Acta Physiologica Academiae Scientiarum Hungaricae Tomus* 29(3–4):283–298 (1966).

Marcusson et al., "Inhibition of [$^3$H]paroxetine binding by various serotonin uptake inhibitors: structure–activity relationships," *Europ. J. Pharmacol.* 215:191–198 (1992).

Meldrum and Garthwaite, "Excitatory Amino Acid Neurotoxicity and Neurodegenerative Disease," *TiPS* 11:379–387 (1990).

Meldrum, "Excitatory Amino Acid Neurotransmission in Epilepsy and Anticonvulsant Therapy," in *Excitatory Amino Acids*, Meldrum et al. editors, New York, Raven Press, pp. 655–670 (1991).

Melloni et al., "Potential antidepressant agents. Aryloxy-–benzyl derivatives of ethanolamine and morpholine," *Eur. J. Med. Chem.—Chim. Ther.* 19:235–242 (1984).

*Merck Index*, 11th edition, Merck & Co., Inc., Rahway, New Jersey, p. 218 at No. 1433, p. 337 at No. 2180, p. 623 at No. 3916, p. 655 at No. 4112, p. 1148 at No. 7198, p. 1227 at No. 7744, p. 1444 at No. 9098, and p. 1597 at No. 10024 (1989).

Mikio et al., "Synthesis of Analgesics," *Chemical Abstracts* vol. 83, No. 7, Aug. 18, 1975 at abstract No. XP002016632.

Moffett et al., "Central Nervous System Agents. 1. Synthesis of Diphenyl–tert–aminopropanols," *J. Med. Chem.* 14(11):1088–1100 (1971).

Mueller et al., "Arylamine Spider Toxins Antagonize NMDA Receptor–Mediated Synaptic Transmission in Rat Hippocampal Slices," *Synapse* 9:244–250 (1991).

Mueller et al., "Effects of Polyamine Spider Toxins on NMDA Receptor–Mediated Transmission in Rat Hippocampus In Vitro," *Soc. Neurosci. Abst.* 15:945 at abstract No. 373.10 (1989).

Nakanishi et al., "Bioorganic Studies of Transmitter Receptors with Philanthotoxin Analogs," *Pure & Applied Chemistry* vol. 66, #3 (Mar. 1994).

Nakanishi, "Molecular Diversity of Glutamate Receptors and Implications for Brain Function," *Science* 258:597–603 (1992).

Nason et al., "Synthesis of Neurotoxic Nephila Spider Venoms: NSTX–3 and JSTX–3," *Tetrahedron Letters* 30:2337–2340 (1989).

Nemeth et al., "Arylamines Derived From Spider Venom Are Potent and Selective NMDA Receptor Antagonists in The Mammalian CNS," in *Neuroreceptors, Ion Channels and the Brain*, Kawai et al., editors, pp. 21–28 (1992).

Olney et al., "Pathological Changes Induced in Cerebrocortical Neurons by Phencyclidine and Related Drugs," *Science* 244:1360–1362 (1989).

Palmer et al., "Anticonvulsant Properties of Calcium Channel Blockers in Mice: N–Methyl–D–, L–Aspartate– and Bay K 8644–Induced Convulsions are Potentially Blocked by the Dihydropyridines," *Epilepsia* 34:372–380 (1993).

Parks et al., "Arylamine Toxins From Funnel–Web Spider (*Agelenopsis aperta*) Venom Antagonize N–Methyl–D–aspartate Receptor Function in Mammalian Brain," *J. Biol. Chem.* 266:21523–21529 (1991).

Parks et al., "Polyamine Spider Toxins Block NMDA Receptor—Mediated Increases in Cytosolic Calcium in Cerebellar Granule Neurons," *Soc. Neurosci. Abst.* 15:1169 at abstract No. 463.25 (1989).

Paul et al., "Adaptation of the N–Methyl–D–Aspartate Receptor Complex Following Chronic Antidepressant Treatments," *J. Pharmacology and Experimental Therapeutics* 269:95–102 (1994).

Peterson, "Studies on a New Spasmolytic Compound 1,1–diphenyl–3–dimethylaminobutene–1 (A29) related to Methadon, and on the Combined Use of this Compound and a Potent Analgesic Ketobemidone," *Acta Pharmacol. et toxciol.* 7:51–64 (1951).

Priestley et al., "Antagonism of responses to excitatory amino acids on rat cortical neurones by the spider toxin, argiotoxin$_{636}$," *Br. J. Pharmacol.* 97:1315–1323 (1989).

Prous, *The Year's Drug News, Therapeutic Targets*, 1995 Edition, Prous Science Publishers, Barcelona, Spain, pp. 13, 55–56, 58–59, 74, 89, 144–145, 152, 296–297 and 317 (1995).

Quistad et al., "Paralytic and Insecticidal Toxins from the Funnel Web Spider, *Hololena curta*," *Toxicon* 29:329–336 (1991).

Raditsch et al., "Subunit–Specific Block of Cloned NMDA Receptors by Argiotoxin$_{636}$," *FEBS Letters* 324(1):63–66 (1993).

Ransom and Stec, "Cooperative Modulation of [$^3$H] MK–801 Binding to the N–Methyl–D–Aspartate Receptor–Ion Channel Complex by L–Glutamate, Glycine and Polyamines," *Journal of Neurochemistry* 51:830–836 (1988).

Reist et al., "Sodium Azide in Dimethylformamide for the Preparation of Amino–Sugars," *Chemistry and Industry* pp. 1794–1795 (Oct. 13, 1962).

Reynolds and Miller, "Ifenprodil is a Novel Type of N–Methyl–D–Aspartate Receptor Antagonist: Interaction with Polyamines," *Molecular Pharmacology* 36:758–765 (1989).

Reynolds, "Arcaine is a Competitive Antagonist of the Polyamine Site on the NMDA Receptor," *European Journal of Pharmacology* 177:215–216 (1990).

Reynolds, "The Spider Toxin, Argiotoxin$_{636}$, Binds to a Mg$^{2+}$ Site on the N–Methyl–D–Aspartate Receptor Complex," *Br. Journal of Pharmacology* 103(2):1373–1376 (1991).

Reynolds, *Martindale: The Extra Pharmacopoeia*, The Pharmaceutical Press, London, pp. 543–544 (1989).

Rock and MacDonald, "Spermine and Related Polyamines Produce a Voltage–Dependent Reduction of N–Methyl––D–Aspartate Receptor Single–Channel Conductance," *Molecular Pharmacology* 42:157–164 (1992).

Rogawski, "Therapeutic Potential of Excitatory Amino Acid Antagonists: Channel Blockers and 2,3–benzodiazepines," *Trends in Pharmacol. Sci.* 14:325–331 (1993).

Rozental et al., "Allosteric Inhibition of Nicotinic Acetylcholine Receptors of Vertebrates and Insects by Philanthotoxin," *Journal of Pharmacology and Experimental Therapeutics* 249:123–130 (1989).

Sacaan and Johnson, "Characterization of the Stimulatory and Inhibitory Effects of Polyamines on [$^3$H]N–(1–[thienyl] cyclohexyl) piperidine Binding to the N–Methyl–D–Aspartate Receptor Ionophore Complex," *Molecular Pharmacology* 37:572–577 (1990).

Saccomano et al., "Arylamine NMDA Antagonists From Spider Venom," *201st American Chemical Society National Meeting, Abstracts of Papers—Part 1*, Atlanta, Georgia, Apr. 14–19 (1991) (Abstract #10).

Saccomano et al., "Ch 30—Polyamine Spider Toxins: Unique Pharmacological Tools," in *Annual Reports in Medicinal Chemistry* 24:287–293 (1989).

Saito et al., "Effects of a Spider Toxin (JSTX) on Hippocampal CA1 Neurons in vitro," *Brain Research* 481:16–24 (1989).

Saito et al., "Spider Toxin (JSTX) Blocks Glutamate Synapse in Hippocampal Pyramidal Neurons," *Brain Research* 346:397–399 (1985).

Scatchard, "The Attractions of Proteins For Small Molecules and Ions," *Annals New York Academy of Sciences* 51:660–672 (1949).

Scatton, "Therapeutic potential of NMDA receptor antagonists in Ischemic Cerebrovascular disease in drug strategies in the prevention and treatment of stroke," *IBC Technical Services, LTD.* (1990).

Scatton et al., "NMDA Receptor Antagonists: Treatment for Brain Ischemia," *Drug News & Perspectives* 4(2):89–95 (1991).

Seymour and Mena, "In Vivo NMDA Antagonist Activity of the Polyamine Spider Venom Component, Argiotoxin–636," *Soc. Neurosci. Abst.* 15:1168 at abstract No. 463.24 (1989).

Snell and Johnson, "Ch 13—Phencyclidine: Behavioral Correlates of NMDA Antagonsim," in *Excitatory Amino Acids in Health and Disease*, D. Lodge editor, John Wiley & Sons, pp. 261–273 (1988).

Snyder, "Neurotransmitter Receptor Binding and Drug Discovery," *J. Med. Chem.* 26:1667–1672 (1983).

Sutton et al., "Inhibition of voltage–activated Ca$^{2+}$ currents from cultured sensory neurones by spermine, argiotoxin–636 and a synthetic arginine polyamine," *Molecular Neuropharmacology* 3:37–43 (1993).

Tang et al., Phencyclidine–Like Behavioral Effects of 2–Methyl–3,3–Diphenyl–3–Propanolamine (2–MDP), *Pharmacology Biochemistry & Behavior* 20:209–213 (1984).

Teylor and DiScenna, "Long–Term Potentiation," *Annu. Rev. Neurosci.* 10:131–161 (1987).

Titeler, *Multiple Dopamine Receptors: Receptor Binding Studies in Dopamine Pharmacology, vol. 1*, Marcel Dekker, Inc., New York, pp. 1–173 (1983).

Usherwood and Blagbrough, "Spider Toxins Affecting Glutamate Receptors: Polyamines in Therapeutic Neurochemistry," *Pharmac. Ther.* pp. 1–24 (1992).

Watkins and Collingridge, "Phenylglycine derivatives as antagonists of metabotropic glutamate receptors," *TIPS* 15:333–342 (1994).

White et al., "Some Pharmacological Properties of 3:3–Diphenyl–Propanolamines,—Allylamines and –Propylamines," *Brit. J. Pharmacol.* 6:560–571 (1951).

Wiley and Balster, "Preclinical Evaluation of N–Methyl––D–Aspartate Antagonists for Antianxiety Effects: A Review," *Multiple Sigma and PCP Receptor Ligands: Mechanisms for Neuromodulation and Neuroprotection?* NPP Books, Ann Arbor, Michigan, pp. 801–815 (1992).

Willetts et al., "The Behavioral Pharmacology of NMDA Receptor Antagonists," *Trends Pharmacol. Sci.* 11:423–428 (1990).

Williams et al., "Characterization of Polyamines Having Agonist, Antagonist, and Inverse Agonist Effects at the Polyamine Recognition Site of the NMDA Receptor," *Neuron* 5:199–208 (1990).

Williams et al., "Effects of Polyamines on the Binding of [$^3$H]MK–801 to the N–Methyl–D–Aspartate Receptor: Pharmacological Evidence for the Existence of a Polyamine Recognition Site," *Molecular Pharmacology* 36:575–581 (1989).

Williams, "Effects of *Agelenopsis aperta* Toxins on the N–Methyl–D–Aspartate Receptor: Polyamine–Like and High–Affinity Antagonist Actions," *Journal of Pharmacology and Experimental Therapeutics* 266:231–236 (1993).

Williams, "Ifenprodil Discriminates Subtypes of the N–Methyl–D–Aspartate Receptor: Selectivity and Mechanisms at Recombinant Heteromeric Receptors," *Molecular Pharmacology* 44:851–859 (1993).

Yamaguchi et al., "Anticonvulsant Activity of AMPA/Kainate Antagonists: Comparison of GYKI 52466 and NBQX in Maximal Electroshock and Chemoconvulsant Seizure Models," *Epilepsy Research* 15:179–184 (1993).

COMPOUNDS ACTIVE AT A NOVEL SITE ON RECEPTOR-OPERATED CALCIUM CHANNELS USEFUL FOR TREATMENT OF NEUROLOGICAL DISORDERS AND DISEASES

This is a continuation of application Ser. No. 08/485,038 filed Jun. 7, 1995 which is a continuation-in-part of International Patent Application No. PCT/US94/12293, filed Oct. 26, 1994, designating the United States, which is a continuation-in-part of application U.S. Ser. No. 08/288,668, filed Aug. 9, 1994, now abandoned, which is a continuation-in-part of application U.S. Ser. No. 08/194,210, filed Feb. 8, 1994, now abandoned, which is a continuation-in-part of U.S. Ser. No. 08/014,813, filed Feb. 8, 1993, now abandoned.

FIELD OF THE INVENTION

This invention relates to compounds useful as neuroprotectants, anticonvulsants, anxiolytics, analgesics, muscle relaxants or adjuvants to general anesthetics. The invention relates as well to methods useful for treatment of neurological disorders and diseases, including, but not limited to, global and focal ischemic and hemorrhagic stroke, head trauma, spinal cord injury, hypoxia-induced nerve cell damage such as in cardiac arrest or neonatal distress, epilepsy, anxiety, and neurodegenerative diseases such as Alzheimer's Disease, Huntington's Disease, Parkinson's Disease, and amyotrophic lateral sclerosis (ALS). The invention relates as well to methods of screening for compounds active at a novel site on receptor-operated calcium channels, and thereby possessing therapeutic utility as neuroprotectants, anticonvulsants, anxiolytics, analgesics, muscle relaxants or adjuvants to general anesthetics, and/or possessing potential therapeutic utility for the treatment of neurological disorders and diseases as described above.

BACKGROUND OF THE INVENTION

The following is a description of relevant art, none of which is admitted to be prior art to the claims.

Glutamate is the major excitatory neurotransmitter in the mammalian brain. Glutamate binds or interacts with one or more glutamate receptors which can be differentiated pharmacologically into several subtypes. In the mammalian central nervous system (CNS) there are three main subtypes of ionotropic glutamate receptors, defined pharmacologically by the selective agonists N-methyl-D-aspartate (NMDA), kainate (KA), and α-amino-3-hydroxy-5-methylisoxazole-4-propionic acid (AMPA). The NMDA receptor has been implicated in a variety of neurological pathologies including stroke, head trauma, spinal cord injury, epilepsy, anxiety, and neurodegenerative diseases such as Alzheimer's Disease (Watkins and Collingridge, The NMDA Receptor, Oxford: IRL Press, 1989). A role for NMDA receptors in nociception and analgesia has been postulated as well (Dickenson, A cure for wind-up: NMDA receptor antagonists as potential analgesics. Trends Pharmacol. Sci. 11: 307, 1990). More recently, AMPA receptors have been widely studied for their possible contributions to such neurological pathologies (Fisher and Bogousslavsky, Evolving toward effective therapy for acute ischemic stroke. J. Amer. Med. Assoc. 270: 360, 1993; Yamaguchi et al., Anticonvulsant activity of AMPA/kainate antagonists: comparison of GYKI 52466 and NBQX in maximal electroshock and chemoconvulsant seizure models. Epilepsy Res. 15: 179, 1993).

When activated by glutamate, the endogenous neurotransmitter, the NMDA receptor permits the influx of extracellular calcium ($Ca^{2+}$) and sodium ($Na^+$) through an associated ion channel. The NMDA receptor allows considerably more influx of $Ca^{2+}$ than do kainate or AMPA receptors (but see below), and is an example of a receptor-operated $Ca^{2+}$ channel. Normally, the channel is opened only briefly, allowing a localized and transient increase in the concentration of intracellular $Ca^{2+}$ ($[Ca^{2+}]_i$) which, in turn, alters the functional activity of the cell. However, prolonged increases in $[Ca^{2+}]_i$, resulting from chronic stimulation of the NMDA receptor, are toxic to the cell and lead to cell death. The chronic elevation in $[Ca^{2+}]_i$, resulting from stimulation of NMDA receptors, is said to be a primary cause of neuronal degeneration following a stroke (Choi, Glutamate neurotoxicity and diseases of the nervous system. Neuron 1: 623, 1988). Overstimulation of NMDA receptors is also said to be involved in the pathogenesis of some forms of epilepsy (Dingledine et al., Excitatory amino acid receptors in epilepsy. Trends Pharmacol. Sci. 11: 334, 1990), anxiety (Wiley and Balster, Preclinical evaluation of N-methyl-D-aspartate antagonists for antianxiety effects: A review. In: Multiple Sigma and PCP Receptor Ligands: Mechanisms for Neuromodulation and Neuroprotection? NPP Books, Ann Arbor, Mich., pp. 801–815, 1992) neurodegenerative diseases (Meldrum and Garthwaite, Excitatory amino acid neurotoxicity and neurodegenerative disease. Trends Pharmacol. Sci. 11: 379, 1990), and hyperalgesic states (Dickenson, A cure for wind-up: NMDA receptor antagonists as potential analgesics. Trends Pharmacol. Sci. 11: 307, 1990).

The activity of the NMDA receptor-ionophore complex is regulated by a variety of modulatory sites that can be targeted by selective antagonists. Competitive antagonists, such as the phosphonate AP5, act at the glutamate binding site, whereas noncompetitive antagonists, such as phencyclidine (PCP), MK-801 or magnesium ($Mg^{2+}$), act within the associated ion channel (ionophore). There is also a glycine binding site that can be blocked selectively with compounds such as 7-chlorokynurenic acid. There is evidence suggesting that glycine acts as a co-agonist, so that both glutamate and glycine are necessary to fully elicit NMDA receptor-mediated responses. Other potential sites for modulation of NMDA receptor function include a zinc ($Zn^{2+}$) binding site and a sigma ligand binding site. Additionally, endogenous polyamines such as spermine are believed to bind to a specific site and so potentiate NMDA receptor function (Ransom and Stec, Cooperative modulation of [$^3$H]MK-801 binding to the NMDA receptor-ion channel complex by glutamate, glycine and polyamines. J. Neurochem. 51: 830, 1988). The potentiating effect of polyamines on NMDA receptor function may be mediated via a specific receptor site for polyamines; polyamines demonstrating agonist, antagonist, and inverse agonist activity have been described (Reynolds, Arcaine is a competitive antagonist of the polyamine site on the NMDA receptor. Europ. J. Pharmacol. 177: 215, 1990; Williams et al., Characterization of polyamines having agonist, antagonist, and inverse agonist effects at the polyamine recognition site of the NMDA receptor. Neuron 5: 199, 1990). Radioligand binding studies have demonstrated additionally that higher concentrations of polyamines inhibit NMDA receptor function (Reynolds and Miller, Ifenprodil is a novel type of NMDA receptor antagonist: Interaction with polyamines. Molec. Pharmacol. 36: 758, 1989; Williams et al., Effects of polyamines on the binding of [$^3$H]MK-801 to the NMDA receptor: Pharmacological evidence for the existence of a polyamine recognition site. *Molec. Pharmacol.* 36: 575, 1989; Sacaan and Johnson, Characterization of the stimulatory and inhibitory effects of polyamines on [$^3$H]TCP binding to the NMDA receptor-ionophore complex. *Molec. Pharmacol.* 37: 572, 1990). This inhibitory effect of polyamines on NMDA receptors is probably a nonspecific effect (i.e., not mediated via the polyamine receptor) because patch clamp electrophysiological studies have demonstrated that this inhibition is produced by compounds previously shown to act at the polyamine receptor as either agonists or antagonists (Donevan et al., Arcaine Blocks N-Methyl-D-Aspartate Receptor Responses by an Open Channel Mechanism: Whole-Cell and Single-Channel Recording Studies in Cultured Hippocampal Neurons. *Molec. Pharmacol.* 41: 727, 1992; Rock and Macdonald, Spermine and Related Polyamines Produce a Voltage-Dependent Reduction of NMDA Receptor Single-Channel Conductance. *Molec. Pharmacol.* 42: 157, 1992).

Recent studies have demonstrated the molecular diversity of glutamate receptors (reviewed by Nakanishi, Molecular Diversity of Glutamate Receptors and Implications for Brain Function. *Science* 258: 597, 1992). At least five distinct NMDA receptor subunits (NMDAR1 and NMDAR2A through NMDAR2D), each encoded by a distinct gene, have been identified to date. Also, in NMDAR1, alternative splicing gives rise to at least six additional isoforms. It appears that NMDAR1 is a necessary subunit, and that combination of NMDAR1 with different members of NMDAR2 forms the fully functional NMDA receptor-ionophore complex. The NMDA receptor-ionophore complex, thus, can be defined as a hetero-oligomeric structure composed of at least NMDAR1 and NMDAR2 subunits; the existence of additional, as yet undiscovered, subunits is not excluded by this definition. NMDAR1 has been shown to possess binding sites for glutamate, glycine, $Mg^{2+}$, MK-801, and $Zn^{2+}$. The binding sites for sigma ligands and polyamines have not yet been localized on NMDA receptor subunits, although ifenprodil recently has been reported to be more potent at the NMDAR2B subunit than at the NMDAR2A subunit (Williams, Ifenprodil discriminates subtypes of the N-Methyl-D-aspartate receptor: selectivity and mechanisms at recombinant heteromeric receptors. Mol. Pharmacol. 44: 851, 1993).

Several distinct subtypes of AMPA and kainate receptors have been cloned as well (reviewed by Nakanishi, Molecular diversity of glutamate receptors and implications for brain function. *Science* 258: 597, 1992). Of particular relevance are the AMPA receptors designated GluR1, GluR2, GluR3, and GluR4 (also termed GluRA through GluRD), each of which exists in one of two forms, termed flip and flop, which arise by RNA alternative splicing. GluR1, GluR3 and GluR4, when expressed as homomeric or heteromeric receptors, are permeable to $Ca^{2+}$, and are therefore examples of receptor-operated $Ca^{2+}$ channels. Expression of GluR2 alone or in combination with the other subunits gives rise to a receptor which is largely impermeable to $Ca^{2+}$. As most native AMPA receptors studied in situ are not $Ca^{2+}$-permeable (discussed above), it is believed that such receptors in situ possess at least one GluR2 subunit. Furthermore, it is hypothesized that the GluR2 subunit is functionally distinct by virtue of the fact that it contains an arginine residue within the putative pore-forming transmembrane region II; GluR1, GluR3 and GluR4 all contain a glutamine residue in this critical region (termed the Q/R site, where Q and R are the single letter designations for glutamine and arginine, respectively). The activity of the AMPA receptor is regulated by a number of modulatory sites that can be targeted by selective antagonists (Honore et al., Quinoxalinediones: potent competitive non-NMDA glutamate receptor antagonists. *Science* 241: 701, 1988; Donevan and Rogawski, GYKI 52466, a 2,3-benzodiazepine, is a highly selective, noncompetitive antagonist of AMPA/kainate receptor responses. *Neuron* 10: 51, 1993). Competitive antagonists such as NBQX act at the glutamate binding site, whereas compounds such as GYKI 52466 appear to act noncompetitively at an associated allosteric site.

Compounds that act as competitive or noncompetitive antagonists at the NMDA receptor are said to be effective in preventing neuronal cell death in various in vitro neurotoxicity assays (Meldrum and Garthwaite, Excitatory amino acid neurotoxicity and neurodegenerative disease. *Trends Pharmacol. Sci.* 11: 379, 1990) and in in vivo models of stroke (Scatton, Therapeutic potential of NMDA receptor antagonists in ischemic cerebrovascular disease in *Drug Strategies in the Prevention and Treatment of Stroke,* IBC Technical Services Ltd., 1990). Such compounds are also effective anticonvulsants (Meldrum, Excitatory amino acid neurotransmission in epilepsy and anticonvulsant therapy in *Excitatory Amino Acids.* Meldrum, Moroni, Simon, and Woods (Eds.), New York: Raven Press, p. 655, 1991), anxiolytics (Wiley and Balster, Preclinical evaluation of N-methyl-D-aspartate antagonists for antianxiety effects: A review. In: *Multiple Sigma and PCP Receptor Ligands: Mechanisms for Neuromodulation and Neuroprotection?* NPP Books, Ann Arbor, Mich., pp. 801–815, 1992), and analgesics (Dickenson, A cure for wind-up: NMDA receptor antagonists as potential analgesics. *Trends Pharmacol. Sci.* 11: 307, 1990), and certain NMDA receptor antagonists may lessen dementia associated with Alzheimer's Disease (Hughes, Merz' novel approach to the treatment of dementia. *Script* No. 1666: 24, 1991).

Similarly, AMPA receptor antagonists have come under intense scrutiny as potential therapeutic agents for the treatment of such neurological disorders and diseases. AMPA receptor antagonists have been shown to possess neuroprotectant (Fisher and Bogousslavsky, Evolving toward effective therapy for acute ischemic stroke. *J. Amer. Med. Assoc.* 270: 360, 1993) and anticonvulsant (Yamaguchi et al., Anticonvulsant activity of AMPA/kainate antagonists: comparison of GYKI 52466 and NBQX in maximal electroshock and chemoconvulsant seizure models. *Epilepsy Res.* 15: 179, 1993) activity in animal models of ischemic stroke and epilepsy, respectively.

The nicotinic cholinergic receptor present in the mammalian CNS is another example of a receptor-operated $Ca^{2+}$ channel (Deneris et al., Pharmacological and functional diversity of neuronal nicotinic acetylcholine receptors. *Trends Pharmacol. Sci.* 12: 34, 1991). Several distinct receptor subunits have been cloned, and these subunits can be expressed, in Xenopus oocytes for example, to form functional receptors with their associated cation channels. It is hypothesized that such receptor-ionophore complexes are heteropentameric structures. The possible role of nicotinic receptor-operated $Ca^{2+}$ channels in the pathology of neurological disorders and diseases such as ischemic stroke, epilepsy and neurodegenerative diseases has been largely unexplored.

It has been demonstrated previously (for reviews see Jackson and Usherwood, Spider toxins as tools for dissecting elements of excitatory amino acid transmission. *Trends Neurosci.* 11: 278, 1988; Jackson and Parks, Spider Toxins: Recent Applications In Neurobiology. *Annu. Rev. Neurosci.* 12: 405, 1989; Saccomano et al., Polyamine spider toxins: Unique pharmacological tools. *Annu. Rep. Med. Chem.* 24:

287, 1989; Usherwood and Blagbrough, Spider Toxins Affecting Glutamate Receptors: Polyamines in Therapeutic Neurochemistry. *Pharmacol. Therap.* 52: 245, 1991; Kawai, Neuroactive Toxins of Spider Venoms. *J. Toxicol. Toxin Rev.* 10: 131, 1991) that certain spider and wasp venoms contain arylalkylamine toxins (also called polyamine toxins, arylamine toxins, acylpolyamine toxins or polyamine amide toxins) with activity against glutamate receptors in the mammalian CNS. Arylalkylamine toxins were initially reported to be selective antagonists of the AMPA/kainate subtypes of glutamate receptors in the mammalian CNS (Kawai et al., Effect of a spider toxin on glutaminergic synapses in the mammalian brain. *Biomed. Res.* 3: 353, 1982; Saito et al., Spider Toxin (JSTX) blocks glutamate synapse in hippocampal pyramidal neurons. *Brain Res.* 346: 397, 1985; Saito et al., Effects of a spider toxin (JSTX) on hippocampal CA1 neurons in vitro. *Brain Res.* 481: 16, 1989; Akaike et al., Spider toxin blocks excitatory amino acid responses in isolated hippocampal pyramidal neurons. *Neurosci. Lett.* 79: 326, 1987; Ashe et al., Argiotoxin-636 blocks excitatory synaptic transmission in rat hippocampal CA1 pyramidal neurons. *Brain Res.* 480: 234, 1989; Jones et al., Philanthotoxin blocks quisqualate-induced, AMPA-induced and kainate-induced, but not NMDA-induced excitation of rat brainstem neurones in vivo. *Br. J. Pharmacol.* 101: 968, 1990). Subsequent studies have demonstrated that while certain arylalkylamine toxins are both nonpotent and nonselective at various glutamate receptors, other arylalkylamines are both very potent and selective at antagonizing responses mediated by NMDA receptor activation in the mammalian CNS (Mueller et al., Effects of polyamine spider toxins on NMDA receptor-mediated transmission in rat hippocampus in vitro. *Soc. Neurosci. Abst.* 15: 945, 1989; Mueller et al., Arylamine spider toxins antagonize NMDA receptor-mediated synaptic transmission in rat hippocampal slices. *Synapse* 9: 244, 1991; Parks et al., Polyamine spider toxins block NMDA receptor-mediated increases in cytosolic calcium in cerebellar granule neurons. *Soc. Neurosci. Abst.* 15: 1169, 1989; Parks et al., Arylamine toxins from funnel-web spider (*Agelenopsis aperta*) venom antagonize N-methyl-D-aspartate receptor function in mammalian brain. *J. Biol. Chem.* 266: 21523, 1991; Priestley et al., Antagonism of responses to excitatory amino acids on rat cortical neurones by the spider toxin, argiotoxin-636. *Br. J. Pharmacol.* 97: 1315, 1989; Draguhn et al., Argiotoxin-636 inhibits NMDA-activated ion channels expressed in Xenopus oocytes. *Neurosci. Lett.* 132: 187, 1991; Kiskin et al., A highly potent and selective N-methyl-D-aspartate receptor antagonist from the venom of the *Agelenopsis aperta* spider. *Neuroscience* 51: 11, 1992; Brackley et al., Selective antagonism of native and cloned kainate and NMDA receptors by polyamine-containing toxins. *J. Pharmacol. Exp. Therap.* 266: 1573, 1993; Williams, Effects of *Agelenopsis aperta* toxins on the N-methyl-D-aspartate receptor: Polyamine-like and high-affinity antagonist actions. *J. Pharmacol. Exp. Therap.* 266: 231, 1993). Inhibition of nicotinic cholinergic receptors by the arylalkylamine toxin philanthotoxin has also been reported (Rozental et al., Allosteric inhibition of nicotinic acetylcholine receptors of vertebrates and insects by philanthotoxin. *J. Pharmacol. Exp. Therap.* 249: 123, 1989).

Parks et al. (Arylamine toxins from funnel-web spider (*Agelenopsis aperta*) venom antagonize N-methyl-D-aspartate receptor function in mammalian brain. *J. Biol. Chem.* 266: 21523, 1991), describe arylalkylamine spider toxins (α-agatoxins) which antagonize NMDA receptor function in mammalian brain.. The authors discuss the mechanism of action of arylalkylamine toxins, and indicate that an NMDA receptor-operated ion channel is the probable site of action of the α-agatoxins, and most probably other spider venom arylalkylamines. They state:

"The discovery that endogenous polyamines in the vertebrate brain modulate the function of NMDA receptors suggests that the arylamine toxins may produce their antagonism via a polyamine-binding site on glutamate receptors. Brackley et al. studied the effects of spermine and philanthotoxin 433 on the responses evoked by application of excitatory amino acids in Xenopus oocytes injected with mRNA from rat or chick brain. These authors reported that, at concentrations below those that antagonize glutamate receptor function, both spermine and philanthotoxin potentiate the effects of excitatory amino acids and some other neurotransmitters. On the basis of these and other data, Brackley et al. concluded that the arylamine toxins may, by binding nonspecifically to the membranes of excitable cells, reduce membrane fluidity and alter receptor function. The validity of this intriguing idea for NMDA receptor function is not well supported by two recent binding studies. Reynolds reported that argiotoxin 636 inhibits the binding of [$^3$H]MK-801 to rat brain membranes in a manner that is insensitive to glutamate, glycine, or spermidine. This author concluded that argiotoxin 636 exerts a novel inhibitory effect on the NMDA receptor complex by binding to one of the $Mg^{2+}$ sites located within the NMDA-gated ion channel. Binding data reported by Williams et al. also support the conclusion that argiotoxin 636 does not act primarily at the polyamine modulatory site on the NMDA receptor, but rather acts directly to produce an activity-dependent block of the ion channel. It is already known that compounds such as phencyclidine and ketamine can block the ion channels associated with both arthropod muscle glutamate receptors and mammalian NMDA receptors. Thus, it seems possible that vertebrate and invertebrate glutamate receptors share additional binding sites for allosteric modulators of receptor function, perhaps related to divalent cation-binding sites. Clearly, considerable additional work will be needed to determine if the arylamines define such a novel regulatory site."

Usherwood and Blagbrough (Spider Toxins Affecting Glutamate Receptors: Polyamines in Therapeutic Neurochemistry. *Pharmacol. Therap.* 52: 245, 1991) describe a proposed intracellular binding site for arylalkylamine toxins (polyamine amide toxins) located within the membrane potential field referred to as the QUIS-R channel selectivity filter. The authors postulate that the binding site for polyamine amide toxins may occur close to the internal entrance of the channel gated by the QUIS-R of locust muscle. The authors also note that one such toxin, argiotoxin-636, selectively antagonizes the NMDA receptor in cultured rat cortical neurons.

Gullak et al. (CNS binding sites of the novel NMDA antagonist Arg-636. *Soc. Neurosci. Abst.* 15: 1168, 1989), describe argiotoxin-636 (Arg-636) as a polyamine (arylalkylamine) toxin component of a spider venom. This toxin is said to block NMDA-induced elevation of cGMP in a noncompetitive fashion. The authors state that:

"[$^{125}$I]Arg-636 bound to rat forebrain membranes with $K_d$ and $B_{max}$ values of 11.25 μM and 28.95 pmol/mg protein (80% specific). The ability of other known polyamines and recently discovered polyamines from *Agelenopsis aperta* to inhibit binding paralleled neuroactivity as functional NMDA antagonists. No other compounds tested were able to block specific binding." The authors then stated that polyamines (arylalkylamines) may antagonize responses to NMDA by interacting with membrane ion channels.

Seymour and Mena (In vivo NMDA antagonist activity of the polyamine spider venom component, argiotoxin-636. *Soc. Neurosci. Abst.* 15: 1168, 1989) describe studies that are said to show that argiotoxin-636 does not significantly affect locomotor activity at doses that are effective against audiogenic seizures in DBA/2 mice, and that it significantly antagonizes NMDA-induced seizures with a minimal effective dose of 32 mg/kg given subcutaneously (s.c.).

Herold and Yaksh (Anesthesia and muscle relaxation with intrathecal injections of AR636 and AG489, two acylpolyamine spider toxins, in rats. *Anesthesiology* 77: 507, 1992) describe studies that are said to show that the arylalkylamine argiotoxin-636 (AR636), but not agatoxin-489 (AG489), produces muscle relaxation and anesthesia following intrathecal administration in rats.

Williams (Effects of *Agelenopsis aperta* toxins on the N-methyl-D-aspartate receptor: Polyamine-like and high-affinity antagonist actions, *J. Pharmacol. Exp. Therap.* 266: 231, 1993) reports that the α-agatoxins (arylalkylamines) Agel-489 and Agel-505 enhance the binding of [$^3$H]MK-801 to NMDA receptors on membranes prepared from rat brain by an action at the stimulatory polyamine receptor; polyamine receptor agonists occluded the stimulatory effects of Agel-489 and Agel-505 and polyamine receptor antagonists inhibited the stimulatory effect of Agel-505. Higher concentrations of Agel-489 and Agel-505, and argiotoxin-636 at all concentrations tested, had inhibitory effects on the binding of [$^3$H]MK-801. In Xenopus oocytes voltage-clamped at −70 mV, Agel-505 inhibited responses to NMDA with an $IC_{50}$ of 13 nM; this effect of Agel-505 occurred at concentrations approximately 10,000-fold lower than those that affected [$^3$H]MK-801 binding. Responses to kainate were inhibited only 11% by 30 nM Agel-505. The antagonism of NMDA-induced currents by Agel-505 was strongly voltage-dependent, consistent with an open-channel blocking effect of the toxin. Williams states:

"Although α-agatoxins can interact at the positive allosteric polyamine site on the NMDA receptor, stimulatory effects produced by this interaction may be masked in functional assays due to a separate action of the toxins as high-affinity, noncompetitive antagonists of the receptor."

Brackley et al. (Selective antagonism of native and cloned kainate and NMDA receptors by polyamine-containing toxins, *J. Pharmacol. Exp. Therap.* 266: 1573, 1993) report that the polyamine-containing toxins (arylalkylamines) philanthotoxin-343 (PhTX-343) and argiotoxin-636 (Arg-636) produce reversible, noncompetitive, partly voltage-dependent antagonism of kainate- and NMDA-induced currents in Xenopus oocytes injected with rat brain RNA. Arg-636 was demonstrated to be selective for NMDA-induced responses ($IC_{50}$=0.04 μM) compared to kainate-induced responses ($IC_{50}$=0.07 μM), while PhTX-343 was selective for kainate-induced responses ($IC_{50}$=0.12 μM) compared to NMDA-induced responses ($IC_{50}$=2.5 μM). Arg-636 more potently antagonized responses to NMDA in Xenopus oocytes expressing cloned NMDAR1 subunits ($IC_{50}$=0.09 μM) than responses to kainate in oocytes expressing either cloned GluR1 ($IC_{50}$=3.4 μM) or GluR1+GluR2 subunits ($IC_{50}$≈300 μM). PhTX-343, on the other hand, was equipotent at antagonizing NMDAR1 ($IC_{50}$=2.19 μM) and GluR1 ($IC_{50}$=2.8 μM), but much less potent against GluR1+GluR2 subunits ($IC_{50}$=270 μM).

Raditsch et al. (Subunit-specific block of cloned NMDA receptors by argiotoxin-636. *FEBS Lett.* 324: 63, 1993) report that Arg-636 more potently antagonizes responses in Xenopus oocytes expressing NMDAR1+NMDAR2A subunits ($IC_{50}$=9 nM) or NMDAR1+NMDAR2B subunits ($IC_{50}$=2.5 nM) than NMDAR1+NMDAR2C subunits ($IC_{50}$=460 nM), even though all of the receptor subunits contain an asparagine residue in the putative pore-forming transmembrane region II (the Q/R site, as discussed above). The authors state that the large difference in Arg-636 sensitivity between NMDAR1+NMDAR2A and NMDAR1+NMDAR2C channels "must be conferred by other structural determinants."

Herlitz et al. (Argiotoxin detects molecular differences in AMPA receptor channels. *Neuron* 10: 1131, 1993) report that Arg-636 antagonizes subtypes of AMPA receptors in a voltage- and use-dependent manner consistent with open-channel blockade. Arg-636 potently antagonizes $Ca^{2+}$-permeable AMPA receptors comprised of GluRAi ($K_i$=0.35 μM), GluRCi ($K_i$=0.23 μM), or GluRDi subunits ($K_i$=0.43 μM), while being essentially ineffective against $Ca^{2+}$-impermeable GluRBi subunits at concentrations up to 10 μM. Other data reported by these investigators strongly suggest that the Q/R site in the putative pore-forming transmembrane region II is of primary importance in determining Arg-636 potency and $Ca^{2+}$ permeability.

Blaschke et al. (A single amino acid determines the subunit-specific spider toxin block of α-amino-3-hydroxy-5-methylisoxazole-4-propionate/kainate receptor channels. *Proc. Natl. Acad. Sci. USA* 90: 6528, 1993) report that the arylalkylamine JSTX-3 potently antagonizes responses to kainate in Xenopus oocytes expressing GluR1 ($IC_{50}$=0.04 μM) or GluR3 ($IC_{50}$=0.03 μM) subunits, but that expressed receptors in which a GluR2 subunit is present are essentially unaffected by the toxin. Site-directed mutagenesis studies strongly implicate the Q/R site as the primary site influencing toxin potency.

Nakanishi et al. (Bioorganic studies of transmitter receptors with philanthotoxin analogs. *Pure Appl. Chem.*, in press) have synthesized a number of highly potent photoaffinity labeled philanthotoxin (PhTX) analogs. Such analogs have been studied on expressed nicotinic cholinergic receptors as a model system for receptor-operated calcium channels receptors. These investigators suggest that these PhTX analogs block the ion channel with the hydrophobic headpiece of the toxin binding to a site near the cytoplasmic surface while the polyamine tail extends into the ion channel from the cytoplasmic side.

SUMMARY OF THE INVENTION

Applicant has examined the structural diversity and biological activity of arylalkylamines (sometimes referred to as arylamine toxins, polyamine toxins, acylpolyamine toxins or polyamine amide toxins) in spider and wasp venoms, and determined that some of the arylalkylamines present in these venoms act as potent noncompetitive antagonists of glutamate receptor-operated $Ca^{2+}$ channels in the mammalian CNS. Although these arylalkylamine compounds contain within their structure a polyamine moiety, they are unlike other known simple polyamines in possessing extremely potent and specific effects on certain types of receptor-operated $Ca^{2+}$ channels.

Using native arylalkylamines as lead structures, a number of analogs were synthesized and tested. Initial findings on arylalkylamines isolated and purified from venom were confirmed utilizing synthetic arylalkylamines. These compounds are small molecules (mol. wt. <800) with demonstrated efficacy in in vivo models of stroke and epilepsy. The NMDA receptor-ionophore complex was used as a model of receptor-operated $Ca^{2+}$ channels. Selected arylalkylamines were shown to block NMDA receptor-mediated responses by a novel mechanism. Moreover, the unique behavioral pharmacological profile of these compounds suggests that they are unlikely to cause the PCP-like psychotomimetic activity and cognitive deficits that characterize other inhibitors of the NMDA receptor. Finally, the arylalkylamines are unique amongst NMDA receptor antagonists in that they are able to antagonize certain subtypes of cloned and expressed AMPA receptors, namely, those permeable to $Ca^{2+}$. The arylalkylamines, therefore, are the only known class of compounds able to antagonize glutamate receptor-mediated arylalkylamine binding site, and by determining whether such a compound has the required biological, pharmacological and physiological properties.

Thus, in a first aspect, the invention features a method for screening for a therapeutically useful compound active at one or more receptor-operated $Ca^{2+}$ channels, as a noncompetitive antagonist. Such a compound may alternatively or in addition be useful as a biopesticide or a pharmacological tool. The method includes the step of identifying a compound which binds to the receptor-operated $Ca^{2+}$ channel at that site bound by the arylalkylamine compounds referred to herein as Compound 1, Compound 2 or Compound 3, and having the structures shown below.

Compound 1

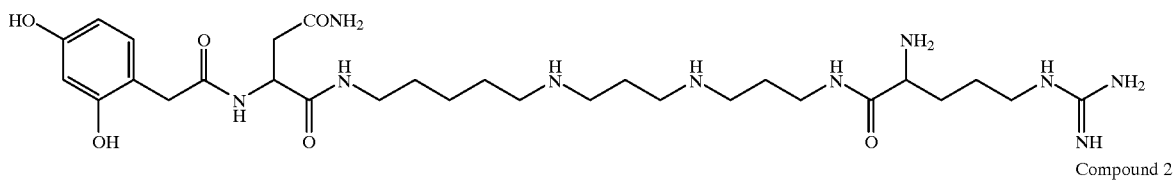

Compound 2

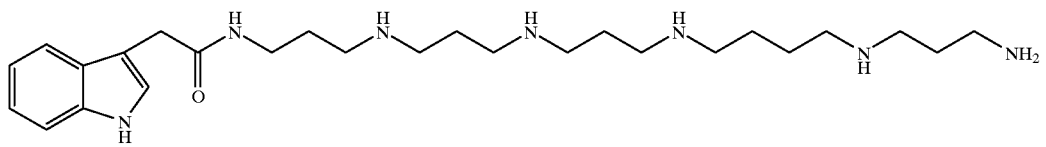

Compound 3

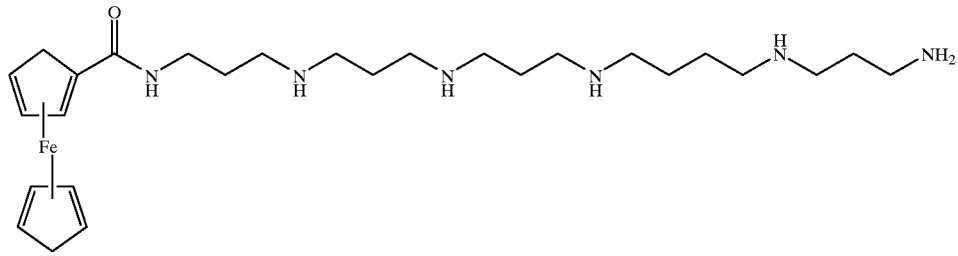

increases in cytosolic $Ca^{2+}$ regardless of the pharmacological definition of receptor subtype. Additionally, the arylalkylamines inhibit another receptor-operated $Ca^{2+}$ channel, the nicotinic cholinergic receptor. Given that excessive and prolonged increases in cytosolic $Ca^{2+}$ have been implicated in the etiology of several neurological disorders and diseases, such arylalkylamines are valuable small molecule leads for the development of novel therapeutics for various neurological disorders and diseases.

Applicant has determined that the selected arylalkylamines bind with high affinity at a novel site on the NMDA receptor-ionophore complex which has heretofore been unidentified, and that said arylalkylamines do not bind with high affinity at any of the known sites (glutamate binding site, glycine binding site, MK-801 binding site, $Mg^{2+}$ binding site, $Zn^{2+}$ binding site, polyamine binding site, sigma binding site) on said NMDA receptor-ionophore complex. This determination has allowed applicant to develop methods and protocols by which useful compounds can be identified which provide both therapeutically useful compounds and lead compounds for the development of other therapeutically useful compounds. These compounds can be identified by screening for compounds that bind at this novel In preferred embodiments, the invention features a method to identify one or more compounds active at a receptor-operated calcium channel which is part of an NMDA receptor-ionophore complex, part of a calcium-permeable AMPA receptor-ionophore complex, or part of a nicotinic cholinergic receptor-ionophore complex, and where the therapeutic use is for treatment of a neurological disorder or disease, or as a neuroprotectant, anticonvulsant, anxiolytic, analgesic, muscle relaxant or adjunct in general anesthesia.

By "therapeutically useful compound" is meant a compound that is potentially useful in the treatment of a disorder or disease state. A compound uncovered by the screening method is characterized as having potential therapeutic utility in treatment because clinical tests have not yet been conducted to determine actual therapeutic utility.

By "neurological disorder or disease" is meant a disorder or disease of the nervous system including, but not limited to, global and focal ischemic and hemorrhagic stroke, head trauma, spinal cord injury, hypoxia-induced nerve cell damage as in cardiac arrest or neonatal distress, epilepsy, anxiety, and neurodegenerative disease. Also meant by "neurological disorder or disease" are those disease states and conditions in which a neuroprotectant, anticonvulsant, anxiolytic, analgesic, muscle relaxant and/or adjunct in general anesthesia may be indicated, useful, recommended or prescribed.

By "neurodegenerative disease" is meant diseases including, but not limited to, Alzheimer's Disease, Huntington's Disease, Parkinson's Disease, and amyotrophic lateral sclerosis (ALS).

By "neuroprotectant" is meant a compound capable of preventing the neuronal death associated with a neurological disorder or disease.

By "anticonvulsant" is meant a compound capable of reducing convulsions produced by conditions such as simple partial seizures, complex partial seizures, status epilepticus, and trauma-induced seizures such as occur following head injury, including head surgery.

By "anxiolytic" is means a compound capable of relieving the feelings of apprehension, uncertainty and fear that are characteristic of anxiety.

By "analgesic" is meant a compound capable of relieving pain by altering perception of nociceptive stimuli without producing anesthesia or loss of consciousness.

By "muscle relaxant" is meant a compound that reduces muscular tension.

By "adjunct in general anesthesia" is meant a compound useful in conjunction with anesthetic agents in producing the loss of ability to perceive pain associated with the loss of consciousness.

In a related aspect the invention features a method for treating a neurological disease or disorder, comprising the step of administering a pharmaceutical composition comprising a compound which binds to a receptor-operated calcium channel at the site bound by one of the arylalkylamines Compound 1, Compound 2 and Compound 3, said compound being a potent and selective noncompetitive antagonist at such a receptor-operated calcium channel, and having one or more of the following pharmacological and physiological properties: efficacy in in vitro biochemical and electrophysiological assays of receptor-operated calcium channel function, in vivo anticonvulsant activity, in vivo neuroprotectant activity, in vivo anxiolytic activity, and in vivo analgesic activity; said compound also possessing one or more of the following pharmacological effects: the compound does not interfere with the induction of long-term potentiation in rat hippocampal slices, and, at a therapeutic dose, does not impair cognition, does not disrupt motor performance, does not produce neuronal vacuolization, has minimal cardiovascular activity, does not produce sedation or hyperexcitability, has minimal PCP-like abuse potential, and has minimal PCP-like psychotomimetic activity. By "minimal" is meant that any side effect of the drug is tolerated by an average individual, and thus that the drug can be used for therapy of the target disease. Such side effects are well known in the art and are routinely regarded by the FDA as minimal when it approves a drug for a target disease.

Treatment involves the steps of first identifying a patient that suffers from a neurological disease or disorder by standard clinical methodology and then treating such a patient with a composition of the present invention.

By "potent" is meant that the compound has at receptor-operated calcium channels, including NMDA receptors, $Ca^{2+}$-permeable AMPA receptors, and nicotinic cholinergic receptors, an $IC_{50}$ value less than 10 $\mu$M, more preferably less than 100 nM, and even more preferably less than 1 nM.

By "selective" is meant that the compound is potent at receptor-operated calcium channels as defined above, but is less potent by greater than 10-fold, more preferably $_{50}$-fold, and even more preferably 100-fold, at other neurotransmitter receptors, neurotransmitter receptor-operated ion channels, or voltage-dependent ion channels.

By "biochemical and electrophysiological assays of receptor-operated calcium channel function" is meant assays designed to detect by biochemical or electrophysiological means the functional activity of receptor-operated calcium channels. Examples of such assays include, but are not limited to, the fura-2 fluorimetric assay for cytosolic calcium in cultured rat cerebellar granule cells (see, Example 1 and Example 2), patch clamp electrophysiological assays (see Example 3 and Example 27), rat hippocampal slice synaptic transmission assays (see Example 5), radioligand binding assays (see Example 4, Example 24, Example 25, and Example 26), and in vitro neuroprotectant assays (see Example 6).

By "efficacy" is meant that a statistically significant level of the desired activity is detectable with a chosen compound; by "significant" is meant a statistical significance at the p<0.05 level.

By "neuroprotectant activity" is meant efficacy in treatment of neurological disorders or diseases including, but not limited to, global and focal ischemic and hemorrhagic stroke, head trauma, spinal cord injury, hypoxia-induced nerve cell damage as in cardiac arrest or neonatal distress, and neurodegenerative diseases such as Alzheimer's Disease, Huntington's Disease, Parkinson's Disease, and amyotrophic lateral sclerosis (ALS) (see Examples 7 and 8, below).

By "anticonvulsant activity" is meant efficacy in reducing convulsions produced by conditions such as simple partial seizures, complex partial seizures, status epilepticus, and trauma-induced seizures such as occur following head injury, including head surgery (see Examples 9 and 10, below).

By "anxiolytic activity" is meant that a compound reduces the feelings of apprehension, uncertainty and fear that are characteristic of anxiety.

By "analgesic activity" is meant that a compound produces the absence of pain in response to a stimulus that would normally be painful. Such activity would be useful in clinical conditions of acute and chronic pain including, but not limited to the following: preemptive preoperative analgesia; peripheral neuropathies such as occur with diabetes mellitus and multiple sclerosis; phantom limb pain; causalgia; neuralgias such as occur with herpes zoster; central pain such as that seen with spinal cord lesions; hyperalgesia; and allodynia. By "causalgia" is meant a painful disorder associated with injury of peripheral nerves. By "neuralgia" is meant pain in the distribution of a nerve or nerves. By "central pain" is meant pain associated with a lesion of the central nervous system. By "hyperalgesia" is meant an increased response to a stimulus that is normally painful. By "allodynia" is meant pain due to a stimulus that does not normally provoke pain (see Examples 11 through 14, below).

By "induction of long term potentiation in rat hippocampal slices" is meant the ability of tetanic electrical stimulation of afferent Schaffer collateral fibers to elicit long-term increases in the strength of synaptic transmission at the Schaffer collateral-CA1 pyramidal cell pathway in rat hippocampal slices maintained in vitro (see Example 19).

By "therapeutic dose" is meant an amount of a compound that relieves to some extent one or more symptoms of the disease or condition of the patient. Additionally, by "therapeutic dose" is meant an amount that returns to normal, either partially or completely, physiological or biochemical parameters associated or causative of the disease or condition. Generally, it is an amount between about 1 nmole and 1 umole of the compound, dependent on its $EC_{50}$ ($IC_{50}$ in the case of an antagonist) and on the age, size, and disease associated with the patient.

By "impair cognition" is meant the ability to impair the acquisition of memory or the performance of a learned task (see Example 20). Also by "impair congnition" is meant the ability to interfere with normal rational thought processes and reasoning.

By "disrupt motor function" is meant the ability to significantly alter locomotor activity (see Example 15) or elicit significant ataxia, loss of the righting reflex, sedation or muscle relaxation (see Example 16).

By "locomotor activity" is meant the ability to perform normal ambulatory movements.

By "loss of the righting reflex" is meant the ability of an animal, typically a rodent, to right itself after being placed in a supine position.

By "neuronal vacuolization" is meant the production of vacuoles in neurons of the cingulate cortex or retrosplenial cortex (see Example 18).

By "cardiovascular activity" is meant the ability to elicit significant changes in parameters including, but not limited to, mean arterial blood pressure and heart rate (see Examples 21 and 22).

By "hyperexcitability" is meant an enhanced susceptibility to an excitatory stimulus. Hyperexcitability is often manifested as a significant increase in locomotor activity in rodents administered a drug (see Example 15).

By "sedation" is meant a calmative effect, or the allaying of activity and excitement. Sedation is often manifested as a significant decrease in locomotor activity in rodents administered a drug (see Example 15).

By "PCP-like abuse potential" is meant the potential of a drug to be wrongfully used, as in the recreational use of PCP (i.e., "angel dust") by man. It is believed that PCP-like abuse potential can be predicted by the ability of a drug to generalize to PCP in rodents trained to discriminate PCP from saline (see Example 17.)

By "generalization to PCP" is meant that a compound is perceived as being PCP in rodents trained to discriminate PCP from saline (see Example 17).

By "PCP-like psychotomimetic activity" is meant the ability of a drug to elicit in man a behavioral syndrome resembling acute psychosis, including visual hallucinations, paranoia, agitation, and confusion. It is believed that PCP-like psychotomimetic activity can be predicted in rodents by the ability of a drug to produce PCP-like stereotypic behaviors including ataxia, head weaving, hyperexcitability, and generalization to PCP in rodents trained to discriminate PCP from saline (see Example 15, Example 16, and Example 17).

By "ataxia" is meant a deficit in muscular coordination.

By "head weaving" is meant the stereotypic behavior elicited in rodents by PCP in which the head is repeatedly moved slowly and broadly from side to side.

In a further aspect, the invention features compounds useful for treating a patient having a neurological disease or disorder wherein said compound is a polyamine-type compound or an analog thereof (i.e., a polyheteroatomic molecule) having the formula

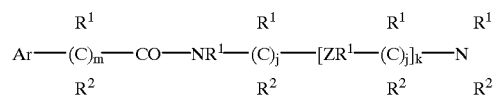

wherein Ar is an appropriately substituted aromatic ring, ring system or other hydrophobic entity; Ar can be an aromatic (e.g., carbocyclic aryl groups such as phenyl and bicyclic carbocyclic aryl ring systems such as naphthyl, 1,2,3,4-tetrahydronaphthyl, indanyl, and indenyl), heteroaromatic (e.g. indolyl, dihydroindolyl, quinolinyl and isoquinolinyl, and their respective 1,2,3, 4-tetrahydro- and 2-oxo- derivatives), alicyclic (cycloaliphatic), or heteroalicyclic ring or ring system (mono-, bi-, or tricyclic), having 5- to 7-membered ring(s) optionally substituted with 1 to 5 substituents independently selected from lower alkyl of 1 to 5 carbon atoms, lower haloalkyl of 1 to 5 carbon atoms substituted with 1 to 7 halogen atoms, lower alkoxy of 1 to 5 carbon atoms, halogen, nitro, amino, lower alkylamino of 1 to 5 carbon atoms, amido, lower alkylamido of 1 to 5 carbon atoms, cyano, hydroxyl, sulfhydryl, lower acyl of 2 to 4 carbon atoms, sulfonamido, lower alkylsulfonamido of 1 to 5 carbon atoms, lower alkylsulfoxide of 1 to 5 carbon atoms, lower hydroxyalkyl of 1 to 5 carbon atoms, lower alkylketo of 1 to 5 carbon atoms, or lower thioalkyl of 1 to 5 carbon atoms, each m is an integer from 0 to 3, inclusive, eack k is an integer from 1 to 10, inclusive, each j is the same or different and is an integer from 1 to 12, inclusive, each $R^1$ and $R^2$ independently is selected from the group consisting of hydrogen, lower alkyl of 1 to 5 carbon atoms, lower alkylamino of 1 to 5 carbon atoms, lower alkylamido of 1 to 5 carbon atoms, lower mono-, di-, or trifluoroalkyl of 1 to 5 carbon atoms, hydroxy, amidino, guanidino, or typical common amino acid side chain or with an associated carbon atom $R^1$ and $R^2$ taken together form a carbonyl, and each Z is selected from the group consisting of nitrogen, oxygen, sulfur, amido, sulfonamido, and carbon.

Especially preferred are those embodiments in which the terminal —$NR^1R^2$ group is N-ethyl ($R^1$=H, $R^2$=$CH_2CH_3$), as these compounds are associated with a greatly reduced incidence and severity of undesirable cardiovascular side effects, such as hypotension.

Preferred aromatic headgroups include, but are not limited to, the following:

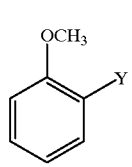

Headgroup A

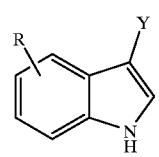

Headgroup B

Headgroup C

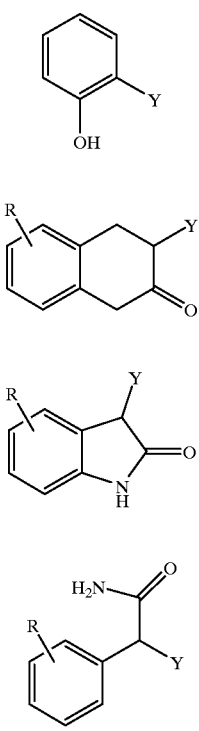

Headgroup D

Headgroup E

Headgroup F

Headgroup G

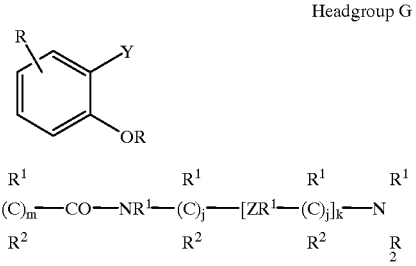

where Y=
$$Ar-(C)_m\overset{R^1}{\underset{R^2}{|}}-CO-NR^1-(C)_j\overset{R^1}{\underset{R^2}{|}}-[ZR^1-(C)_j]_k\overset{R^1}{\underset{R^2}{|}}-N\overset{R^1}{\underset{R_2}{|}}$$

Excluded from the present invention are known compounds whose chemical structures are covered by the generic formula presented above.

In further preferred embodiments, the compound is selected from the group of Compounds 4 through 18, where such compounds have the formulae:

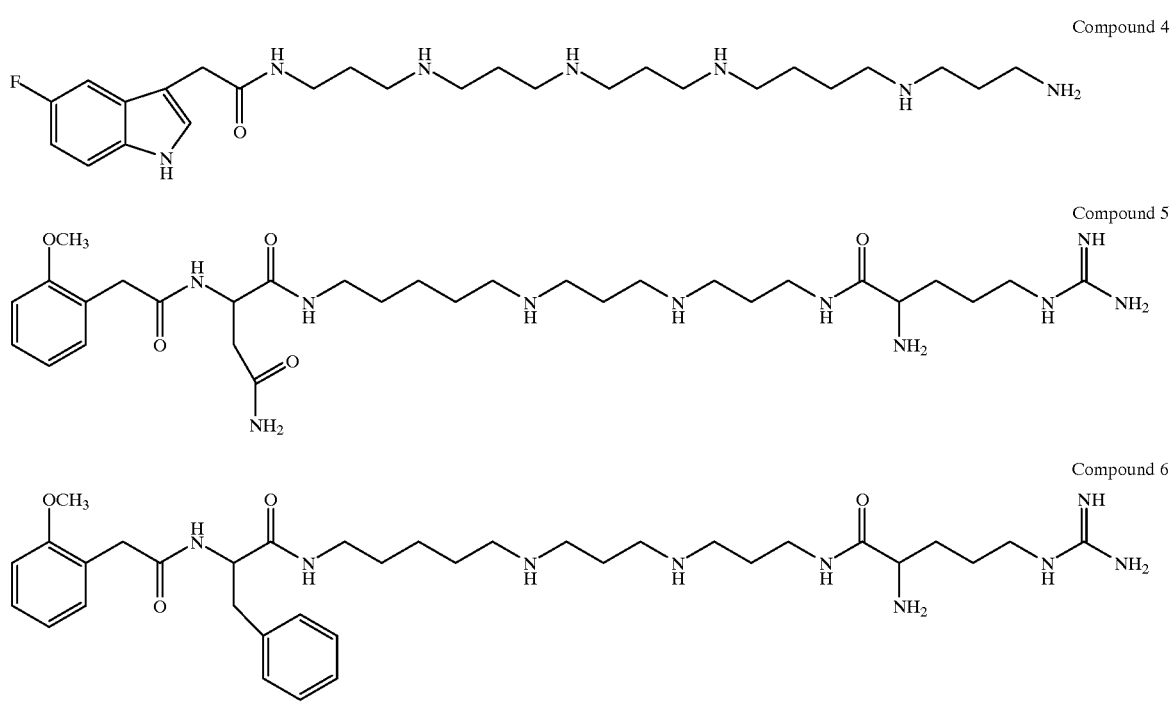

-continued
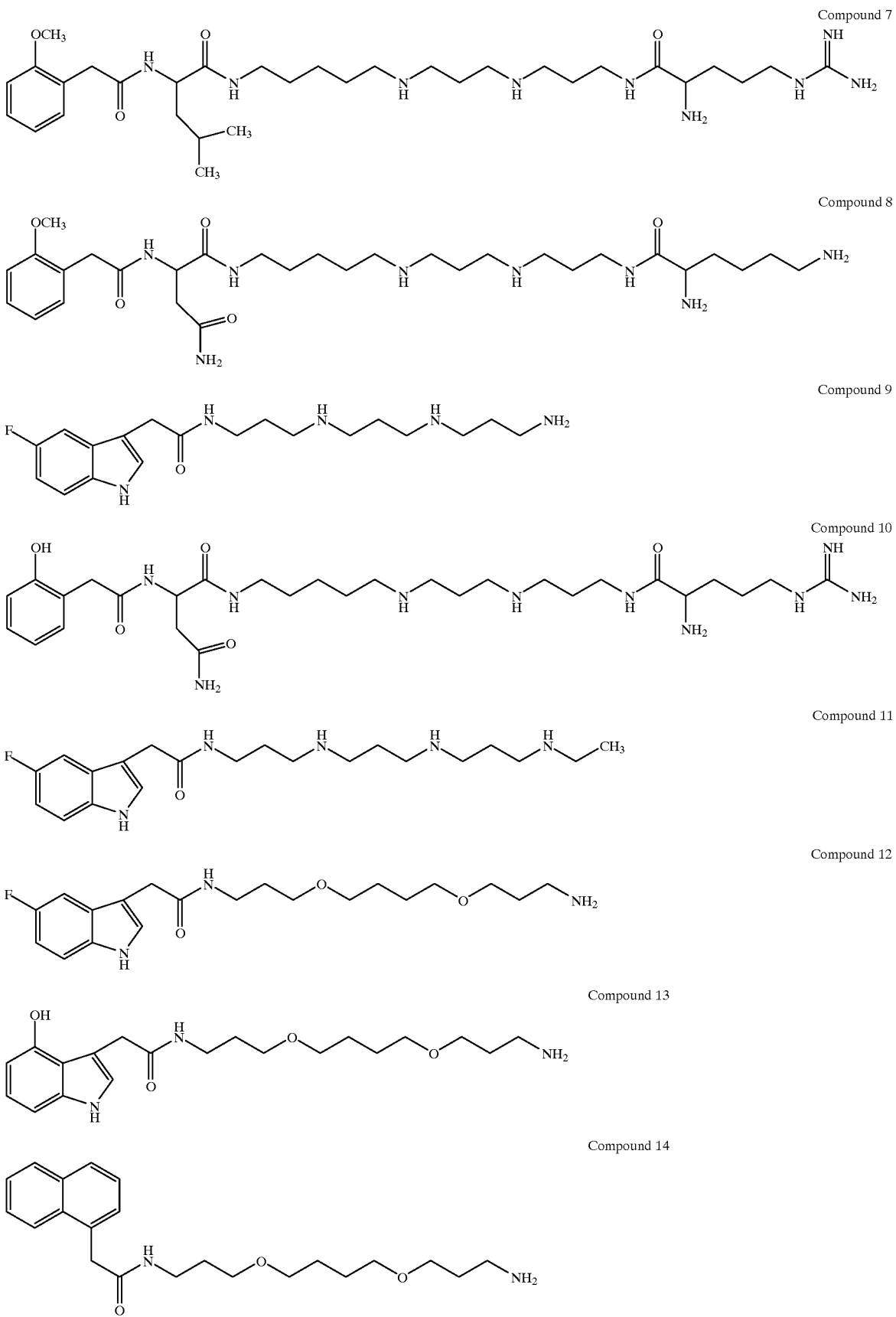

-continued

Compound 15

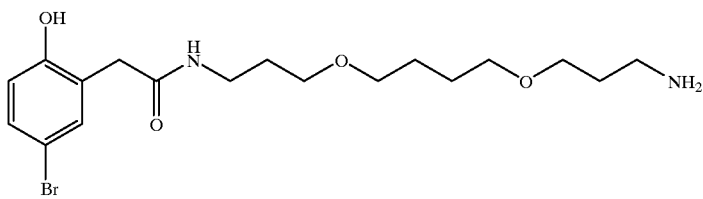

Compound 16

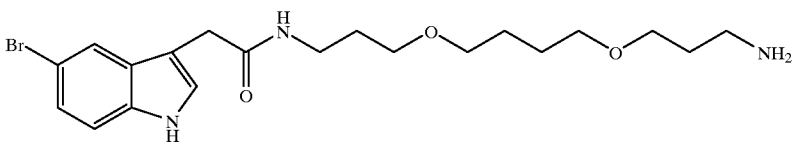

Compound 17

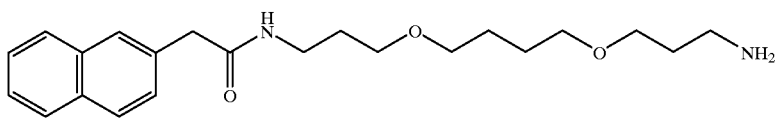

Compound 18

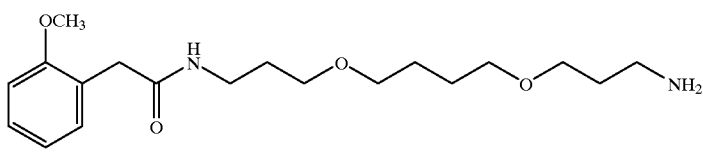

The invention also features compositions of the various compounds of the invention, including Compounds 4–18, or pharmaceutically acceptable salts thereof and pharmaceutical compositions or pharmaceutically acceptable salts thereof in a pharmaceutically acceptable carrier and dose.

By "pharmaceutical composition" is meant a therapeutically effective amount of a compound of the present invention in a pharmaceutically acceptable carrier, i.e., a formulation to which the compound can be added to dissolve or otherwise facilitate administration of the compound. Examples of pharmaceutically acceptable carriers include water, saline, and physiologically buffered saline. Such a pharmaceutical composition is provided in a suitable dose. Such compositions are generally those which are approved for use in treatment of a specified disorder by the FDA or its equivalent in non-U.S. countries.

Applicant has also determined (see Example 23 below) that simplified arylalkylamines (see below) are potent, non-competitive antagonists of the NMDA receptor-ionophore complex. The simplified arylalkylamines are distinct from the arylalkylamines exemplified by Compounds 4–18 as described above. For example, such compounds bind to the site labeled by [$^3$H]MK-801 at concentrations ranging approximately 1 to 400-fold higher than those which antagonize NMDA receptor-mediated function. Such simplified arylalkylamines possess one or more of the following additional biological properties: significant neuroprotectant activity, significant anticonvulsant activity, significant analgesic activity, no PCP-like stereotypic behavior in rodents (hyperexcitability and head weaving) at effective neuroprotectant, anticonvulsant and analgesic doses, no generalization to PCP in a PCP discrimination assay at effective neuroprotectant, anticonvulsant and analgesic doses, no neuronal vacuolization at effective neuroprotectant, anticonvulsant and analgesic doses, significantly less potent activity against voltage-sensitive calcium channels, and minimal hypotensive activity at effective neuroprotectant, anticonvulsant and analgesic doses. Such compounds may, however, inhibit the induction of LTP in rat hippocampal slices and may produce motor impairment at neuroprotectant, anticonvulsant and analgesic doses.

One aspect of the invention features a method for treating a patient having a neurological disease or disorder, comprising administering the compounds of Formula I:

FORMULA I

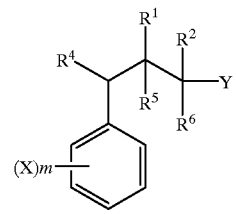

wherein:

$R^1$ and $R^5$ are independently selected from the group consisting of —H, alkyl, hydroxyalkyl, —OH, —O-alkyl, and —O-acyl;

$R^2$ and $R^6$ are independently selected from the group consisting of —H, alkyl, and hydroxyalkyl; or $R^1$ and $R^2$ together are —(CH$_2$)$_n$— or —(CH$_2$)$_n$—N(R$^3$)—;

$R^3$ is independently selected from the group consisting of —H, alkyl and 2-hydroxyethyl;

n is an integer from 1 to 6;

$R^4$ is selected from the group consisting of alkyl, cycloalkyl, and

X is independently selected from the group consisting of —H, —Br, —Cl, —F, —CF$_3$, alkyl, —OH, —OCH$_3$, —O-alkyl, and —O-acyl;

m is independently an integer from 0 to 5;

Y is —NR$^3$R$^3$, except when R$^1$ and R$^2$ together are —(CH$_2$)n—N(R$^3$)—, then Y is —H; and pharmaceutically acceptable salts thereof.

By "alkyl" is meant branched or unbranched hydrocarbon chains containing between 1 and 6, preferably between 1 and 4 carbon atoms, such as, e.g., methyl, ethyl, n-propyl, iso-propyl, n-butyl, sec-butyl, iso-butyl, tert-butyl, 2-methylpentyl, cyclopropylmethyl, allyl, and cyclobutylmethyl. By "lower alkyl" is meant branched or unbranched hydrocarbon chains containing between 1 and 4 carbon atoms, of which examples are listed herein.

By "hydroxyalkyl" is meant an alkyl group as defined above, substituted with a hydroxyl group.

By "acyl" is meant —C(O)R, where R is alkyl as defined above, such as, e.g., formyl, acetyl, propionyl, or butyryl; or R is —O-alkyl such as alkyl carbonates or R is N-alkyl such as alkyl carbamates.

By "cycloalkyl" is meant a cyclic hydrocarbon chain containing between 3 and 7 carbon atoms.

In preferred aspects of the invention,

Y is NR$^3$R$^3$;

NR$^3$R$^3$ is selected from the group consisting of —NH$_2$ and —NH-methyl;

R$^4$ is;

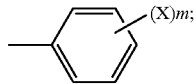

(X)m is independently selected from the group consisting of meta-fluoro, meta-chloro, ortho-methoxy, and ortho-methyl and;

R$^1$ is methyl, and R$^2$, R$^5$, and R$^6$ are —H; or R$^2$ is methyl, and R$^1$, R$^5$, and R$^6$ are H; or R$^1$, R$^2$, R$^5$ and R$^6$ are —H.

In other preferred aspects of the present invention,

R$^1$ and R$^5$ are independently selected from the group consisting of —H, lower alkyl, hydroxyalkyl, —OH, —O-alkyl, and —O-acyl;

R$^2$ and R$^6$ are independently selected from the group consisting of —H, lower alkyl, and hydroxyalkyl; or R$^1$ and R$^2$ together are —(CH$_2$)$_n$— or —(CH$_2$)$_n$—N(R$^3$)—;

R$^3$ is independently selected from the group consisting of —H and lower alkyl;

n is an integer from 1 to 6;

R$^4$ is selected from the group consisting of —H, lower alkyl, cycloalkyl, and

X is independently selected from the group consisting of —H, —Br, —Cl, —F, —CF$_3$, lower alkyl, —OH, and —OCH$_3$;

m is independently an integer from 0 to 5;

Y is —NR$^3$R$^3$, or hydrogen;

and pharmaceutically acceptable salts thereof, with the provisos that (a) when R$^1$ and R$^2$ together are —(CH$_2$)$_n$—N(R$^3$)—, then R$^5$, R$^6$, and Y are hydrogens; and (b) when R$^1$ and R$^2$ together are not —(CH$_2$)$_n$—N(R$^3$)—, then Y is —NR$^3$R$^3$.

In a further aspect, the invention features a method for treating a patient having a neurological disease or disorder comprising administering a the compounds of Formula II:

Formula II

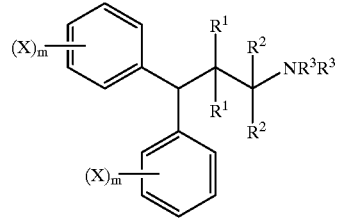

wherein X is independently selected from the group consisting of —H, —Br, —Cl, —F, —CF$_3$, alkyl, —OH, —OCH$_3$, —O-alkyl, and —O-acyl; R$^1$ is independently selected from the group consisting of —H, alkyl, hydroxyalkyl, —OH, —O-alkyl, and —O-acyl; R$^2$ is independently selected from the group consisting of —H, alkyl, and hydroxyalkyl; R$^3$ is independently selected from the group consisting of —H and alkyl; and m is independently an integer from 0 to 5; or the compounds of Formula III:

Formula III

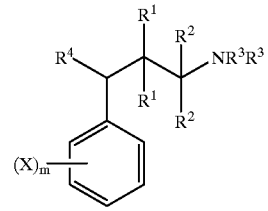

wherein X is independently selected from the group consisting of —H, —Br, —Cl, —F, —CF$_3$, alkyl, —OH, —OCH$_3$ —O-alkyl, and —O-acyl; R$^1$ is independently selected from the group consisting of —H, alkyl, hydroxyalkyl, —OH, —O-alkyl, and —O-acyl; R$^2$ is independently selected from the group consisting of —H, alkyl, and hydroxyalkyl; R$^3$ is independently selected from the group consisting of —H and alkyl; R$^4$ is selected from the group consisting of alkyl and cycloalkyl, and m is independently an integer from 0 to 5; or the compounds of Formulas IV and V.

Formula IV

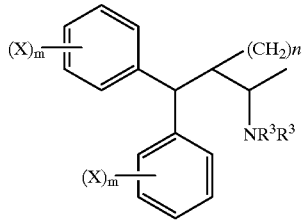

Formula V

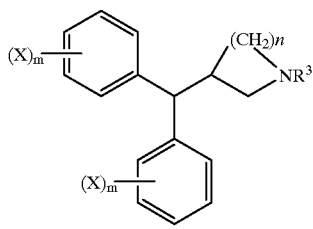

wherein n is an integer from 1 to 6; X is independently selected from the group consisting of —H, —Br, —Cl, —F, —CF$_3$, alkyl, —OH, —OCH$_3$, —O-alkyl, and —O-acyl; R$^3$ is independently selected from the group consisting of —H and alkyl; and m is independently an integer from 0 to 5; or the compounds of Formula VI and VII:

Formula VI

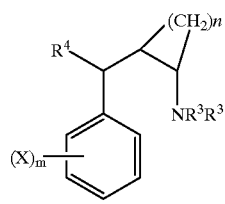

Formula VII

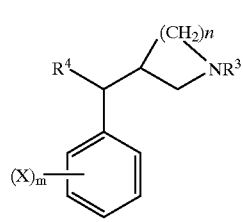

wherein n is an integer from 1 to 6; X is independently selected from the group consisting of —H, —Br, —Cl, —F, —CF$_3$, alkyl, —OH, —OCH$_3$, —O-alkyl, and —O-acyl; R$^3$ is independently selected from the group consisting of —H and alkyl; R$^4$ is selected from the group consisting of alkyl and cycloalkyl, and m is independently an integer from 0 to 5.

More preferred are those embodiments in which (X)$_m$ is independently selected from the group consisting of meta-fluoro, meta-chloro, ortho-methoxy, and ortho-methyl; NR$^3$ is selected from the group consisting of NH, N-methyl, and N-ethyl; NR$^3$R$^3$ is selected from the group consisting of NH$_2$, NH-methyl, and NH-ethyl; R$^1$ is selected from the group consisting of —H and methyl; and R$^2$ is selected from the group consisting of —H and methyl.

Especially preferred are those embodiments in which (X)m is meta-fluoro; NR$^3$ is selected from the group consisting of NH and N-methyl; and NR$^3$R$^3$ is selected from the group consisting of NH$_2$ and NH-methyl.

In other preferred embodiments is provided a method for treating a patient having a neurological disease or disorder, comprising administering the compounds of Formulas I–VII, wherein X is independently selected from the group consisting of —CF$_3$, and alkyl; R$^1$ is hydroxyalkyl; R$^2$ is hydroxyalkyl; R$^3$ is independently selected from the group consisting of —H, and alkyl; R$^4$ is selected from the group consisting of —H, alkyl, cycloalkyl, and

and m is independently an integer from 0 to 5.

Excluded from the present invention are known compounds whose chemical structures are covered by the generic formulae presented above.

In preferred embodiments, the methods of treatment include administration of a compound selected from Compounds 19 through 69, or pharmaceutically acceptable salts thereof.

In further preferred embodiments, the methods of treatment include administration of a compound selected from the group consisting of Compound 20, 21, 22, 23, 24, 25, 27, 28, 29, 30, 31, 32, 33, 34, 38, 39, 40, 41, 42, 43, 44, 45, 46, 47, 48, 49, 50, 51, 52, 53, 54, 55, 56, 57, 58, 59, 60, 61, 62, 63, 64, 65, 66 and 69.

In more preferred embodiments, the methods of treatment include administration of a compound selected from the group consisting of Compound 20, 24, 27, 30, 31, 33, 34, 46, 47, 48, 50, 57, 58, 60, 61, 62, 65, 66, and 69.

In particularly preferred embodiments, the compound is selected from a group consisting of Compound 20, 50, 60, and one of the enantiomers of Compound 21 (Compound 33 or 34).

In other preferred embodiments, the methods of treatment include administration of a compound selected from the group consisting of Compound 54, 55, 56, 57, 58, 59, 60, 61, 62, 63, 64, 65, 66, 67, 68, and 69.

Also provided in an aspect of the invention are pharmaceutical compositions useful for treating a patient having a neurological disease or disorder. The pharmaceutical compositions are provided in a pharmaceutically acceptable carrier and appropriate dose.

The pharmaceutical compositions comprise the compounds of Formula I:

Formula I

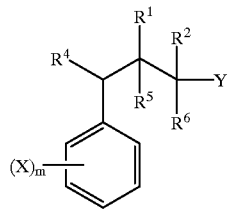

wherein:

R$^1$ and R$^5$ are independently selected from the group consisting of —H, alkyl, hydroxyalkyl, —OH, —O-alkyl, and —O-acyl;

R$^2$ and R$^6$ are independently selected from the group consisting of —H, alkyl, and 2-hydroxyethyl; or R$^1$ and R$^2$ together are —(CH$_2$)$_n$— or —(CH$_2$)$_n$—N(R$^3$)—;

R$^3$ is independently selected from the group consisting of —H, alkyl and 2-hydroxyethyl;

n is an integer from 1 to 6;

R$^4$ is selected from the group consisting of alkyl, cycloalkyl, and

X is independently selected from the group consisting of —H, —Br, —Cl, —F, —CF$_3$, alkyl, —OH, —OCH$_3$, —O-alkyl, and —O-acyl;

m is independently an integer from 0 to 5;

Y is —NR$^3$R$^3$, except when R$^1$ and R$^2$ together are —(CH$_2$)$_n$—N(R$^3$)—, then Y is —H; and pharmaceutically acceptable salts thereof.

In preferred aspects of the invention

Y is NR$^3$R$^3$;

NR$^3$R$^3$ is selected from the group consisting of —NH$_2$ and —NH-methyl;

R$^4$ is;

(X)m is independently selected from the group consisting of meta-fluoro, meta-chloro, ortho-methoxy, and ortho-methyl and;

R$^1$ is methyl, and R$^2$, R$^5$, and R$^6$ are —H; or R$^2$ is methyl, and R$^1$, R$^5$, and R$^6$ are H; or R$^1$, R$^2$, R$^5$ and R$^6$ are —H.

In other preferred aspects of the present invention,

R$^1$ and R$^5$ are independently selected from the group consisting of —H, lower alkyl, hydroxyalkyl, —OH, —O-alkyl, and —O-acyl;

R$^2$ and R$^6$ are independently selected from the group consisting of —H, lower alkyl, and hydroxyalkyl; or R$^1$ and R$^2$ together are —(CH$_2$)$_n$— or —(CH$_2$)$_n$—N(R$^3$)—;

R$^3$ is independently selected from the group consisting of —H and lower alkyl;

n is an integer from 1 to 6;

R$^4$ is selected from the group consisting of —H, lower alkyl, cycloalkyl, and

X is independently selected from the group consisting of —H, —Br, —Cl, —F, —CF$_3$, lower alkyl, —OH, and —OCH$_3$;

m is independently an integer from 0 to 5;

Y is —NR$^3$R$^3$, or hydrogen;

and pharmaceutically acceptable salts thereof, with the provisos that (a) when R$^1$ and R$^2$ together are —(CH$_2$)$_n$—N(R$^3$)—, then R$^5$, R$^6$, and Y are hydrogens; and (b) when R$^1$ and R$^2$ together are not —(CH$_2$)$_n$—N(R$^3$)—, then Y is —NR$^3$R$^3$.

In a further aspect, the invention features pharmaceutical compositions comprising the compounds of Formula II:

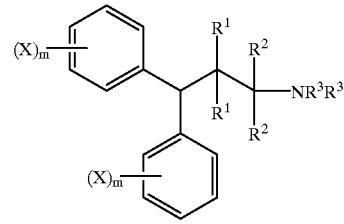

Formula II wherein X is independently selected from the group consisting of —H, —Br, —Cl, —F, —CF$_3$, alkyl, —OH, —OCH$_3$, —O-alkyl, and —O-acyl; R$^1$ is independently selected from the group consisting of —H, alkyl, hydroxyalkyl, —OH, —O-alkyl, and —O-acyl; R$^2$ is independently selected from the group consisting of —H, alkyl, and hydroxyalkyl; R$^3$ is independently selected from the group consisting of —H and alkyl; and m is independently an integer from 0 to 5; or the compounds of Formula III:

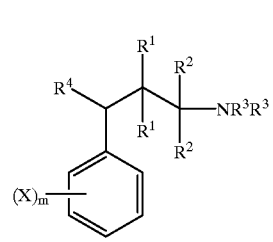

Formula III wherein X is independently selected from the group consisting of —H, —Br, —Cl, —F, —CF$_3$, alkyl, —OH, —OCH$_3$ —O-alkyl, and —O-acyl; R$^1$ is independently selected from the group consisting of —H, alkyl, hydroxyalkyl, —OH, —O-alkyl, and —O-acyl; R$^2$ is independently selected from the group consisting of —H, alkyl, and hydroxyalkyl; R$^3$ is independently selected from the group consisting of —H and alkyl; R$^4$ is selected from the group consisting of alkyl and cycloalkyl, and m is independently an integer from 0 to 5; or the compounds of Formulas IV and V.

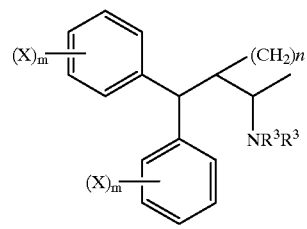

Formula IV

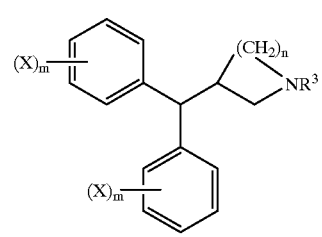

Formula V wherein n is an integer from 1 to 6; X is independently selected from the group consisting of —H, —Br, —Cl, —F, —CF$_3$, alkyl, —OH, —OCH$_3$, —O-alkyl, and —O-acyl; R$^3$ is independently selected from the group consisting of —H and alkyl; and m is independently an integer from 0 to 5; or the compounds of Formula VI and VII:

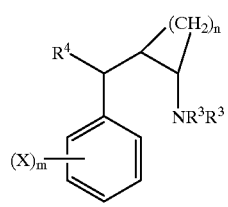

Formula VI

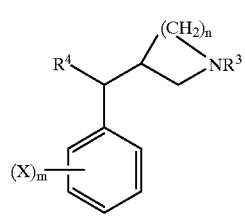

Formula VII wherein n is an integer from 1 to 6; X is independently selected from the group consisting of —H, —Br, —Cl, —F, —CF$_3$, alkyl, —OH, —OCH$_3$, —O-alkyl, and —O-acyl; R$^3$ is independently selected from the group consisting of —H and alkyl; R$^4$ is selected from the group consisting of alkyl and cycloalkyl, and m is independently an integer from 0 to 5.

More preferred are those embodiments in which (X)$_m$ is independently selected from the group consisting of meta-fluoro, meta-chloro, ortho-methoxy, and ortho-methyl; NR$^3$ is selected from the group consisting of NH, N-methyl, and N-ethyl; NR$^3$R$^3$ is selected from the group consisting of NH$_2$, NH-methyl, and NH-ethyl; R$^1$ is selected from the group consisting of —H and methyl; and R$^2$ is selected from the group consisting of —H and methyl.

Especially preferred are those embodiments in which (X)m is meta-fluoro; NR$^3$ is selected from the group consisting of NH and N-methyl; and NR$^3$R$^3$ is selected from the group consisting of NH$_2$ and NH-methyl.

In further preferred embodiments, X is independently selected from the group consisting of —CF$_3$, and alkyl; R$^1$ is hydroxyalkyl; R$^2$ is hydroxyalkyl; R$^3$ is independently selected from the group consisting of —H, and alkyl; R$^4$ is selected from the group consisting of —H, alkyl, cycloalkyl, and

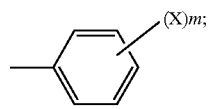

and m is independently an integer from 0 to 5.

Preferred pharmaceutical compositions comprise Compounds 19–69.

In further preferred embodiments, the pharmaceutical composition comprises a compound selected from the group consisting of Compound 20, 21, 22, 23, 24, 25, 27, 28, 29, 30, 31, 32, 33, 34, 38, 39, 40, 41, 42, 43, 44, 45, 46, 47, 48, 49, 50, 51, 52, 53, 54, 55, 56, 57, 58, 59, 60, 61, 62, 63, 64, 65, 66, and 69.

In more preferred embodiments, the pharmaceutical composition comprises a compound selected from the group consisting of Compound 20, 24, 27, 30, 31, 33, 34, 46, 47, 48, 50, 57, 58, 60, 61, 62, 65, 66, and 69.

In particularly preferred embodiments, the pharmaceutical compositions comprises a compound selected from the group consisting of Compound 20, 50, 60, and one of the enantiomers of Compound 21 (Compound 33 or 34).

In other preferred embodiments, the pharmaceutical composition comprises a compound selected from the group consisting of Compound 54, 55, 56, 57, 58, 59, 60, 61, 62, 63, 64, 65, 66, 67, 68, and 69.

Compound 19

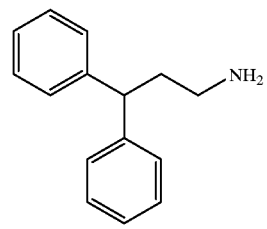

Compound 20

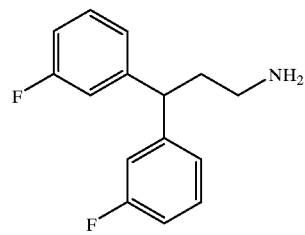

Compound 21

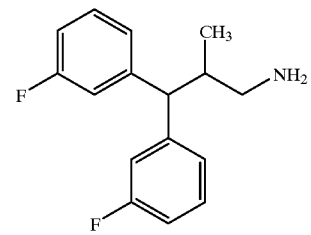

Compound 22

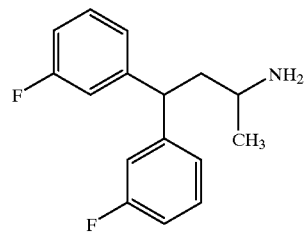

Compound 23

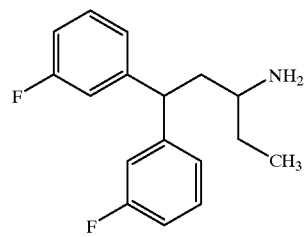

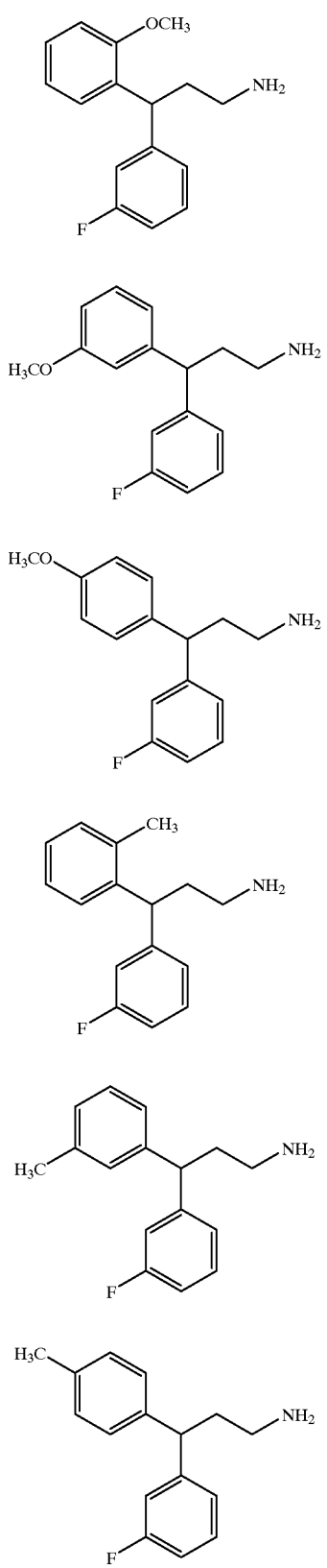
Compound 24
Compound 25
Compound 26
Compound 27
Compound 28
Compound 29
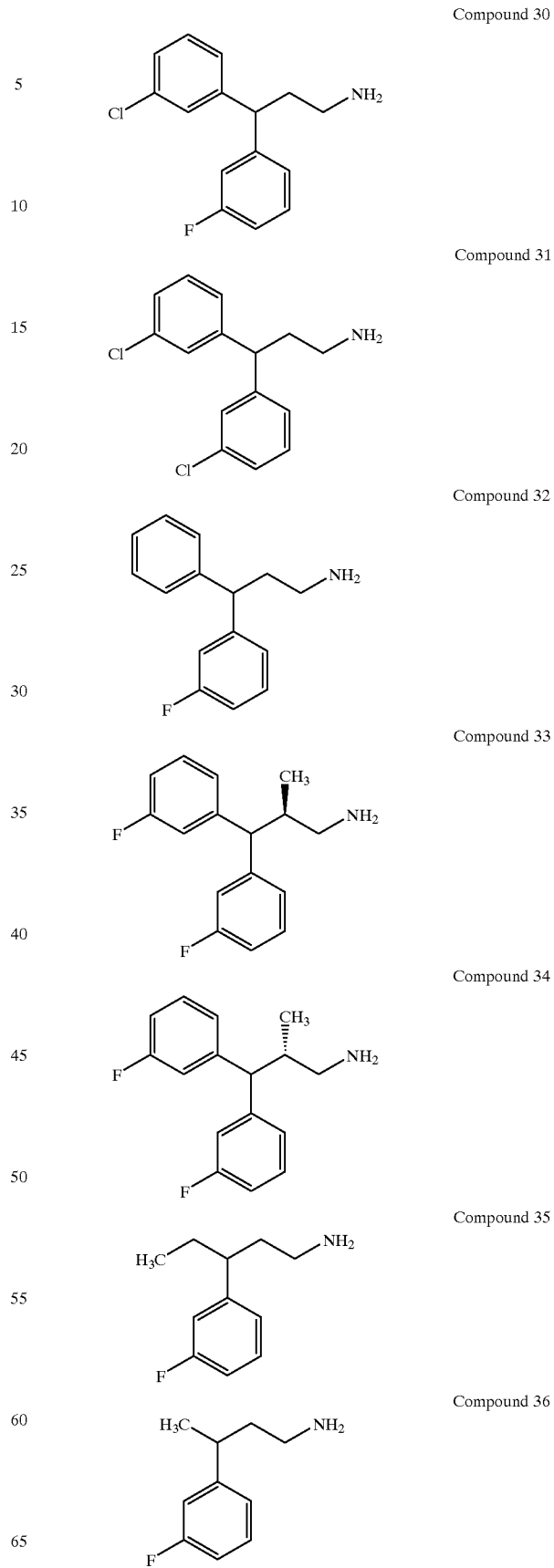
Compound 30
Compound 31
Compound 32
Compound 33
Compound 34
Compound 35
Compound 36

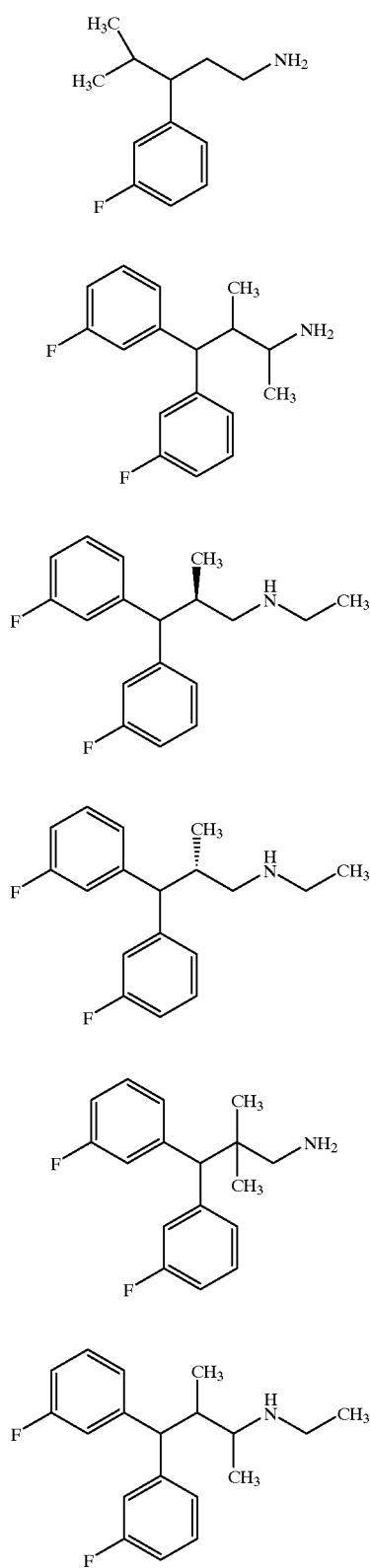

Compound 49
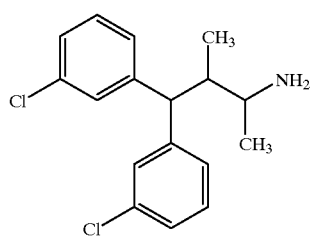
Compound 55
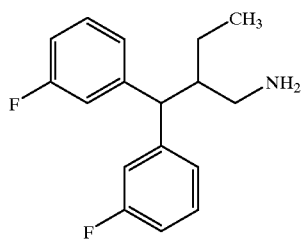
Compound 50
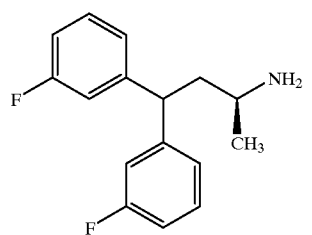
Compound 56
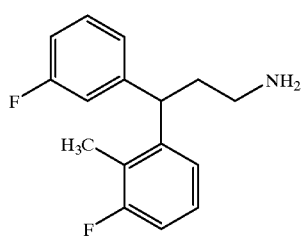
Compound 51
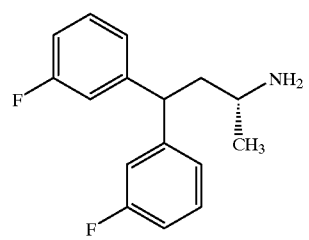
Compound 57
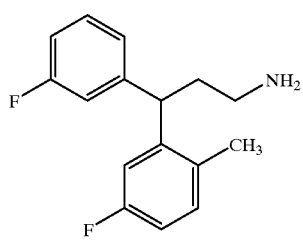
Compound 52
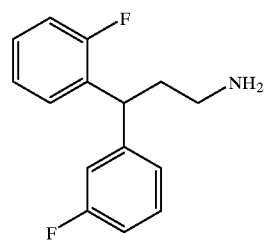
Compound 58
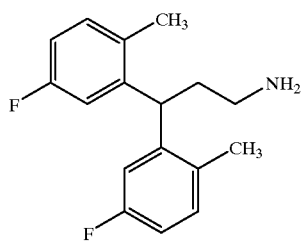
Compound 53
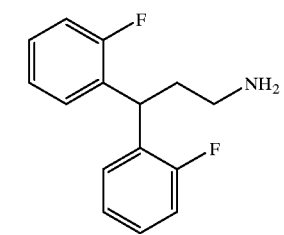
Compound 59
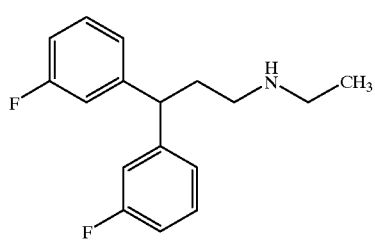
Compound 54
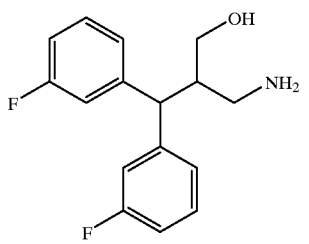
Compound 60
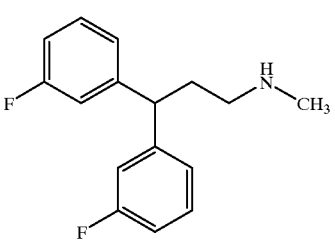

Compound 61
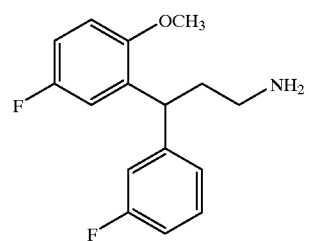

Compound 62
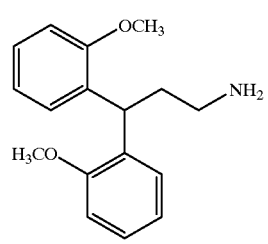

Compound 63
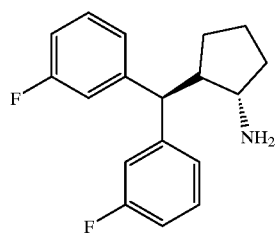

Compound 64
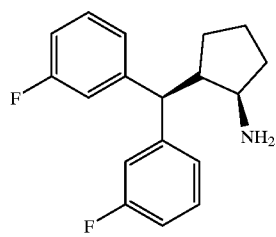

Compound 65
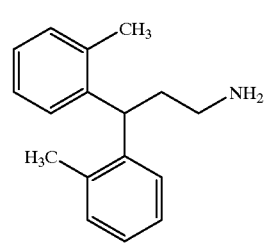

Compound 66
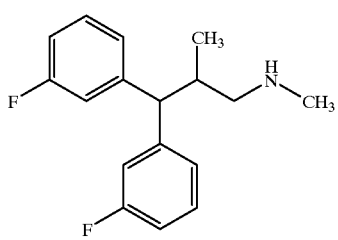

Compound 67
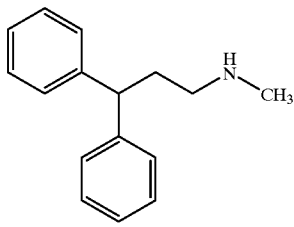

Compound 68
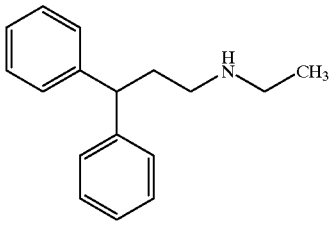

Compound 69
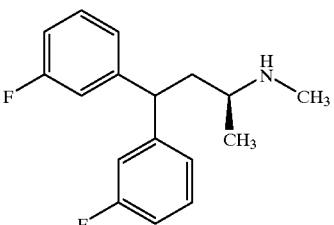

Other features and advantages of the invention will be apparent from the following description of the preferred embodiments thereof, and from the claims.

DESCRIPTION OF THE PREFERRED EMBODIMENTS

The following is a detailed description of the methods and tests by which therapeutically useful compounds can be identified and utilized for treatment of neurological disorders and diseases. The tests are exemplified by use of Compound 1, Compound 2 or Compound 3, but other compounds which have similar biological activity in these assays can also be used (as discovered) to improve on the tests. Lead compounds such as Compound 1, Compound 2 or Compound 3 can be used for molecular modeling using standard procedures, or existing or novel compounds in natural libraries can be screened by the methods described below.

One key method is the means by which compounds can be quickly screened with standard radioligand binding techniques (a radiolabeled arylalkylamine binding assay) to identify those which bind at the same site on receptor-operated $Ca^{2+}$ channels as Compound 1, Compound 2 or Compound 3. Data from such radioligand binding studies will also confirm that said compounds do not inhibit $[^3H]$ arylalkylamine binding via an action at the known sites on receptor-operated $Ca^{2+}$ channels (such as the glutamate binding site, glycine binding site, MK-801 binding site, $Zn^{2+}$ binding site, $Mg^{2+}$ binding site, sigma binding site, or polyamine binding site on the NMDA receptor-ionophore complex). This screening test allows vast numbers of potentially useful compounds to be identified and screened for activity in the other assays. Those skilled in the art will recognize that other rapid assays for detection of binding to the arylalkylamine site on receptor-operated $Ca^{2+}$ channels can be devised, and used in this invention.

Additional testing utilizes electrophysiological (patch clamp) methodology to extend the results obtained with the above-mentioned radioligand binding assay. Such results will confirm that compounds binding to the arylalkylamine site are functional, noncompetitive antagonists of receptor-operated $Ca^{2+}$ channels with the following properties in common with the arylalkylamines themselves: open-channel block manifested as use-dependent block, and voltage-dependent onset and reversal from block. Such results will also confirm that said compounds do not have their primary activity at the previously described sites on receptor-operated $Ca^{2+}$ channels (such as the glutamate binding site, glycine binding site, MK-801 binding site, $Zn^{2+}$ binding site, $Mg^{2+}$ binding site, sigma binding site, or polyamine binding site on the NMDA receptor-ionophore complex).

In addition, recombinant DNA technology can be used to make such testing even more rapid. For example, using standard procedures, the gene(s) encoding the novel arylalkylamine binding site (i.e., receptor) can be identified and cloned. This can be accomplished in one of several ways. For example, an arylalkylamine affinity column can be prepared, and solubilized membranes from cells or tissues containing the arylalkylamine receptor passed over the column. The receptor molecules bind to the column and are thus isolated. Partial amino acid sequence information is then obtained which allows for the isolation of the gene encoding the receptor. Alternatively, cDNA expression libraries are prepared and subfractions of the library are tested for their ability to impart arylalkylamine receptors on cells which do not normally express such receptors (e.g., CHO cells, mouse L cells, HEK 293 cells, or Xenopus oocytes). In this way, the library fraction containing the clone encoding the receptor is identified. Sequential subfractionation of active library fractions and assay eventually results in a single clone encoding the arylalkylamine receptor. Similarly, hybrid-arrest or hybrid-depletion cloning can be used. Xenopus oocytes are injected with mRNA from an appropriate tissue or cell source (e.g., human brain tissue). Expression of the arylalkylamine receptor is detected as, for example, an NMDA- or glutamate-stimulated influx of calcium which can be blocked by Compound 1, Compound 2 or Compound 3. cDNA clones are tested for their ability to block expression of this receptor when cDNA or cRNA are hybridized to the mRNA of choice, prior to injection into Xenopus oocytes. The clone responsible for this effect is then isolated by the process described above. Once the receptor gene is isolated, standard techniques are used to identify the polypeptide or portion(s) thereof which is (are) sufficient for binding arylalkylamines (the arylalkylamine binding domain[s]). Further, using standard procedures, the entire receptor or arylalkylamine binding domain(s) can be expressed by recombinant technology. Said receptor or binding domain(s) can be isolated and used as a biochemical reagent such that, rather than using a competitive assay exemplified below, a simple direct binding assay can be used. That is, a screen is set up for compounds which bind at the novel arylalkylamine receptor. In this way large numbers of compounds can be simultaneously screened, e.g., by passage through a column containing the novel arylalkylamine receptor or arylalkylamine binding domain, and analysis performed on compounds which bind to the column.

Additional testing utilizes the combination of molecular biological techniques (expression of cloned NMDA, AMPA or nicotinic cholinergic receptors) and patch clamp electrophysiological techniques. Specifically, arylalkylamine analogs can be rapidly screened for potency at cloned and expressed subunits of the above-mentioned receptor-ionophore complexes. Site-directed mutagenesis can be utilized in an effort to identify which amino acid residues may be important in determining arylalkylamine potency.

Assays for Potent and Selective Antagonists of Receptor-Operated Calcium Channels in the Mammalian CNS Desired properties of a drug include: high affinity and selectivity for receptor-operated $Ca^{2+}$ channels, such as those present in NMDA, AMPA and nicotinic cholinergic receptor-ionophore complexes (compared to responses mediated via other neurotransmitter receptors, neurotransmitter receptor-operated ion channels, or voltage-dependent ion channels) and a noncompetitive antagonism of said receptor-operated $Ca^{2+}$ channels.

The NMDA receptor-ionophore complex is utilized as an example of a receptor-operated $Ca^{2+}$ channel. Activation of the NMDA receptor opens a cation-selective channel that allows the influx of extracellular $Ca^{2+}$ and $Na^+$, resulting in increases in $[Ca^{2+}]_i$ and depolarization of the cell membrane. Measurements of $[Ca^{2+}]_i$ were used as primary assays for detecting the activity of arylalkylamine compounds on NMDA receptors. Purified arylalkylamines, synthetic arylalkylamines, and synthetic analogs of arylalkylamines were examined for activity in in vitro assays capable of measuring glutamate receptor activity. Selected for detailed study were the arylalkylamines present in the venom of various spider species. The arylalkylamines present in these venoms are structurally distinct but have the basic structure of the class represented by Compounds 1 through 3. Other more simplified synthetic analogs generally consist of suitably substituted aromatic chromophoric groups attached to an alkyl (poly)amine moiety (see Compounds 19 through 69 below).

A primary assay that provides a functional index of glutamate receptor activity and that allows high-throughput screening was developed. Primary cultures of rat cerebellar granule cells loaded with the fluorimetric indicator fura-2 were used to measure changes in $[Ca^{2+}]_i$ elicited by NMDA and its coagonist glycine. This assay provides an extremely sensitive and precise index of NMDA receptor activity. Increases in $[Ca^{2+}]_i$ evoked by NMDA are dependent on the presence of glycine, and are blocked by extracellular $Mg^{2+}$ or antagonists acting at the glutamate, glycine, or MK-801 binding sites. Increases in $[Ca^{2+}]_i$ elicited by NMDA/glycine are readily distinguished from those resulting from depolarization by their refractoriness to inhibition by blockers of voltage-sensitive $Ca^{2+}$ channels. The fidelity with which measurements of $[Ca^{2+}]_i$ corroborate results obtained by electrophysiological and ligand-binding studies suggests that such measurements mirror closely activation of the NMDA receptor-ionophore complex.

EXAMPLE 1

Potent Noncompetitive Inhibition of NMDA Receptor Function

Preferential inhibitory effects of arylalkylamines on NMDA receptor-mediated increases in $[Ca^{2+}]_i$ in cultured rat cerebellar granule cells were measured. Increases in $[Ca^{2+}]_i$ were elicited by the addition of NMDA/glycine (50 μM/1 μM) in the presence or absence of different concentrations of each test compound. The $IC_{50}$ values were derived for each test compound using from 2 to 8 separate experiments per test compound, and the standard error level was less than 10% of the mean value for each compound.

All of the arylalkylamines tested blocked increases in $[Ca^{2+}]_i$ in cerebellar granule cells elicited by NMDA/glycine. Certain arylalkylamines similar in structure to Compound 1 or Compound 2 were nearly as potent as MK-801 ($IC_{50}$=34 nM) which is the most potent compound in the literature known to preferentially block NMDA receptors. Compound 3 had an $IC_{50}$=2 nM, that is, 17-fold more potent than MK-801. Many of the arylalkylamines tested were more potent than competitive antagonists such as AP5 ($IC_{50}$=15 µM). The inhibitory effects of the arylalkylamines were not overcome by increasing the concentrations of NMDA or glycine. That is, no change was observed in the $EC_{50}$ for either NMDA or glycine. The arylalkylamines are thus noncompetitive antagonists at the NMDA receptor-ionophore complex, and act neither at the glutamate nor the glycine binding sites.

EXAMPLE 2

Activity Against Kainate and AMPA Receptor Function

Measurements of $[Ca^{2+}]_i$ in cerebellar granule cells can also be used to monitor activation of the native kainate or AMPA receptors present in this tissue. Although the increases in $[Ca^{2+}]_i$ evoked by these agonists are of a lesser magnitude than those evoked by NMDA/glycine, such responses are robust and can be used to precisely assess the specificity of action of arylalkylamines on pharmacologically defined glutamate receptor subtypes. Comparative measurements of $[Ca^{2+}]_i$ revealed a clear distinction in the receptor selectivity of the arylalkylamines. Some, like JSTX-3 (Joro Spider toxin from the spider *Nephila clavata*), were more potent antagonists of responses elicited by kainate (100 µM) or AMPA (30 µM). On the other hand, arylalkylamines within the two structural classes defined by Compound 1 and by Compound 2 were found to inhibit preferentially responses evoked by NMDA (showing about a 100-fold difference in potency). Thus, arylalkylamines such as Compound 1 and Compound 2 are potent and selective inhibitors of NMDA receptor-mediated responses in cerebellar granule cells.

EXAMPLE 3

Patch Clamp Electrophysiology Studies

Patch clamp electrophysiological studies on isolated cortical or hippocampal neurons from adult rat brain have provided additional insight into the mechanism of action of Compound 1, Compound 2 and Compound 3. These studies revealed potent and selective inhibitory effects of arylalkylamines on responses mediated by NMDA receptors. Thus, compounds such as Compound 1 blocked responses to NMDA at nanomolar concentrations without affecting the responses to kainate. These results, which show selective inhibitory effects of the arylalkylamines in cortical and hippocampal neurons, indicate that the arylalkylamines target NMDA receptors in different regions within the mammalian CNS. Moreover, it was found that the inhibitory effects of these compounds were use- and voltage-dependent. This strongly suggests that these compounds are blocking the open channel and, by this action, behave as noncompetitive NMDA receptor antagonists. Importantly, however, the arylalkylamines could be distinguished from both $Mg^{2+}$ and MK-801, especially with respect to the voltage-dependence of their onset of action and reversibility of effect.

EXAMPLE 4

Radioligand Binding Assays

Radioligand binding studies have demonstrated that arylalkylamines such as Compound 1 and Compound 2 have a unique site of action. Although they act like MK-801 in some respects (noncompetitive open-channel blockade, discussed above), they fail to displace [$^3$H]MK-801 binding at concentrations that completely block NMDA receptor-mediated responses. Assays such as these also demonstrate that the arylalkylamines do not bind with high affinity to the known MK-801, $Mg^{2+}$, or polyamine binding sites on the NMDA receptor-ionophore complex. Neither do the arylalkylamines bind directly to either the glutamate, glycine or sigma binding sites at concentrations that block NMDA receptor-mediated responses. [$^3$H]Compound 2 was synthesized as a radioligand for use in binding studies to further explore the mechanism of action of Compound 2 and particularly for use in a high-throughput screen to assess the activity of other analogs and to detect new lead structures. A similar approach was taken for [$^3$H]Compound 5. It is clear that compounds like Compound 1 and Compound 2 target a site on the NMDA receptor-ionophore complex for which no other known compounds presently exist. The novel site of action of the arylalkylamines at the molecular level translates into pronounced therapeutic advantages at the behavioral level. As described below, the arylalkylamines possess a quite different behavioral profile from other noncompetitive antagonists of the NMDA receptor.

EXAMPLE 5

Synaptic Transmission Studies

The above findings demonstrate that certain arylalkylamines, specifically those related in structure to Compound 1 and Compound 2, act through a novel mechanism and site of action to potently and selectively inhibit NMDA receptor-mediated responses on neurons from several different brain areas. To further assess the selective inhibitory actions of the arylalkylamines, their effects on synaptic transmission mediated by NMDA or AMPA receptors were assessed.

Glutamate-mediated transmission at synapses of Schaffer collateral fibers and CA1 pyramidal cells was measured in slices of rat brain containing the hippocampus. This assay measures electrophysiologically the postsynaptic depolarization caused by the presynaptic release of glutamate, and can readily distinguish synaptic transmission mediated by NMDA or AMPA receptors. Arylalkylamines like Compound 1, Compound 2 and Compound 3 were again found to exert preferential inhibitory effects on NMDA receptor-mediated responses, and depressed responses mediated by AMPA receptors only at much higher concentrations. For example, Compound 1 had an $IC_{50}$ for the NMDA receptor-mediated response of 20 µM, but an $IC_{50}$ for the AMPA receptor-mediated response of 647 µM. These results show that arylalkylamines can selectively inhibit synaptic transmission mediated by NMDA receptors. Other naturally occurring arylalkylamines present in the venom of *Agelenopsis aperta* likewise exert potent and selective inhibitory effects on NMDA receptor-mediated responses in the rat hippocampus.

In the aggregate, then, the results of these various studies are complementary and together identify a structurally novel class of compounds with potent and selective inhibitory activity on NMDA receptors in the mammalian CNS. Additionally, these compounds target a unique site on the NMDA receptor-ionophore complex. Compound 1, Compound 2 and Compound 3 were selected for additional study in a variety of in vitro and in vivo assays that model therapeutically important endpoints.

Neuroprotectant Activity

Desired properties of a neuroprotectant drug include the following. (1) The drug can be administered by oral or injectable routes (i.e., it is not significantly broken down in the stomach, intestine or vascular system and thus reaches the tissues to be treated in a therapeutically effective amount). Such drugs are easily tested in rodents to determine their bioavailability. (2) The drug exhibits neuroprotectant activity (i.e., efficacy) when given after an ischemic insult (stroke, asphyxia) or traumatic injury (head trauma, spinal cord injury). (3) The drug is devoid of or has minimal side effects such as impairment of cognition, disruption of motor performance, sedation or hyperexcitability, neuronal vacuolization, cardiovascular activity, PCP-like abuse potential, or PCP-like psychotomimetic activity.

Although glutamate is the physiological synaptic transmitter, chronic exposure to glutamate leads to neuronal cell death. Much of the neurodegeneration caused by glutamate appears to be mediated by NMDA receptors and results directly from chronically elevated levels of cytosolic $Ca^{2+}$. There is now extensive experimental support for the view that NMDA and AMPA receptors play a major role in mediating the neuronal degeneration following a stroke and other ischemic/hypoxic events (Choi, Glutamate neurotoxicity and diseases of the nervous system. *Neuron* 1: 623, 1988). Most of this evidence is based on the ability of competitive or noncompetitive antagonists of the NMDA or AMPA receptor to effectively block neuronal cell death in both in vitro and in vivo models of stroke. Compound 1, Compound 2 and Compound 4 were therefore examined for neuroprotectant effects in standard assays designed to detect such activity.

EXAMPLE 6

Cortical Neuron Protection

To assess the in vitro neuroprotectant effect of arylalkylamines, mouse cortical neurons grown in culture were exposed for 5 minutes to NMDA, and cell death after 24 hours was monitored by measuring the release of lactate dehydrogenase (LDH), a cytoplasmic enzyme that is released from dying cells (Choi et al., Glutamate neurotoxicity in cortical cell culture. *J. Neurosci.* 7: 357, 1987). Exposure to NMDA killed about 80% of the cortical neurons. Compound 1 or Compound 2, included along with NMDA, prevented cell death with $IC_{50}$ values of 70 μM and 30 μm, respectively. The effective concentrations of the arylalkylamines are higher than those of other noncompetitive NMDA receptor antagonists, but similar to those of competitive antagonists. The effective concentrations of NMDA receptor antagonists vary depending on the particular experimental conditions and the type of cell studied (cortical, hippocampal, striatal). This neuroprotectant effect likely results from the ability of these compounds to block the influx of extracellular $Ca^{2+}$ triggered by the NMDA receptor.

More rigorous testing to determine potential therapeutic efficacy involved in vivo stroke models. In these models, the blood supply is temporarily blocked by clamping the main arteries to the brain. Two in vivo models of this sort were used to determine the ability of Compound 1, Compound 2 and Compound 4 to prevent neuronal cell loss.

EXAMPLE 7

Bilateral Carotid Artery Occlusion

The first assay was the bilateral common carotid artery occlusion model of forebrain ischemia performed in the gerbil (Karpiak et al., Animal models for the study of drugs in ischemic stroke. *Ann. Rev. Pharmacol. Toxicol.* 29: 403, 1989; Ginsberg and Busto, Rodent models of cerebral ischemia. *Stroke* 20: 1627, 1989). Blood flow to the brain was interrupted for 7 minutes by clamping the carotid arteries. The test compounds were administered as a single dose given intraperitoneally (i.p.) 30 minutes after reinstating blood flow. During the course of these experiments, the core body temperature of the animals was maintained at 37° C. to prevent any hypothermic reaction. It has been shown that many NMDA receptor antagonists cause hypothermia and this effect can account for much of the protective effect of these compounds. The brains were examined for neuronal cell death 4 days later by silver staining sections of the brain and quantifying death by morphometric analysis. Compound 2 (20 mg/kg) significantly ($p<0.05$) protected against neuronal cell death in all areas of the brain examined (region CA1 of hippocampus, striatum and neocortex). Doses as low as 1 mg/kg afforded complete (>98%) protection of the striatum. The degree of protection is comparable to that achieved with similar doses of the noncompetitive NMDA antagonist, MK-801.

In subsequent experiments, Compound 1 (10 mg/kg) produced a 23% reduction in the amount of neuronal death in region CA1 of the gerbil hippocampus measured at 7 days post-ischemia, while Compound 4 (10 mg/kg) provided 90% protection.

EXAMPLE 8

Middle Cerebral Artery Occlusion

The middle cerebral artery model of stroke performed in the rat (Karpiak et al., Animal models for the study of drugs in ischemic stroke. *Ann. Rev. Pharmacol. Toxicol.* 29: 403, 1989; Ginsberg and Busto, Rodent models of cerebral ischemia. Stroke 20: 1627, 1989) is different from the gerbil model because it results in a more restricted brain infarct, and thereby approximates a different kind of stroke (focal thrombotic stroke). In the first study using this stroke model, one cerebral artery was permanently occluded by surgical ligation. The test compounds were administered 30 minutes after the occlusion by a single intraperitoneal (i.p.) injection. During the course of these experiments, the core body temperature of the animals was maintained at 37° C. to prevent any hypothermic reaction. Brains were assessed histologically for neuronal cell loss 24 hours later. Infarct volumes were calculated using the area of histological pallor from 10 slides and integrating the distance between each successive section. A single dose (30 mg/kg) of Compound 1 was found to significantly ($p<0.05$) protect against neuronal cell loss equally as well as a maximally effective dose (10 mg/kg) of MK-801 (approximately 15% protection). Preliminary studies with Compound 2 (20 mg/kg) indicated a similar trend.

In the second study of focal cerebral ischemia in the rat, the middle cerebral artery was permanently occluded by passing a small piece of suture thread through the carotid artery to the region of the middle cerebral artery. Core body temperature was maintained at 37° C. Compound 4, 10 mg/kg i.p. administered immediately after the onset of the ischemic event, produced a statistically significant reduction in the volume of the brain infarct (20%) recorded 24 hr later.

In a third model of focal cerebral ischemia in the rat, an ischemic infarct was produced by a photothrombotic method using the dye Rose Bengal. Compound 4, 10 mg/kg i.p. administered 30 min after the ischemic event, produced a 20% reduction in the volume of the infarct, similar to that seen with the noncompetitive NMDA receptor antagonist, MK-801.

In a fourth model of focal cerebral ischemia in the rat, the middle cerebral artery was temporarily occluded by passing a small piece of suture thread through the carotid artery to the region of the middle cerebral artery. The suture thread was withdrawn after an ischemic period of 2 hr. Core body temperature was maintained at 37° C. Compound 4 administered at 10 mg/kg i.p. immediately after the onset of the ischemic event, produced a statistically significant reduction in the volume of the brain infarct (37%) recorded 72 hr later.

Several important features of the lead compounds emerge from these in vivo results. First, and most importantly, Compound 1, Compound 2 and Compound 4 demonstrate neuroprotectant effects in several different in vivo models of stroke. The gerbil assay is a model for transient global cerebral ischemia and hypoxia such as cardiac arrest or perinatal hypoxia. The rat assays are models of permanent and temporary focal cerebral ischemia. The finding that Compound 1 and Compound 4 are neuroprotective in the permanent focal stroke models is surprising because the accessibility of the drug to the site of infarction is limited to the penumbral region which generally is not large. Nonetheless, Compound 1 and Compound 4 significantly ($p<0.05$) limited the extent of damage. Second, the compounds are effective when administered after the ischemic event. This is important because there is believed to be a "window of opportunity" following an infarct during which drugs may effectively halt necrotic damage. How long this time is in humans has not been defined precisely, and will likely vary depending upon the type of infarct. The essential observation, however, is that these compounds can prevent the spread of neuronal cell death once the degenerative process has commenced. Finally, Compound 1, Compound 2 and Compound 4 are effective when administered parenterally, demonstrating that they penetrate the blood-brain barrier.

Anticonvulsant Activity

Desired properties of an anticonvulsant drug include: the drug can be administered by oral or injectable routes, the drug exhibits effective anticonvulsant activity against several seizure types, including, but not limited to, simple partial seizures, complex partial seizures, status epilepticus, and trauma-induced seizures such as occur following head injury, inclusing head surgery; and the drug is devoid of or has minimal side effects such as impairment of cognition, disruption of motor performance, sedation or hyperexcitability, neuronal vacuolization, cardiovascular activity, PCP-like abuse potential, or PCP-like psychotomimetic activity.

Glutamate is the major excitatory transmitter in the brain, and thus may play a major role in seizure activity, and contribute to the pathogenesis of epilepsy. Much of the evidence favoring a major role for glutamate receptors in epilepsy derives from pharmacological studies demonstrating that glutamate receptor agonists elicit seizures, and that NMDA and AMPA receptor antagonists are effective anticonvulsants when administered in vivo. There are numerous in vivo models involving different kinds of seizures and behavioral effects that are relevant for clinically distinct forms of epilepsy. It is thus prudent to test for effects in several models, because it may be an oversimplification to suppose that the same mechanism underlies all forms of seizure activity.

EXAMPLE 9

Convulsant Blocking Activity

In initial studies, the ability of arylalkylamines to block seizures induced by kainate, picrotoxin or bicuculline were examined. Each of these convulsants acts through a different mechanism and seizures elicited by kainate are qualitatively different from those elicited by picrotoxin or bicuculline. In these experiments, a fraction of *Agelenopsis aperta* venom containing several arylalkylamine toxins was administered intravenously (iv) 5 min before picrotoxin or bicuculline, and 5 min after kainate administration. The arylalkylamines diminished the seizures induced by all three of these agents. The effects of picrotoxin or bicuculline were so severe that all 19 control animals died within 25 minutes. In contrast, there were no deaths in the 9 animals pretreated with the arylalkylamines. In fact, only about half the animals treated with the arylalkylamines showed any convulsions at all and those symptoms abated within an hour. These results demonstrate clear anticonvulsant effects of arylalkylamines and prompted further studies using purified arylalkylamines and their analogs.

EXAMPLE 10

Seizure Stimuli

Three different seizure-inducing test paradigms were used initially in this second group of studies and arylalkylamines such as Compound 1 proved to be effective anticonvulsants in two such paradigms. The first two models used DBA/2 mice which are prone to audiogenic seizures. Seizures were elicited by sound (bell tone at 109 dBs) or the intraperitoneal (ip) administration of NMDA (56 mg/kg). The test substances were administered 15–30 min before the convulsant stimulus. The number of clonic seizures was recorded for 1 min following the audiogenic stimulus or for 15 min following the administration of NMDA. Compound 1, Compound 2, and several other arylalkylamines such as Compound 3 and Compound 4 depressed seizures evoked by either stimulus. For example, Compound 2 had an $ED_{50}$ of 0.13 mg/kg s.c. for audiogenic stimulus and 0.083 mg/kg s.c. for NMDA stimulus. Similarly, the $EC_{50}$ for Compound 4 in the audiogenic seizure model (0.08 mg/kg) approached that for MK-801 (0.02 mg/kg). In contrast, neither Compound 1 nor Compound 2 was effective at doses up to 50 mg/kg s.c. in reducing seizures in CF-1 mice elicited by i.p. NMDA.

In a second independent series of experiments, Compound 1 and Compound 4 were found to prevent seizures induced by sound in another genetically susceptible mouse model of reflex epilepsy (Frings mice) following intraperitoneal injection with $IC_{50}$ values of 14.3 mg/kg and ~15 mg/kg, respectively. These compounds were considerably more potent against audiogenic seizures in Frings mice following intracerebroventricular (i.c.v.) injection, with IC$_{50}$ values of 0.63 μg (Compound 1) and 4.77 μg (Compound 4). Compound 1 was also found to be effective against seizures elicited by maximal electroshock in CF1 mice at a dose of 4 μg i.c.v.

In further studies using the genetically susceptible mouse model of reflex epilepsy (Frings mice), Compound 9, Compound 12 and Compound 14, administered by i.c.v. injection, prevented sound-induced seizures with IC$_{50}$ values of 4.77 μg, 12.2 μg and 13.9 μg, respectively.

These collective findings demonstrate that arylalkylamines such as Compound 1, Compound 2 and Compound 4 are effective in preventing epileptic (audiogenic) and nonepileptic (chemoconvulsant) seizures. This generalized pattern of activity suggests that arylalkylamines are clinically useful in controlling seizure activity. In addition, the potency of Compound 1, Compound 2 and especially Compound 4 in in vivo models of seizure activity shows that these compounds can have the therapeutically relevant effects when administrated parenterally in low doses, and are especially potent when administered directly into the cerebral ventricles.

Analgesic Activity

Desired properties of an analgesic drug include: the drug can be administered by oral or injectable routes, the drug exhibits analgesic activity, the drug is devoid of or has minimal side effects such as impairment of cognition, disruption of motor performance, sedation or hyperexcitability, neuronal vacuolization, cardiovascular activity, PCP-like abuse potential, or PCP-like psychotomimetic activity.

Glutamate and NMDA receptor-mediated responses may play a role in certain kinds of pain perception (Dickenson, A cure for wind up: NMDA receptor antagonists as potential analgesics. *Trends Pharmacol. Sci.* 11: 302, 1990). The possible analgesic effects of Compound 1, Compound 2, Compound 3 and Compound 4 were therefore examined.

EXAMPLE 11

Writhing Response Test

In the first series of experiments, the animals were administered an unpleasant stimulus (2-phenyl-1,4-benzoquinone, PBQ) which elicits a writhing response (abdominal stretching). Typically, the number of writhes occurring in a 5 min observation period is recorded. Classic analgesic drugs, such as morphine, are effective at decreasing the number of PBQ-elicited writhes (100% block of the writhing response at 4 mg/kg i.p.). Nonsteroidal antiinflammatory agents are likewise effective in this model. Compound 1 (2 mg/kg), Compound 2 (2 mg/kg) and Compound 3 (1 mg/kg) depressed the writhing response by greater than 95% when administered s.c. or i.p. 30 minutes before PBQ. These results demonstrate that Compound 1, Compound 2 and Compound 3 alleviate visceral pain.

In a similar series of studies, Compound 1 and Compound 4 were found to inhibit acetic acid-induced writhing in mice following i.p. injection with IC$_{50}$ values of 10 mg/kg and 1 mg/kg, respectively.

EXAMPLE 12

Hot Plate Test

Compound 1 was tested for analgesic activity in an additional assay. In this model of analgesic activity, mice were administered test substances s.c. 30 min before being placed on a hot plate (50° C.). The time taken to lick the feet or jump off the plate is an index of analgesic activity, and effective analgesics increase the latency to licking or jumping. Morphine (5.6 mg/kg) increased the latency to jump by 765%. Compound 1 was likewise effective in this assay and, at doses of 4 and 32 mg/kg, increased the latency to foot licking by 136% and the latency to jumping by 360%, respectively.

It is noteworthy that the analgesic effects of Compound 1 in the hot plate assay were not accompanied by a decreased performance in the inverted grid assay (see below). This shows that the increase in the latency to jump off the hot plate does not simply reflect impaired motor capabilities. Together, these data suggest that Compound 1 possesses significant analgesic activity.

In a later series of experiments, Compound 1 and Compound 4 were demonstrated to possess significant analgesic activity in rats when administered by the intrathecal (i.th.) route. In these experiments, a 52° C. hot plate was used as the nociceptive stimulus. Compound 1 (0.3–3 nmol) and Compound 4 (0.3–3 nmol) produced dose- and time-dependent antinociceptive effects; these arylalkylamines were similar to morphine (0.3–3 nmol) in terms of potency and efficacy. The NMDA receptor antagonist, MK-801, on the other hand, was ineffective in this assay (3–30 nmol).

EXAMPLE 13

Tail Flick Test

In this standard assay, the thermal nociceptive stimulus was 52° C. warm water with the latency to tail flick or withdrawal taken as the endpoint. Compound 1 (0.3–3 nmol) and Compound 4 (0.3–3 nmol) produced a dose- and time-dependent analgesic effect following i.th. administration. These arylalkylamines were similar to morphine (0.3–3 nmol) in terms of potency and efficacy. The NMDA receptor antagonist, MK-801, on the other hand, was ineffective in this assay (3–30 nmol).

EXAMPLE 14

Formalin Test

Male Sprague-Dawley rats were habituated to an observation chamber for at least 1 hr before receiving an injection of dilute formalin (5%) in a volume of 50 μl into the left rear paw. Behavioral responses were monitored immediately after s.c. injection of formalin into the dorsal surface of the paw by counting the number of flinches exhibited by the animal. Behaviors were monitored for at least 50 min after formalin injection and were recorded as early phase responses (0–10 min post-formalin) and late phase responses (20–50 min post-formalin). Compounds were injected intrathecally (i.th.) 10 min prior to formalin (pre-treatment) or 10 min after formalin (post-treatment) in a volume of 5 μl.

Intraplantal administration of formalin produced a typical biphasic response of flinching behavior, commonly described as the early and late phase responses. Intrathecal administration of Compound 1 (0.3–10 nmol) or Compound 4 (0.3–10 nmol) given as a pretreatment to formalin effectively inhibited both early- and late-phase flinching behaviors. This effect of pretreatment with the arylalkylamines was similar to that seen with pretreatment with morphine (1–10 nmol) or MK-801 (1–30 nmol).

Compound 1 (0.3–10 nmol i.th.) administered after the formalin produced some inhibition of late-phase flinching, though significance was achieved only at the 10 nmol dose. Compound 4 (0.3–10 nmol i.th.) administered after the formalin produced significant inhibition of late-phase flinching, with significance achieved at the 3 and 10 nmol doses. This analgesic profile of activity of the arylalkylamines is similar to that seen with post-formalin administration of morphine (1–10 nmol); post-formalin administration of MK-801 (1–30 nmol), however, failed to affect late-phase flinching.

Taken together, the results obtained with the hot plate, tail flick and formalin assays demonstrate that arylalkylamines such as Compound 1 and Compound 4 have significant analgesic activity in several rodent models of acute pain. The formalin assay additionally demonstrates that arylalkylamines are effective in an animal model of chronic pain. Importantly, the arylalkylamines possess significant analgesic activity when administered after the formalin stimulus. This profile of activity clearly distinguishes the arylalkylamines from standard NMDA receptor antagonists such as MK-801.

Side Effects of Arylalkylamines

Given the important role NMDA receptors play in diverse brain functions, it is not surprising to find that antagonists of this receptor are typically associated with certain unwelcome side effects. In fact, it is this property that provides the major obstacle to developing therapies that target NMDA receptors. The principal side effects, which characterize both competitive and noncompetitive antagonists, are a PCP-like psychotomimetic activity, impairment of motor performance, sedation or hyperexcitability, impairment of cognitive abilities, neuronal vacuolization, or cardiovascular effects (Willetts et al., The behavioral pharmacology of NMDA receptor antagonists. *Trends Pharmacol. Sci.* 11: 423, 1990; Olney et al., Pathological changes induced in cerebrocortical neurons by phencyclidine and related drugs. *Science* 244: 1360, 1989). The psychotomimetic effect associated with inhibition of NMDA receptor-mediated responses is epitomized in the response to phencyclidine (PCP) or "angel dust" which acts at the MK-801 binding site. Impairment of cognitive ability is associated with the important role that NMDA receptors normally play in learning and memory.

Relatively less is known concerning the side effect profile of AMPA receptor antagonists. However, it is becoming clear that such compounds also elicit motor impairment, ataxia and profound sedation.

The activity of arylalkylamines was examined in animal models that index motor impairment, sedation and psychotomimetic activity as well as both in vitro and in vivo models of learning and memory.

(a) PCP-like Psychotomimetic Activity

In rodents, both competitive and noncompetitive antagonists of the NMDA receptor produce a PCP-like stereotypic behavior characterized by hyperactivity, head-weaving, and ataxia (Willetts et al., The behavioral pharmacology of NMDA receptor antagonists. *Trends Pharmacol. Sci.* 11: 423, 1990; Snell and Johnson, In: *Excitatory Amino Acids in Health and Disease,* John Wiley & Sons, p. 261, 1988). We investigated whether the arylalkylamines would elicit such behaviors. In addition, we investigated whether the arylalkylamines would substitute for PCP in rats trained to discriminate PCP from saline (Willetts et al., The behavioral pharmacology of NMDA receptor antagonists. *Trends Pharmacol. Sci.* 11: 423, 1990), and whether the arylalkylamines would elicit a PCP-like neuronal vacuolization (Olney et al., Pathological changes induced in cerebrocortical neurons by phencyclidine and related drugs. *Science* 244: 1360, 1989).

EXAMPLE 15

Locomotor Activity

The first assay simply monitors locomotor activity during the first hour following peripheral (s.c. or i.p.) administration of test substance. Mice received a dose of Compound 1 15 min before being placed into activity chambers. Activity was quantified by counting the number of breaks in a phototube grid in a 60 min period. In this assay, MK-801 (0.25 mg/kg p.o.) causes a 2- to 3-fold increase in locomotor activity. However, Compound 1, even when tested at 32 mg/kg s.c., did not elicit hyperactivity and, in fact, tended to depress it. This result, using a purified arylalkylamine in mice, complements earlier results obtained in rats where the entire arylalkylamine-containing fraction from *Agelenopsis aperta*, when injected intravenously, did not elicit a PCP-like behavioral syndrome but seemed to produce a mild sedative effect.

EXAMPLE 16

Motor Impairment

In the first assay for generalized motor impairment, Compound 1 was examined in the inverted grid assay. In this assay, animals are placed on a wire-holed grid suspended from a rotating metal bar which can be inverted. The animals are then scored for their ability to climb to the top or hang on to the grid. Animals with severe motor impairment fall off the grid. This assay provides an index of "behavioral disruption" that may result from ataxia, loss of the righting reflex, sedation, or muscle relaxation. In these tests, Compound 1, administered at 32 mg/kg s.c., did not lessen the ability of DBA/2 mice to right themselves when the grid was inverted (p>0.05). Compound 2 was likewise without effect (p>0.05) on motor performance in DBA/2 mice when administered at a dose of 20 mg/kg s.c. These doses are considerably higher than those required to prevent sound-induced seizures in DBA/2 mice (see Example 10 above).

The second assay of acute motor impairment was the rotorod assay. In this assay, Frings and CF1 mice were injected with test compound and placed on a knurled rod which rotated at a speed of 6 rpm. The ability of the mice to maintain equilibrium for long periods of time was determined; those mice that were unable to maintain equilibrium on the rotorod for 1 min in each of 3 trials were considered impaired. Compound 1 produced acute motor impairment in Frings mice with a $TD_{50}$ (that dose which produced motor toxicity in 50% of the test animals) of 16.8 mg/kg i.p. This dose is similar to that which prevents sound-induced seizures in Frings mice (see Example 10 above). There is a much clearer separation between effective and toxic doses of Compound 1 in Frings mice, however, when the Compound is administered i.c.v. In this case, no apparent motor toxicity was evident until the dose of Compound 1 exceeded 1.56 μg i.c.v. (>2 times the $ED_{50}$ of 0.63 μg). Finally, motor impairment in CF1 mice was noted with Compound 1 following i.c.v. administration of 4 μg.

Compound 4, Compound 9, Compound 12 and Compound 14 were administered to Frings mice by i.c.v. injection, and acute motor impairment was measured. The $TD_{50}$ values for Compounds 4, 9, 12 and 14 were 8–16 μg, 14.8 μg, 30.2 μg and 30.8 μg, respectively. These $TD_{50}$ values were 2–3 times higher than the effective $IC_{50}$ values for anticonvulsant potency (see Example 10 above); a clear separation between effective and toxic doses was noted.

EXAMPLE 17

PCP Discrimination

In this assay, rats who have been trained to lever press for food reinforcement must select which of two levers in their cages is correct. The only stimulus they have for selecting the correct lever is their ability to detect whether they received a PCP or vehicle injection. After about two months of training, rats become very good at discriminating PCP from vehicle injections and can then be tested with other drugs to determine if they are discriminated as PCP. When tested in this procedure, other drugs which are known to produce a PCP-like intoxication substitute for PCP. These drugs include various PCP analogs such as ketamine and the noncompetitive NMDA receptor antagonist, MK-801.

Compound 1 (1–30 mg/kg i.p.) did not substitute for PCP, and thus was completely devoid of PCP-like discriminative stimulus effects. At 30 mg/kg i.p., only 1 of the 7 animals tested responded at all on either lever. It is thus clear that a behaviorally effective dosage range of Compound 1 was evaluated. As the ability of test compounds to produce PCP-like effects in rats is believed to be predictive of their ability to produce PCP-like psychotomimetic activity and abuse liability in humans, these results strongly suggest that the arylalkylamines such as Compound 1 will lack such deleterious side effects in man.

EXAMPLE 18

The administration of compounds such as PCP and MK-801 to rats produces a neurotoxic effect termed neuronal vacuolization. Following a single dose of such compounds, vacuoles are found in particular central neurons, especially those in the cingulate cortex and retrosplenial cortex. No such vacuolization was present in rats treated with Compound 1 at the single high dose of 100 mg/kg i.p.

Taken together, the results on locomotor activity, motor impairment, PCP discrimination and neuronal vacuolization strongly suggest that arylalkylamines will be devoid of PCP-like side effects in man.

(b) Cognitive impairment

One of the major reasons for postulating a role of NMDA receptors in memory and learning derives from cellular studies on long-term potentiation (LTP) in the rat hippocampus. LTP is a long-lasting increase in the magnitude of synaptic responses produced by brief yet intense synaptic stimulation. Since the discovery of this phenomenon, it has become the preeminent cellular model of learning in the vertebrate brain (Teyler and Discenna, Long-term potentiation. *Annu. Rev. Neurosci.* 10: 131, 1987). Transmission at synapses formed by Schaffer collaterals onto CA1 pyramidal cells is mediated by NMDA and AMPA receptors. Following a brief tetanizing stimulus, the magnitude of the population spike (a measure of synaptic transmission) is greatly increased and remains so for hours. It has been shown that all known competitive and noncompetitive antagonists of NMDA receptors block LTP in the rat hippocampus, whereas antagonists of non-NMDA receptors are without effect (Collingridge and Davis, In: *The NMDA Receptor,* IRL Press. p. 123, 1989). This supports a role of NMDA receptors in memory and learning.

EXAMPLE 19

LTP Assay

The effects of selected arylalkylamines and literature standards were examined for effects on LTP in slices of rat hippocampus. As anticipated, all the conventional competitive (AP5 and AP7) and noncompetitive (MK-801 and ifenprodil) NMDA receptor antagonists inhibited the induction of LTP in the hippocampus. Slices of rat hippocampus were superfused for 30–60 min with a test compound before delivering a tetanizing stimulus consisting of 3 trains, separated by 500 msec, of 100 Hz for 1 sec each. The response amplitude was monitored for an additional 15 minutes post-tetanus. The tetanizing stimulus caused a mean 95% increase in the amplitude of the synaptic response. The induction of LTP was significantly blocked ($p<0.05$) by competitive (AP5, AP7) or noncompetitive (MK-801, ifenprodil) NMDA receptor antagonists. Quite surprisingly, none of the arylalkylamines tested (Compound 1, Compound 2, Compound 3 and others) blocked the induction of LTP ($p>0.05$), even when used at high concentrations (100–300 $\mu$M) that caused some inhibition of the control response.

These results highlight yet another unique and important feature of arylalkylamines. Arylalkylamines are the first, and at present the only, class of compounds shown to be selective and potent antagonists of the NMDA receptor that do not block the induction of LTP. This likely reflects the novel mechanism and site of action of arylalkylamines and suggests that drugs which target the novel site on the NMDA receptor will similarly lack effects on LTP. As LTP is the primary cellular model for learning and memory in the mammalian CNS, it additionally suggests that such drugs will lack deleterious effects on cognitive performance.

EXAMPLE 20

Learning Tests

Preliminary experiments using one of the more potent synthetic arylalkylamine analogs, Compound 3, in an in vivo learning paradigm demonstrate that these drugs lack effects on cognitive performance. In this test, rats were trained to alternate turning in a T maze for a food reward. MK-801 was included for comparison. Test compounds were administered i.p. 15 min before testing. Control animals made the correct choice about 80% of the time. Increasing doses of MK-801 progressively decreased the number of correct choices and this decrement in behavior was accompanied by hyperactivity. In contrast, Compound 3 did not impair the ability of the animals to make the correct choices ($p>0.05$). At the highest doses tested, Compound 3 caused some decrease in locomotor activity, exactly the opposite effect observed with MK-801.

Although MK-801 decreased learning performance in parallel with increases in locomotor activity, other studies using different paradigms in rodents and primates have shown a clear dissociation between the effects on learning and locomotion. Thus, both competitive and noncompetitive NMDA receptor antagonists impair learning at doses which do not cause any overt change in motor behavior. This demonstrates that conventional NMDA receptor antagonists impair learning independently of other side effects. The results of the T-maze assay demonstrate that Compound 3, and other arylalkylamines, do not impair learning even at doses that cause some decrease in locomotor activity.

One additional observation emerged from these learning tests. The animals' first response on the second day of testing was random and was therefore not dependent on the last response of the previous day's testing. Control animals thus correctly made the first choice about 50% of the time. MK-801 has no effect on this first choice. However, animals administered Compound 3 on the previous day made the first choice correctly considerably more often. Unlike control animals then, the animals treated with Compound 3 behaved as if they remembered the last choice of the previous day.

In a second series of experiments, the effect of Compound 4 on learning in the Morris water maze task was evaluated. In this test, a hidden platform was placed in a fixed location in a circular steel tank, and submerged 2 cm below the surface of the water. Each rat was given 3 trials per day with a 10 min intertrial interval for 5 days. A trial was initiated by placing the rat in the water, nose facing the wall of the tank, at one of three predetermined starting locations. The order of the start location was varied daily. Learning was measured as a decrease in time required to swim to the platform. If an animal failed to locate the platform within 60 sec after the start of the trial, the rat was hand-guided to it. The animals remained on the platform for 10 sec before being removed from the tank. Ten min after the last training trial on day 5, the animals received a probe test. The platform was removed for this 1 trial task and the animals were allowed to swim for 60 sec to assess the spatial bias for the platform location. Two measures were recorded from this task: latency to first crossing the area where the platform had been, and total number of crossings. A total of 5 injections of Compound 4 were given to each rat. In the first series of experiments, Compound 4 was administered at 10 mg/kg i.p. daily for 5 days. This treatment regimen impaired learning; however, these animals experienced significant weight loss and unusual behavioral signs ("shivering," motor impairment, difficulty in swimming) with repeated dosing of Compound 4. In a subsequent study, six animals received 1 mg/kg i.p. for the first 4 days of training, while two animals received 5 mg/kg i.p. during this period. On the last day of training, both groups received 10 mg/kg. Neither the 1 mg/kg nor the 5 mg/kg animals showed any impairment in learning the location of the hidden platform, nor did the final 10 mg/kg dose produce any impairment in the ability of the animal to perform the already learned task.

The results of these learning tasks are encouraging. They suggest that arylalkylamines lack the learning and memory deficits that typify other NMDA receptor antagonists. In fact, there is a suggestion that the arylalkylamines may even be nootropic (memory enhancers).

(c) Cardiovascular Effects

In vivo studies with certain arylalkylamines revealed a hypotensive effect of these compounds, especially at high doses. On the basis of these results, a systematic study of the effects of arylalkylamines on cardiovascular function was performed.

EXAMPLE 21

$Ca^{2+}$ Channel Inhibition

We have discovered that some of the arylalkylamines are quite potent inhibitors of voltage-sensitive $Ca^{2+}$ channels, specifically those sensitive to inhibition by dihydropyridines (L-type channels). Such effects on vascular smooth muscle would be expected to dilate blood vessels and cause a drop in blood pressure, thus producing hypotension.

The ability of arylalkylamines to inhibit dihydropyridine-sensitive $Ca^{2+}$ channels was examined in cerebellar granule cells and a rat aortic smooth muscle cell line, $A_7r5$ cells. In cerebellar granule cells, Compound 2 inhibited depolarization-induced increases in $[Ca^{2+}]_i$ at concentrations 100-fold higher than those required to block responses to NMDA ($IC_{50}$ values of 24 $\mu$M and 161 nM, respectively). Overall, we have observed a wide range of potencies against voltage-sensitive $Ca^{2+}$ channels that does not correlate with potency against NMDA receptors. This strongly suggests that further structure-activity work based on chemical modification of the arylalkylamine molecule will lead to the development of compounds that are very potent NMDA antagonists with low potency against voltage-sensitive $Ca^{2+}$ channels. Indeed, Compound 1 (with an $IC_{50}$ of 102 nM against NMDA receptor-mediated responses in cerebellar granule cells) is a relatively poor inhibitor of voltage-sensitive $Ca^{2+}$ channels in cerebellar granule cells ($IC_{50}$=257 $\mu$M) and is virtually without effect on voltage-sensitive $Ca^{2+}$ influx in $A_7r5$ cells ($IC_{50}$=808 $\mu$M).

Arylalkylamines are not, however, indiscriminate blockers of voltage-sensitive $Ca^{2+}$ channels. They do not, for example, affect voltage-sensitive $Ca^{2+}$ channels in cerebellar Purkinje cells (P-type channels) or those channels thought to be involved in neurotransmitter release (N-channels). The arylalkylamines that do block voltage-sensitive $Ca^{2+}$ channels appear to target specifically L-type $Ca^{2+}$ channels. Moreover, as mentioned above, there is a high degree of structural specificity in this effect. For example, one arylalkylamine is 57 times more potent than another arylalkylamine in blocking $Ca^{2+}$ influx through L-type channels, where the only structural difference between the compounds is the presence or absence of a hydroxyl group.

EXAMPLE 22

In vivo Cardiovascular Studies

The arylalkylamines Compound 1 and Compound 2 produce moderate drops (20–40 mm Hg) in mean arterial blood pressure (MABP) in anesthetized rats at doses which are effective in the in vivo stroke models (10–30 mg/kg s.c.). The hypotensive effect of Compound 4 has been evaluated in greater detail. Compound 4 elicited a marked drop (40 mm Hg) in mean arterial pressure which persisted for approximately 90–120 min when administered at the dose of 10 mg/kg i.p.; it was in this same group of rats that Compound 4 afforded significant neuroprotection in the suture model of middle cerebral artery occlusion (see Example 8 above). Similar results were obtained in the rat study in which Compound 4 demonstrated neuroprotectant activity in the Rose Bengal photothrombotic model of focal ischemic stroke (see Example 8 above). Further studies using the pithed rat preparation strongly suggest that the hypotensive activity of Compound 4 is a peripherally mediated effect. The hypotension and bradycardia produced by Compound 4 was maintained in rats pretreated with atropine, suggesting that these effects are not mediated by a cholinergic mechanism. Similarly, Compound 4 elicited hypotension and bradycardia in chemically sympathectomized rats (pretreated with a ganglionic blocker), suggesting that these effects are not mediated via the sympathetic nervous system.

On the basis of these findings, it is anticipated that chemical efforts will minimize the cardiovascular side effects by (1) enhancing the uptake of arylalkylamine into the brain such that lower doses are required for neuroprotection, and (2) increasing the selectivity (potency ratio) of arylalkylamines for receptor-operated $Ca^{2+}$ channels over voltage-sensitive $Ca^{2+}$ channels.

Chemistry and Biological Activity of Simplified Synthetic Arylalkylamines

The present invention provides simplified arylalkylamines comprising the following structures:

FORMULA I

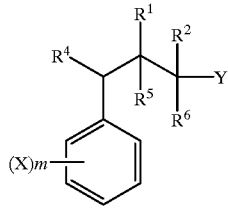

wherein:

$R^1$ and $R^5$ are independently selected from the group consisting of —H, alkyl, hydroxyalkyl, —OH, —O-alkyl, and —O-acyl;

$R^2$ and $R^6$ are independently selected from the group consisting of —H, alkyl, and hydroxyalkyl; or $R^1$ and $R^2$ together are —$(CH_2)_n$— or —$(CH_2)_n$—$N(R^3)$—;

$R^3$ is independently selected from the group consisting of —H, alkyl and 2-hydroxyethyl;

n is an integer from 1 to 6;

$R^4$ is selected from the group consisting of alkyl, cycloalkyl, and

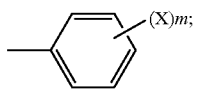

X is independently selected from the group consisting of —H, —Br, —Cl, —F, —$CF_3$, alkyl, —OH, —$OCH_3$, —O-alkyl, and —O-acyl;

m is independently an integer from 0 to 5; and

Y is —$NR^3R^3$, except when $R^1$ and $R^2$ together are —$(CH_2)n$—$N(R^3)$—, then Y is —H; and pharmaceutically acceptable salts thereof.

In preferred aspects of the invention,

Y is $NR^3R^3$;

$NR^3R^3$ is selected from the group consisting of —$NH_2$ and

—NH-methyl;

$R^4$ is;

$(X)m$ is independently selected from the group consisting of meta-fluoro, meta-chloro, ortho-methoxy, and ortho-methyl and;

$R^1$ is methyl, and $R^2$, $R^5$, and $R^6$ are —H; or $R^2$ is methyl, and $R^1$, $R^5$, and $R^6$ are —H; or $R^1$, $R^2$, $R^5$ and $R^6$ are —H.

In other preferred aspects of the present invention, $R^1$ and $R^5$ are independently selected from the group consisting of —H, lower alkyl, hydroxyalkyl, —OH, —O-alkyl, and —O-acyl;

$R^2$ and $R^6$ are independently selected from the group consisting of —H, lower alkyl, and hydroxyalkyl; or $R^1$ and $R^2$ together are —$(CH_2)_n$— or —$(CH_2)_n$—N$(R^3)$—;

$R^3$ is independently selected from the group consisting of —H and lower alkyl;

n is an integer from 1 to 6;

$R^4$ is selected from the group consisting of —H, lower alkyl, cycloalkyl, and

X is independently selected from the group consisting of —H, —Br, —Cl, —F, —$CF_3$, lower alkyl, —OH, and —$OCH_3$;

m is independently an integer from 0 to 5;

Y is —$NR^3R^3$, or hydrogen;

and pharmaceutically acceptable salts thereof, with the provisos that (a) when $R^1$ and $R^2$ together are —$(CH_2)_n$—$N(R^3)$—, then $R^5$, $R^6$, and Y are hydrogens; and (b) when $R^1$ and $R^2$ together are not —$(CH_2)_n$—$N(R^3)$—, then Y is —$NR^3R^3$.

In a further aspect, the invention features a method for treating a patient having a neurological disease or disorder comprising administering a the compounds of Formula II:

Formula II

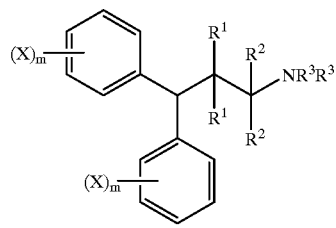

wherein X is independently selected from the group consisting of —H, —Br, —Cl, —F, —$CF_3$, alkyl, —OH, —$OCH_3$, —O-alkyl, and —O-acyl; $R^1$ is independently selected from the group consisting of —H, alkyl, hydroxyalkyl, —OH, —O-alkyl, and —O-acyl; $R^2$ is independently selected from the group consisting of —H, alkyl, and hydroxyalkyl; $R^3$ is independently selected from the group consisting of —H and alkyl; and m is independently an integer from 0 to 5; or the compounds of Formula III:

Formula III

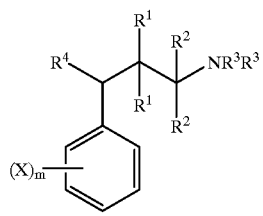

wherein X is independently selected from the group consisting of —H, —Br, —Cl, —F, —$CF_3$, alkyl, —OH, —$OCH_3$ —O-alkyl, and —O-acyl; R1 is independently selected from the group consisting of —H, alkyl, hydroxyalkyl, —OH, —O-alkyl, and —O-acyl; $R^2$ is independently selected from the group consisting of —H, alkyl, and hydroxyalkyl; $R^3$ is independently selected from the group consisting of —H and alkyl; $R^4$ is selected from the group consisting of alkyl and cycloalkyl, and m is independently an integer from 0 to 5; or the compounds of Formulas IV and V.

Formula IV

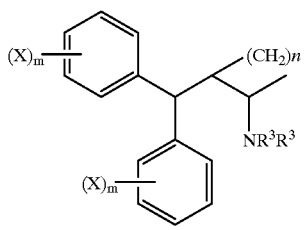

Formula V

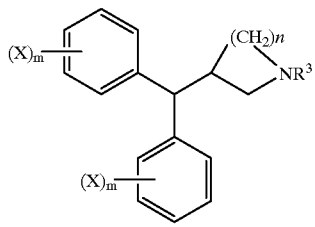

wherein n is an integer from 1 to 6; X is independently selected from the group consisting of —H, —Br, —Cl, —F, —CF$_3$, alkyl, —OH, —OCH$_3$, —O-alkyl, and —O-acyl; R$^3$ is independently selected from the group consisting of —H and alkyl; and m is independently an integer from 0 to 5; or the compounds of Formula VI and VII:

Formula VI

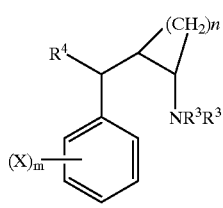

Formula VII

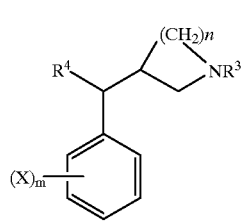

wherein n is an integer from 1 to 6; X is independently selected from the group consisting of —H, —Br, —Cl, —F, —CF$_3$, alkyl, —OH, —OCH$_3$, —O-alkyl, and —O-acyl; R$^3$ is independently selected from the group consisting of —H and alkyl; R$^4$ is selected from the group consisting of alkyl and cycloalkyl, and m is independently an integer from 0 to 5.

More preferred are those embodiments in which (X)$_m$ is independently selected from the group consisting of meta-fluoro, meta-chloro, ortho-methoxy, and ortho-methyl; NR$^3$ is selected from the group consisting of NH, N-methyl, and N-ethyl; NR$^3$R$^3$ is selected from the group consisting of NH$_2$, NH-methyl, and NH-ethyl; R$^1$ is selected from the group consisting of —H and methyl; and R$^2$ is selected from the group consisting of —H and methyl.

Especially preferred are those embodiments in which (X)m is meta-fluoro; NR$^3$ is selected from the group consisting of NH and N-methyl; and NR$^3$R$^3$ is selected from the group consisting of NH$_2$ and NH-methyl.

In further preferred embodiments, X is independently selected from the group consisting of —CF$_3$, and alkyl; R$^1$ is hydroxyalkyl; R$^2$ is hydroxyalkyl; R$^3$ is independently selected from the group consisting of —H, and alkyl; R$^4$ is selected from the group consisting of —H, alkyl, cycloalkyl, and

and m is independently an integer from 0 to 5.

These compounds are potentially useful in the present invention in place of the more complex Compounds 1, 2 and 3 above.

Examples of such simplified arylalkylamines include, but are not limited to, Compounds 19 through 69, whose structures are provided below.

Compound 19

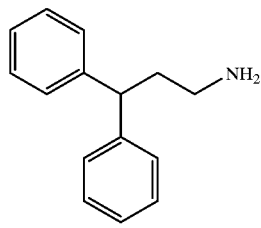

Compound 20

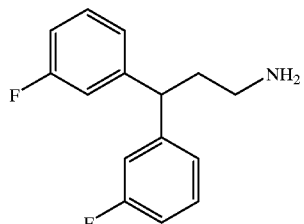

Compound 21

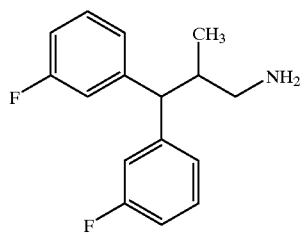

Compound 22

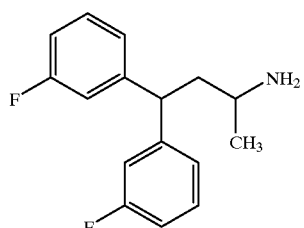

Compound 23
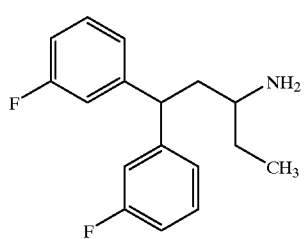
Compound 24
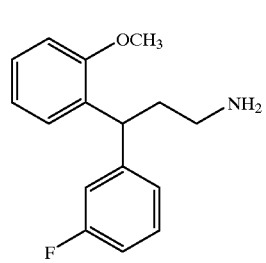
Compound 25
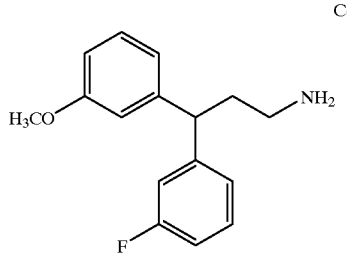
Compound 26
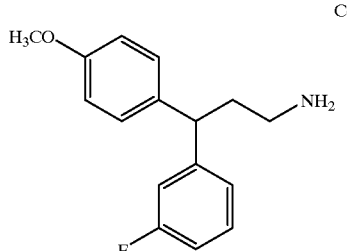
Compound 27
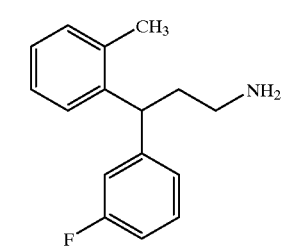
Compound 28
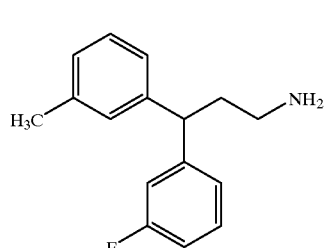
Compound 29
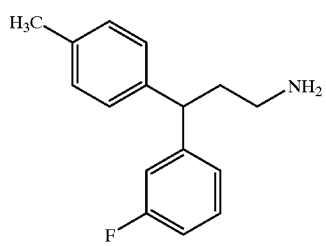
Compound 30
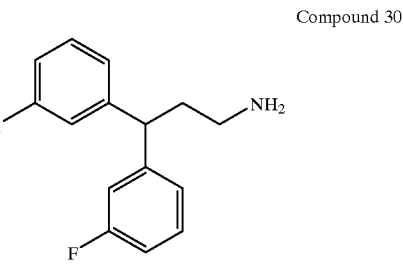
Compound 31
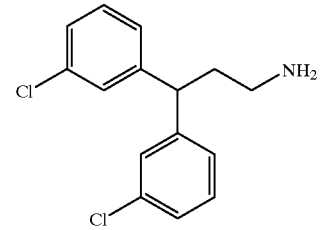
Compound 32
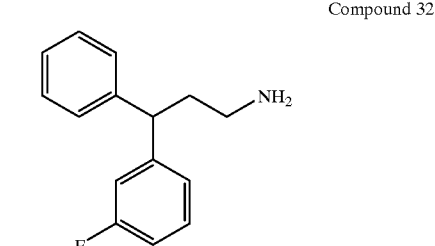
Compound 33
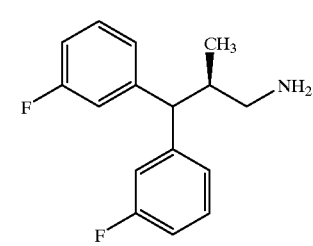
Compound 34
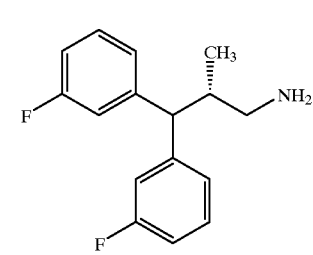

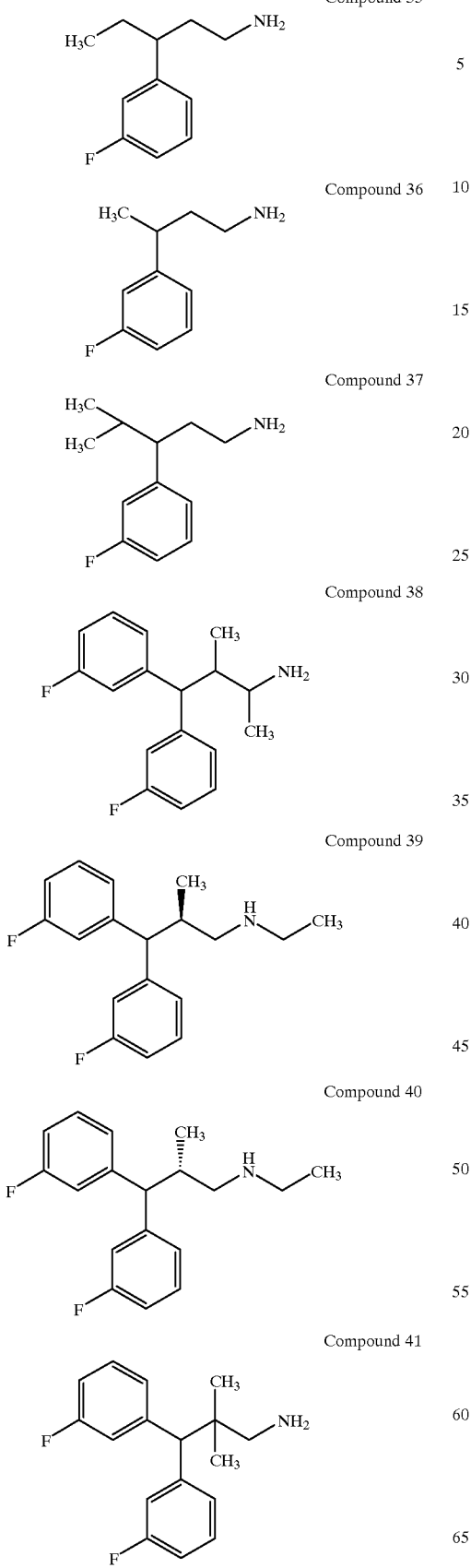

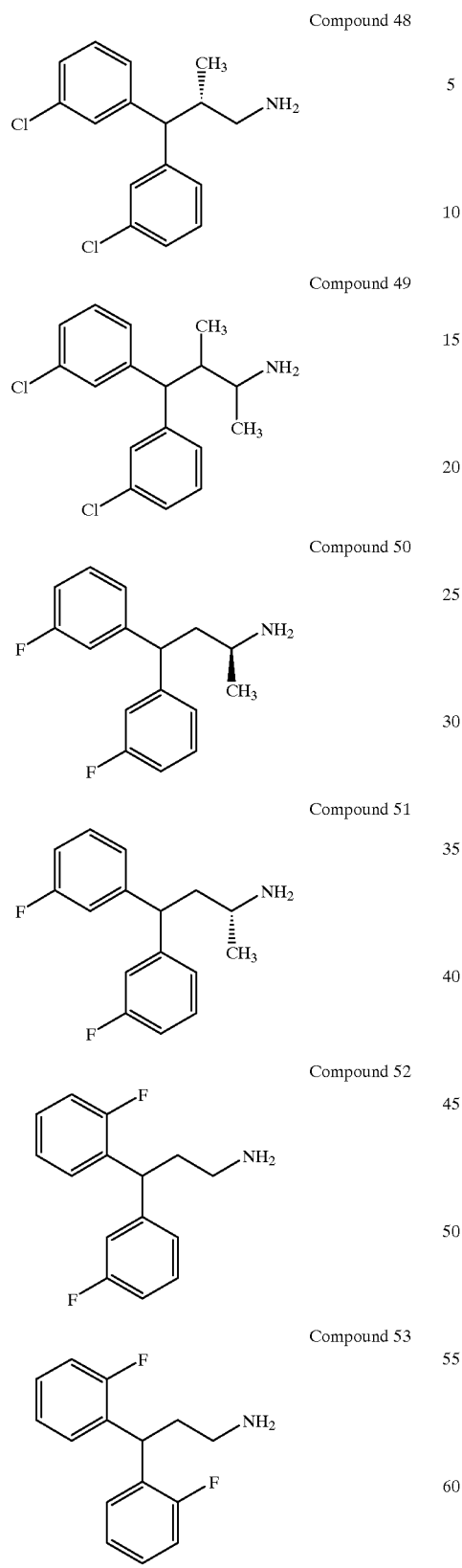
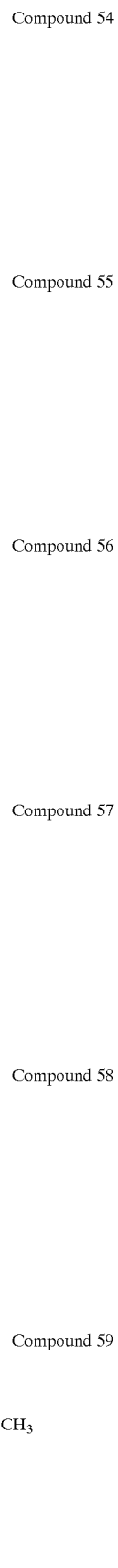

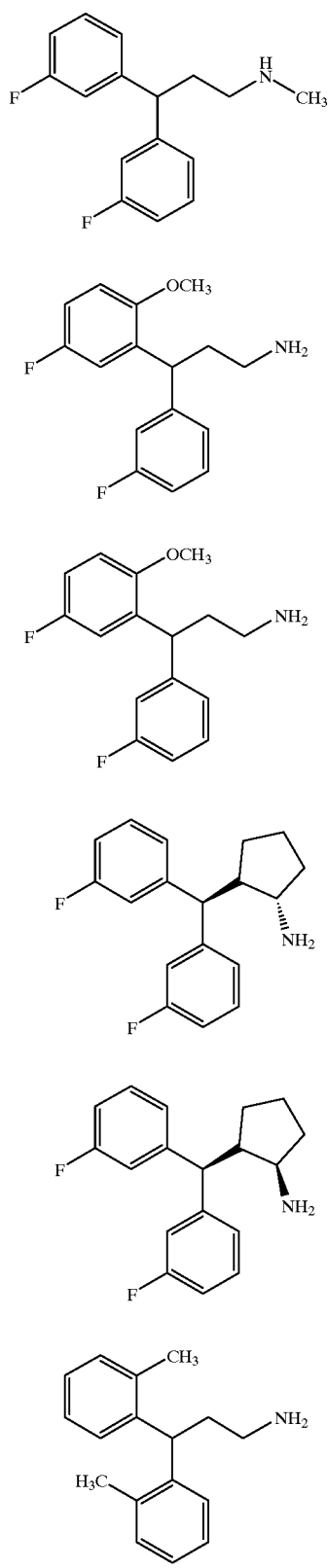
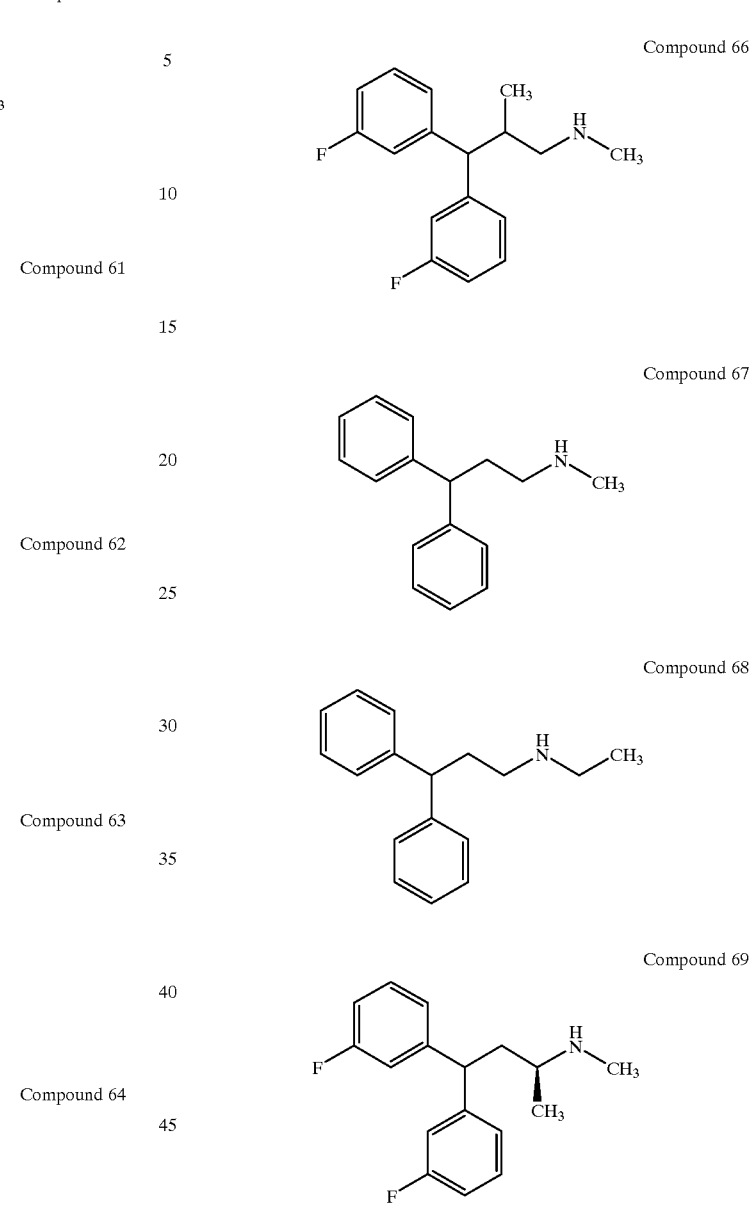

In preferred embodiments, the compound is selected from the group consisting of Compounds 20, 21, 22, 23, 24, 25, 26, 27, 28, 29, 30, 31, 32, 33, 34, 38, 39, 40, 41, 42, 43, 44, 45, 46, 47, 48, 49, 50, 51, 52, 53, 54, 55, 56, 57, 58, 59, 60, 61, 62, 63, 64, 65, 66, and 69.

In further preferred embodiments, the compound is selected from the group consisting of Compound 20, 21, 22, 23, 24, 25, 27, 28, 29, 30, 31, 32, 33, 34, 38, 39, 40, 41, 42, 43, 44, 45, 46, 47, 48, 49, 50, 51, 52, 53, 54, 55, 56, 57, 58, 59, 60, 61, 62, 63, 64, 65, 66, and 69.

In more preferred embodiments, the compound is selected from the group consisting of Compound 20, 24, 27, 30, 31, 33, 34, 46, 47, 48, 50, 57, 58, 60, 61, 62, 65, 66, and 69.

In particularly preferred embodiments, the compound is selected from the group consisting of Compound 20, 50, 60, and one of the enantiomers of Compound 21 (Compound 33 or 34).

In other preferred embodiments, the compound is selected from the group consisting of Compound 54, 55, 56, 57, 58, 59, 60, 61, 62, 63, 64, 65, 66, 67, 68, and 69.

EXAMPLE 23

Biological Activity of Compound 19 and Analogs

Compounds 19–69 had high potencies against NMDA-induced increases in $[Ca^{2+}]_i$ in rat cerebellar granule cells grown in culture (Table 1). The inhibitory effect of Compound 19 on responses to NMDA was noncompetitive. Compounds 19–69 inhibited [$^3$H]MK-801 binding in membranes prepared from rat hippocampal and cortical tissue (Table 1).

Compound 19 possessed the following additional biological activities: significant (p<0.05 compared to control) anticonvulsant activity against maximal electroshock-induced seizures in mice following i.p. administration ($ED_{50}$=26.4 mg/kg and $TD_{50}$ (rotorod)=43.8 mg/kg); significant anticonvulsant activity against maximal electroshock-induced seizures in mice following oral (p.o.) administration ($ED_{50}$=35 mg/kg), but with motor impairment at 30 mg/kg; significant analgesic activity in the hot-plate and PBQ-induced writhing assays at 16 mg/kg i.p.; no PCP-like stereotypic behavior (hyperexcitability and head weaving) at 30 mg/kg i.p. in rats; no generalization to PCP in the PCP discrimination assay at doses up to the behaviorally active dose of 30 mg/kg i.p. Compound 19 was significantly less potent in antagonizing increases in $[Ca^{2+}]_i$ elicited by depolarizing concentrations of KCl in rat cerebellar granule cells ($IC_{50}$=10.2 µM), and was without effect on blood pressure when administered s.c. in rats at doses up to 100 mg/kg. Compound 19, however, did block the induction of LTP in rat hippocampal slices when tested at 100 µM.

Compound 20 possessed the following additional biological activities: significant anticonvulsant activity against maximal electroshock-induced seizures in mice following i.p. administration ($ED_{50}$=20.1 mg/kg and $TD_{50}$ (rotorod)= 20.6 mg/kg); no significant anticonvulsant activity against maximal electroshock-induced seizures in mice following oral (p.o.) administration at doses up to 30 mg/kg, but with motor impairment at 30 mg/kg; significant anticonvulsant activity against sound-induced seizures in a genetically susceptible mouse model of reflex epilepsy (Frings mice) following i.p. ($ED_{50}$=2.1 mg/kg and $TD_{50}$=19.9 mg/kg) and oral ($ED_{50}$=9.7 mg/kg and $TD_{50}$=21.8 mg/kg) administration; significant anticonvulsant activity against maximal electroshock-induced seizures in rats following oral administration at the dose of 25 mg/kg, with no motor toxicity apparent at this dose; significant neuroprotectant activity in the rat model of temporary focal ischemia (a 51% reduction in the infarct volume following the administration of two doses of 1 mg/kg i.p., the first given immediately after middle cerebral artery occlusion and the second given 6 hr later; a 43% reduction in the infarct volume following the administration of two doses of 1 mg/kg i.p., the first given 2 hr after middle cerebral artery occlusion (i.e., at the time of reperfusion) and the second given 6 hr later); no significant analgesic activity at the dose of 25 mg/kg i.p. in the rat 52° C. hot plate test or the rat 48° C. tail flick test; significant analgesic activity, not blocked by the opiate receptor antagonist naloxone, in the rat formalin test at the dose of 10 mg/kg i.p.; significant analgesic activity, not blocked by naloxone, against acetic acid-induced abdominal writhing in mice at the dose of 10 mg/kg i.p.; no generalization to PCP in the PCP discrimination assay at doses up to the behaviorally active dose of 10 mg/kg i.p.; no neuronal vacuolization when administered at doses of 10 and 30 mg/kg i.p.; and no significant cardiovascular activity at doses up to 15 µmoles/ kg i.v. or 10 mg/kg i.p.

Compound 21 possessed the following additional biological activities: significant anticonvulsant activity against sound-induced seizures in a genetically susceptible mouse model of reflex epilepsy (Frings mice) following i.p. administration ($ED_{50}$=3.41 mg/kg and $TD_{50}$ (motor impairment)= 15.3 mg/kg).

The enantiomers of Compound 21 (Compounds 33 and 34, whose absolute stereochemistry has not been assigned at this time) possessed the following additional biological activities: Enantiomer #1: significant anticonvulsant activity against sound-induced seizures in a genetically susceptible mouse model of reflex epilepsy (Frings mice) following i.p. administration ($ED_{50}$=5 mg/kg and $TD_{50}$ (motor impairment)=28 mg/kg); significant anticonvulsant activity against maximal electroshock-induced seizures in rats following oral administration at the dose of 25 mg/kg, with no motor toxicity apparent at this dose; significant neuroprotectant activity in a rat model of focal ischemic stroke following i.p. administration of 2 mg/kg 30 min prior to vessel occlusion and 2 mg/kg 3 hr post-occlusion; no significant analgesic activity at the dose of 25 mg/kg i.p. in the rat 52° C. hot plate test or the rat 48° C. tail flick test; and no significant cardiovascular activity at doses up to 3 mg/kg i.v. Enantiomer #2: significant anticonvulsant activity against sound-induced seizures in a genetically susceptible mouse model of reflex epilepsy (Frings mice) following i.p. administration ($ED_{50}$=22 mg/kg and $TD_{50}$ (motor impairment) between 10 and 15 mg/kg).

Compound 22 possessed the following additional biological activities: significant anticonvulsant activity against sound-induced seizures in a genetically susceptible mouse model of reflex epilepsy (Frings mice) following i.p. ($ED_{50}$= 4.90 mg/kg and $TD_{50}$ (inverted grid)=26.8 mg/kg) and oral ($ED_{50}$=5.1 mg/kg and $LD_{50}$=18.3 mg/kg) administration; and no significant cardiovascular activity at doses up to 15 µmoles/kg (4.47 mg/kg) i.v.

Compound 50 (an enantiomer of Compound 22) possessed the following additional biological activities: significant anticonvulsant activity against sound-induced seizures in a genetically susceptible mouse model of reflex epilepsy (Frings mice) following i.p. administration ($ED_{50}$=3 mg/kg and $TD_{50}$ (motor impairment)=17 mg/kg); significant neuroprotectant activity in a rat model of focal ischemic stroke following i.p. administration of 2 mg/kg 30 min prior to vessel occlusion and 2 mg/kg 3 hr post-occlusion; no significant analgesic activity at the dose of 25 mg/kg i.p. in the rat 52° C. hot plate test or the rat 48° C. tail flick test; and no significant cardiovascular activity at doses up to 5 mg/kg i.v.

Compound 51 (an enantiomer of Compound 22) possessed the following additional biological activities: significant anticonvulsant activity against sound-induced seizures in a genetically susceptible mouse model of reflex epilepsy (Frings mice) following i.p. administration ($ED_{50}$=9 mg/kg and $TD_{50}$ (motor impairment)=14 mg/kg).

Compound 24 possessed the following additional biological activities: significant anticonvulsant activity against sound-induced seizures in a genetically susceptible mouse model of reflex epilepsy (Frings mice) following i.p. administration ($ED_{50}$=5 mg/kg and $TD_{50}$ (motor impairment)=16 mg/kg); no significant neuroprotectant activity in a rat model of focal ischemic stroke following i.p. administration of 2 mg/kg 30 min prior to vessel occlusion and 2 mg/kg 3 hr post-occlusion; and no significant cardiovascular activity at doses up to 10 mg/kg i.v.

Compound 31 possessed the following additional biological activities: significant anticonvulsant activity against sound-induced seizures in a genetically susceptible mouse model of reflex epilepsy (Frings mice) following i.p. administration ($ED_{50}$=6 mg/kg and $TD_{50}$ (motor impairment) between 10 and 20 mg/kg).

Compound 46 possessed the following additional biological activities: significant anticonvulsant activity against sound-induced seizures in a genetically susceptible mouse model of reflex epilepsy (Frings mice) following i.p. administration ($ED_{50}$=25 mg/kg and $TD_{50}$ (motor impairment) between 18 and 21 mg/kg); and no significant neuroprotectant activity in a rat model of focal ischemic stroke following i.p. administration of 2 mg/kg 30 min prior to vessel occlusion and 2 mg/kg 3 hr post-occlusion.

Compound 57 possessed the following additional biological activities: significant anticonvulsant activity against sound-induced seizures in a genetically susceptible mouse model of reflex epilepsy (Frings mice) following i.p. administration ($ED_{50}$=1 mg/kg and $TD_{50}$ (motor impairment) between 6 and 8 mg/kg).

Compound 58 possessed the following additional biological activities: significant anticonvulsant activity against sound-induced seizures in a genetically susceptible mouse model of reflex epilepsy (Frings mice) following i.p. administration ($ED_{50}$=0.9 mg/kg and $TD_{50}$ (motor impairment)= 14.5 mg/kg); no significant neuroprotectant activity in a rat model of focal ischemic stroke following i.p. administration of 2 mg/kg 30 min prior to vessel occlusion and 2 mg/kg 3 hr post-occlusion; and no significant cardiovascular activity at doses up to 2 mg/kg i.v.

Compound 59 possessed the following additional biological activities: significant anticonvulsant activity against sound-induced seizures in a genetically susceptible mouse model of reflex epilepsy (Frings mice) following i.p. administration ($ED_{50}$=2.7 mg/kg and $TD_{50}$ (motor impairment)= 7.8 mg/kg); no significant neuroprotectant activity in a rat model of focal ischemic stroke following i.p. administration of 2 mg/kg 30 min prior to vessel occlusion and 2 mg/kg 3 hr post-occlusion; and no significant cardiovascular activity at doses up to 10 mg/kg i.v.

Compound 60 possessed the following additional biological activities: significant neuroprotectant activity in a rat model of focal ischemic stroke following i.p. administration of 2 mg/kg 30 min prior to vessel occlusion and 2 mg/kg 3 hr post-occlusion.

Taken together, the results obtained with these simplified synthetic arylalkylamines suggest that such simplified molecules do not interact specifically with the arylalkylamine binding site on receptor-operated $Ca^{2+}$ channels as do Compounds 1, 2 and 3. Specifically, Compounds 19–69 bind to the site labeled by [$^3$H]MK-801 at concentrations ranging approximately 1 to 400-fold higher than those which antagonize the function of the NMDA receptor-ionophore complex. The fact that Compounds 19–69 at therapeutic doses do not produce PCP-like stereotypic behavior, substitute for PCP in drug discrimination assays, or elicit neuronal vacuolization suggests, however, that such compounds might be useful either as lead compounds or drug candidates for neurological disorders and diseases. It has been reported that compounds which bind with low affinity (relative to MK-801) to the site labeled by [$^3$H]MK-801 might possess therapeutic utility and possess a more favorable side effect profile than that possessed by a high affinity antagonist such as MK-801 itself (Rogawski, Therapeutic potential of excitatory amino acid antagonists: channel blockers and 2,3-benzodiazepines. Trends Pharmacol. Sci. 14: 325, 1993). The low affinity of certain compounds within the group of Compounds 19–69 (relative to MK-801) for the site labeled by [$^3$H]MK-801 may place these compounds into this general class of low affinity noncompetitive antagonists.

Identification of a Novel Modulatory Site on Receptor-operated Calcium Channels

Having identified arylalkylamines which have therapeutically useful properties as defined above, compounds can now be identified which act at the critical arylalkylamine binding site on receptor-operated $Ca^{2+}$ channels, such as those present within NMDA, AMPA and nicotinic cholinergic receptor-ionophore complexes.

Examples of suitable tests now follow:

EXAMPLE 24

Radioligand Binding in Rat Cortex or Cerebellum

The following assay can be utilized as a high throughput assay to screen product libraries (e.g., natural product libraries and compound files at major pharmaceutical companies) to identify new classes of compounds with activity at this unique arylalkylamine site. These new classes of compounds are then utilized as chemical lead structures for a drug development program targeting the arylalkylamine binding site on receptor-operated $Ca^{2+}$ channels. The compounds identified by this assay offer a novel therapeutic approach to treatment of neurological disorders or diseases. Examples of such compounds include those provided in the generic chemical formulae above. Routine experiments can be performed to identify those compounds having the desired activities.

Rat brain membranes are prepared according to the method of Williams et al. (Effects of polyamines on the binding of [$^3$H]MK-801 to the NMDA receptor: Pharmacological evidence for the existence of a polyamine recognition site. Molec. Pharmacol. 36: 575, 1989) with the following alterations; Male Sprague-Dawley rats (Harlan Laboratories) weighing 100–200 g are sacrificed by decapitation. The cortex or cerebellum from 20 rats are cleaned and dissected. The resulting brain tissue is homogenized at 4° C. with a polytron homogenizer at the lowest setting in 300 ml 0.32 M sucrose containing 5 mM K-EDTA (pH 7.0). The homogenate is centrifuged for 10 min at 1,000×g and the supernatant removed and centrifuged at 30,000×g for 30 minutes. The resulting pellet is resuspended in 250 ml 5 mM K-EDTA (pH 7.0) stirred on ice for 15 min, and then centrifuged at 30,000×g for 30 minutes. The pellet is resuspended in 300 ml 5 mM K-EDTA (pH 7.0) and incubated at 32° C. for 30 min. The suspension is then centrifuged at 100,000×g for 30 min. Membranes are washed by resuspension in 500 ml 5 mM K-EDTA (pH 7.0), incubated at 32° C. for 30 min, and centrifuged at 100,000×g for 30 minutes. The wash procedure, including the 30 min incubation, is repeated. The final pellet is resuspended in 60 ml 5 mM K-EDTA (pH 7.0) and stored in aliquots at –80° C. The extensive washing procedure utilized in this assay was designed in an effort to minimize the concentrations of glutamate and glycine (co-agonists at the NMDA receptor-ionophore complex) present in the membrane preparation.

To perform a binding assay with [$^3$H]arylalkylamine, aliquots of SPMs (Synaptic Plasma Membranes) are thawed, resuspended in 30 mls of 30 mM EPPS/1 mM K-EDTA, pH 7.0, and centrifuged at 100,000×g for 30 minutes. SPMs are resuspended in buffer A (30 mM EPPS/1 mM K-EDTA, pH 7.0). The [$^3$H]arylalkylamine is added to this reaction mixture. Binding assays are carried out in polypropylene test tubes. The final incubation volume is 500 µl. Nonspecific binding is determined in the presence of 100 μM nonradioactive arylalkylamine. Duplicate samples are incubated at 0° C. for 1 hour. Assays are terminated by the addition of 3 ml of ice-cold buffer A, followed by filtration over glass-fiber filters (Schleicher & Schuell No. 30) that are presoaked in 0.33% polyethyleneimine (PEI). The filters are washed with another 3×3 ml of buffer A, and radioactivity is determined by scintillation counting at an efficiency of 35–40% for 3H.

In order to validate the above assay, the following experiments are also performed:

(a) The amount of nonspecific binding of the [$^3$H] arylalkylamine to the filters is determined by passing 500 μl of buffer A containing various concentrations of [$^3$H]arylalkylamine through the presoaked glass-fiber filters. The filters are washed with another 4×3 ml of buffer A, and radioactivity bound to the filters is determined by scintillation counting at an efficiency of 35–40% for $^3$H. In filters that are not pretreated with 0.33% PEI, it was found that 87% of the $^3$H-ligand was bound to the filter. Presoaking with 0.33% PEI reduces the nonspecific binding to 0.5–1.0% of the total ligand added.

(b) A saturation curve is constructed by resuspending SPMs in buffer A. The assay buffer (500 μl) contains 60 μg of protein. Concentrations of [$^3$H]arylalkylamine are used, ranging from 1.0 nM to 400 μM in half-log units. A saturation curve is constructed from the data, and an apparent $K_D$ value and $B_{max}$ value determined by Scatchard analysis (Scatchard, The attractions of proteins for small molecules and ions. *Ann. N. Y. Acad. Sci.* 51:660, 1949). The cooperativity of binding of the [$^3$H]arylalkylamine is determined by the construction of a Hill plot (Hill, A new mathematical treatment of changes of ionic concentrations in muscle and nerve under the action of electric currents, with a theory to their mode of excitation. *J. Physiol.* 40:190, 1910).

(c) The dependence of binding on protein (receptor) concentration is determined by resuspending SPMs in buffer A. The assay buffer (500 μl) contains a concentration of [$^3$H]arylalkylamine equal to its $K_D$ value and increasing concentrations of protein. The specific binding of [$^3$H]arylalkylamine should be linearly related to the amount of protein (receptor) present.

(d) The time course of ligand-receptor binding is determined by resuspending SPMs in buffer A. The assay buffer (500 μl) contains a concentration of [$^3$H] arylalkylamine equal to its $K_D$ value and 100 μg of protein. Duplicate samples are incubated at 0° C. for varying lengths of time; the time at which equilibrium is reached is determined, and this time point is routinely used in all subsequent assays.

(e) The pharmacology of the binding site can be analyzed by competition experiments. In such experiments, the concentration of [$^3$H]arylalkylamine and the amount of protein are kept constant, while the concentration of test (competing) drug is varied. This assay allows for the determination of an $IC_{50}$ and an apparent $K_D$ for the competing drug (Cheng and Prusoff, Relationship between the inhibition constant ($K_i$) and the concentration of inhibitor which causes 50 percent inhibition ($IC_{50}$) of an enzymatic reaction. *J. Biochem. Pharmacol.* 22:3099, 1973). The cooperativity of binding of the competing drug is determined by Hill plot analysis.

Specific binding of the [$^3$H]arylalkylamine represents binding to a novel site on receptor-operated $Ca^{2+}$ channels such as those present within NMDA-, AMPA- and nicotinic cholinergic receptor-ionophore complexes. As such, other arylalkylamines should compete with the binding of [$^3$H] arylalkylamine in a competitive fashion, and their potencies in this assay should correlate with their inhibitory potencies in a functional assay of receptor-operated $Ca^{2+}$ channel antagonism (e.g., inhibition of NMDA receptor-induced increases in $[Ca^{2+}]_i$ in cultures of rat cerebellar granule cells). Conversely, compounds which have activity at the other known sites on receptor-operated $Ca^{2+}$ channels (e.g., MK-801, $Mg^{2+}$, polyamines) should not displace [$^3$H] arylalkylamine binding in a competitive manner. Rather, complex allosteric modulation of [$^3$H]arylalkylamine binding, indicative of noncompetitive interactions, might be expected to occur. In preliminary experiments, MK-801 did not displace [$^3$H]arylalykylamine binding at concentrations up to 100 μM.

(f) Studies to estimate the dissociation kinetics are performed by measuring the binding of [$^3$H] arylalkylamine after it is allowed to come to equilibrium (see (d) above), and a large excess of nonradioactive competing drug is added to the reaction mixture. Binding of the [$^3$H]arylalkylamine is then assayed at various time intervals. With this assay, the association and dissociation rates of binding of the [$^3$H]arylalkylamine are determined (Titeler, *Multiple Dopamine Receptors: Receptor Binding Studies in Dopamine Pharmacology*. Marcel Dekker, Inc., New York, 1983). Additional experiments involve varying the reaction temperature (0° C. to 37° C.) in order to understand the temperature dependence of this parameter.

Example 25

Radioligand Binding in Cerebellar Granule Cells

Primary cultures of cerebellar granule neurons are obtained from 8-day-old rats and plated onto squares of Aclar plastic coated with poly-L-lysine. The plastic squares are placed in 24-well culture plates, and approximately $7.5 \times 10^5$ granule cells are added to each well. Cultures are maintained in Eagles' medium (HyClone Laboratories) containing 25 mM KCl, 10% fetal calf serum (HyClone Laboratories), 2 mM glutamine, 100 μg/ml gentamicin, 50 U/ml penicillin, and 50 μg/ml streptomycin at 37° C. in a humid atmosphere of 5% $CO_2$ in air for 24 hr before the addition of cytosine arabinoside (10 μM, final). No changes of culture medium are made until the cells are used for receptor binding studies 6–8 days after plating.

To perform a binding assay with [$^3$H]arylalkylamine, the reaction mixture consists of 200 μl of buffer A (20 mM K-HEPES, 1 mM K-EDTA, pH 7.0) in each well of the 24-well plate. The [$^3$H]arylalkylamine is added to this reaction mixture. Nonspecific binding is determined in the presence of 100 μM nonradioactive arylalkylamine. Triplicate samples are incubated at 0° C. for 1 hour. Assays are terminated by manually scraping the cells off the Aclar squares and placing them into polypropylene test tubes. The membranes prepared from whole cells in this manner are suspended in 10 ml of ice-cold buffer A, and filtered over glass-fiber filters (Schleicher & Schuell No. 30) that are presoaked in 0.33% PEI. The filters are washed with another 3×3 ml of buffer A, and radioactivity on the filters is determined by scintillation counting at an efficiency of 35–40% for $^3$H. The assay may be terminated by centrifugation rather than filtration in order to minimize nonspecific binding.

Specific experiments to characterize and validate the assay are performed essentially as above, except that cells are used in place of membranes for the initial binding. The binding assay allows for the determination of an $IC_{50}$ value and an apparent $K_D$ for the competing drug as described by Scatchard analysis (The attractions of proteins for small molecules and ions. *Ann. N. Y. Acad. Sci.* 51: 660, 1949). Cooperativity of binding of the competing drug is determined by Hill plot analysis (A new mathematical treatment of changes of ionic concentrations in muscle and nerve under the action of electric currents, with a theory to their mode of excitation. *J. Physiol.* 40:190, 1910). The specific binding of the [$^3$H]arylalkylamine represents binding to a novel site on receptor-operated calcium channels.

Example 26

Recombinant Receptor Binding Assay

The following is one example of a rapid screening assay for useful compounds of this invention. In this assay, a cDNA or gene clone encoding the arylalkylamine binding site (receptor) from a suitable organism such as a human is obtained using standard procedures. Distinct fragments of the clone are expressed in an appropriate expression vector to produce the smallest polypeptide(s) obtainable from the receptor which retain the ability to bind Compound 1, Compound 2 or Compound 3. In this way, the polypeptide(s) which includes the novel arylalkylamine receptor for these compounds can be identified. Such experiments can be facilitated by utilizing a stably transfected mammalian cell line (e.g., HEK 293 cells) expressing the arylalkylamine receptor.

Alternatively, the arylalkylamine receptor can be chemically reacted with chemically modified Compound 1, Compound 2 or Compound 3 in such a way that amino acid residues of the arylalkylamine receptor which contact (or are adjacent to) the selected compound are modified and thereby identifiable. The fragment(s) of the arylalkylamine receptor containing those amino acids which are determined to interact with Compound 1, Compound 2 or Compound 3 and are sufficient for binding to said molecules, can then be recombinantly expressed, as described above, using a standard expression vector(s).

The recombinant polypeptide(s) having the desired binding properties can be bound to a solid phase support using standard chemical procedures. This solid phase, or affinity matrix, may then be contacted with Compound 1, Compound 2 or Compound 3 to demonstrate that those compounds can bind to the column, and to identify conditions by which the compounds may be removed from the solid phase. This procedure may then be repeated using a large library of compounds to determine those compounds which are able to bind to the affinity matrix, and then can be released in a manner similar to Compound 1, Compound 2 or Compound 3. However, alternative binding and release conditions may be utilized in order to obtain compounds capable of binding under conditions distinct from those used for arylalkylamine binding (e.g., conditions which better mimic physiological conditions encountered especially in pathological states). Those compounds which do bind can thus be selected from a very large collection of compounds present in a liquid medium or extract.

Once compounds able to bind to the arylalkylamine binding polypeptide(s) described above are identified, those compounds can then be readily tested in the various assays described above to determine whether they, or simple derivatives thereof, are useful compounds for therapeutic treatment of neurological disorders and diseases described above.

In an alternate method, native arylalkylamine receptor can be bound to a column or other solid phase support. Those compounds which are not competed off by reagents which bind other sites on the receptor can then be identified. Such compounds define novel binding sites on the receptor. Compounds which are competed off by other known compounds thus bind to known sites, or bind to novel sites which overlap known binding sites. Regardless, such compounds may be structurally distinct from known compounds and thus may define novel chemical classes of agonists or antagonist which may be useful as therapeutics. In summary, a competition assay can be used to identify useful compounds of this invention.

Example 27

Patch-clamp Electrophysiology Assay

The following assay is performed for selected compounds identified in the above-mentioned radioligand binding assays as interacting in a highly potent and competitive fashion at the novel arylalkylamine binding site on receptor-operated $Ca^{2+}$ channels, such as those present in NMDA-, AMPA- or nicotinic cholinergic receptor-ionophore complexes. This patch-clamp assay provides additional relevant data about the site and mechanism of action of said previously selected compounds. Specifically, the following pharmacological and physiological properties of the compounds interacting at the arylalkylamine binding site are determined, utilizing the NMDA receptor-ionophore complex as an example of receptor-operated $Ca^{2+}$ channels: potency and efficacy at blocking NMDA receptor-mediated ionic currents, the noncompetitive nature of block with respect to glutamate and glycine, use-dependence of action, voltage-dependence of action, both with respect to onset and reversal of blocking, the kinetics of blocking and unblocking (reversal), and open-channel mechanism of blocking. Such data confirm that the compounds interacting at the arylalkylamine binding site retain the unique biological profile of the arylalkylamines, and do not have their primary activity at the known sites on the NMDA receptor-ionophore complex (glutamate binding site, glycine binding site, MK-801 binding site, $Mg^{2+}$ binding site, $Zn^{2+}$ binding site, sigma binding site, polyamine binding site).

Patch-clamp recordings of mammalian neurons (hippocampal, cortical, cerebellar granule cells) are carried out utilizing standard procedures (Donevan et al., Arcaine blocks N-methyl-D-aspartate receptor responses by an open channel mechanism: whole-cell and single-channel recording studies in cultured hippocampal neurons. *Molec. Pharmacol.* 41: 727, 1992; Rock and Macdonald, Spermine and related polyamines produce a voltage-dependent reduction of NMDA receptor single-channel conductance. *Molec. Pharmacol.* 42:157, 1992).

Alternatively, patch-clamp experiments can be performed on Xenopus oocytes or on a stably transfected mammalian cell line (e.g., HEK 293 cells) expressing specific subunits of receptor-operated $Ca^{2+}$ channels. In this manner, for example, potency and efficacy at various glutamate receptor subtypes (e.g., NMDAR1, NMDAR2A through NMDAR2D, GluR1 through GluR4) can be determined. Further information regarding the site of action of the arylalkylamines on these glutamate receptor subtypes can be obtained by using site-directed mutagenesis.

Example 28

Synthesis of Arylalkylamines

Arylalkylamines such as Compound 1, Compound 2 and Compound 3 are synthesized by standard procedures (Jasys et al., The total synthesis of argiotoxins 636, 659 and 673. *Tetrahedron Lett.* 29:6223, 1988; Nason et al., Synthesis of neurotoxic Nephila spider venoms: NSTX-3 and JSTX-3. *Tetrahedron Lett.* 30:2337, 1989). Specific examples of syntheses of arylalkylamine analogs are provided below.

Synthesis of Compound 4 was accomplished as follows:

A solution of 1,4-diaminobutane (203.4 g, 2.312 mol) in methanol (50 ml) was treated with acrylonitrile (AN, 135 g, 2.543 mol) at a rate of 40 ml/h. The reaction was stirred 16 hr at room temperature (20°–25° C.). GC/MS showed 64% of the product A; GC/MS ($R_t$=4.26 min) m/z (relative intensity) 141 ($M^+$, 4), 124 (8), 101 (42), 83 (100), 70 (65), 56 (63), 42 (81), and 36% of the di-addition product B; GC/MS ($R_t$=7.50 min) m/z (relative intensity) 194 ($M^+$, 13), 154 (23), 123 (45), 96 (15), 83 (100), 70 (24), 56 (29), 42 (40). Kugelrohr distillation afforded 120 g (37%) of the product A, as a clear oil.

A solution of 3-bromo-1-propylamine hydrobromide (102.4 g, 468 mmol) and di-tert-butyldicarbonate (100.1 g, 462 mmol) in DMF (600 ml) was treated with triethylamine (70 ml, 500 mmol) and the reaction stirred 1 hr at room temperature. The reaction was transferred to a separatory funnel containing 500 ml $H_2O$ and 500 ml diethyl ether. The mixture was equilibrated and the aqueous layer removed. The ether layer was washed with 1% HCl (3x), dried over $K_2CO_3$ and reduced to afford 105 g (95%) of the product C.

A solution of A (80 g, 567 mmol) and KF-Celite (137 g, 50 wt % on Celite) in acetonitrile (1 L) was treated with the bromide C (105 g, 444 mmol) in acetonitrile (100 ml) over 1 hr. The reaction was then stirred at 50° C. for 24 hr. GC/MS showed that the bromide C had been consumed. The reaction was cooled, filtered and concentrated to a oil. This material was dissolved in ether (500 ml) and equilibrated with water (500 ml). The ether layer was removed and the aqueous phase washed with ether (4×500 ml) and once with ether-dichloromethane (1:1, 500 ml). This procedure separated unreacted nitrile (aqueous fraction) from the product D. The organic washes were combined and concentrated to afford 120 g of an oil. This material was applied to a silica column (1500 $cm^3$ of dry silica) in hexane-dichloromethane (1:1) and washed (300 ml/min) with a complex gradient of hexane-dichloromethane (1:1) to dichloromethane to methanol-dichloromethane (1:9) to methanol-dichloromethane-isopropylamine (10:90:1). Like fractions (TLC analysis) were combined and concentrated to afford 93 g (70% from the bromide C) of the product D. $^{13}$C-NMR (CDCl$_3$) gave d 155.8, 118.5, 77.7, 49.3, 48.6, 47.3, 44.7, 38.7, 29.6, 28.1, 27.4, 27.3, 18.3, which were consistent with literature values.

A solution of D (93 g, 312 mmol) in dichloromethane (200 ml) was treated with di-tert-butyldicarbonate (80 g, 367 mmol) at a rate which gave a vigorous reflux. The reaction was stirred 16 hr at room temperature and adsorbed onto 300 $cm^3$ of silica. This was concentrated to dryness, in vacuo, and applied to the top of a silica column (10 cm i.d. containing 1000 cm3 dry silica). The column was washed with a gradient of hexane to ethyl acetate-hexane (3:2). Like fractions were combined and concentrated to afford 89 g (49%) of the product E.

A solution of E (89 g, 179 mmol) and palladium dihydroxide (20 g) in acetic acid (300 ml) was hydrogenated at 55 psi hydrogen for 2 hr at room temperature. The reaction was filtered and concentrated to a thick oil. This material was dissolved in dichloromethane and treated with 1 N NaOH until the pH of the equilibrated phases was basic (pH 14). The dichloromethane was removed and the aqueous layer washed an additional three times with dichloromethane. The organic washes were combined, dried, and concentrated to an oil. Chromatography (silica) using a gradient of dichloromethane to methanol-dichloromethane-isopropylamine (10:90:1) afforded 55 g (61%) of the product F.

Chain extension was repeated as above. A solution of F (55 g, 110 mmol) in methanol was treated with acrylonitrile (6.1 g, 116 mmol) and stirred at room temperature until the reaction was complete, as indicated by TLC analysis. The reaction was concentrated, dissolved in dichloromethane and treated with di-tert-butyl dicarbonate (26.4 g, 121 mmol). The reaction was stirred at room temperature until complete and the product purified by chromatography (silica) with a gradient of hexane to ethyl acetate-hexane (3:2). This afforded 32 g (49%) of pure G and 23 g of semi-pure material (containing primarily G). A solution of G (32 g, 49 mmol) and palladium dihydroxide (32 g) in acetic acid (300 ml) was hydrogenated at 55 psi hydrogen for 2 hr at room temperature. The reaction was processed in the same fashion as for the reaction yielding F. This afforded 24 g (33% from F) of the product H. Chain extension was repeated, as above, to afford 21 g (70%) of the polyamine I.

A solution of 5-fluoroindole-3-acetic acid (2 g, 10.4 mmol) and p-nitrophenol (1.6 g, 11.6 mmol) in dichloromethane (250 ml) was treated with DCC (2.4 g, 11.6 mmol) and the reaction stirred 24 hr at room temperature. The reaction mixture was filtered directly into a stirred solution of the polyamine I (21 g, 25 mmol) in dichloromethane. The reaction was stirred 4 hr at room temperature and chromatographed (silica) using a gradient of dichloromethane to methanol-dichloromethane-isopropylamine (50:950:1) to afford 8.7 g (85% from the starting indole) of the product J.

A solution of j (8.7 g, 8.8 mmol) in acetonitrile (1.8 L) was treated with concentrated HCl (200 ml) and the reaction stirred under argon for 4 hr at room temperature. The reaction was filtered and the precipitate collected to afford 5.53 g (93%) of Compound 4. The material was found to be 98.7% pure by analytical RP-HPLC. $UV_{max}$ (0.1% TFA) 284 nm (e 6140).

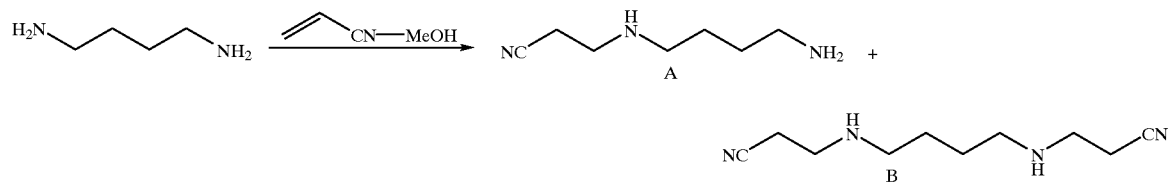

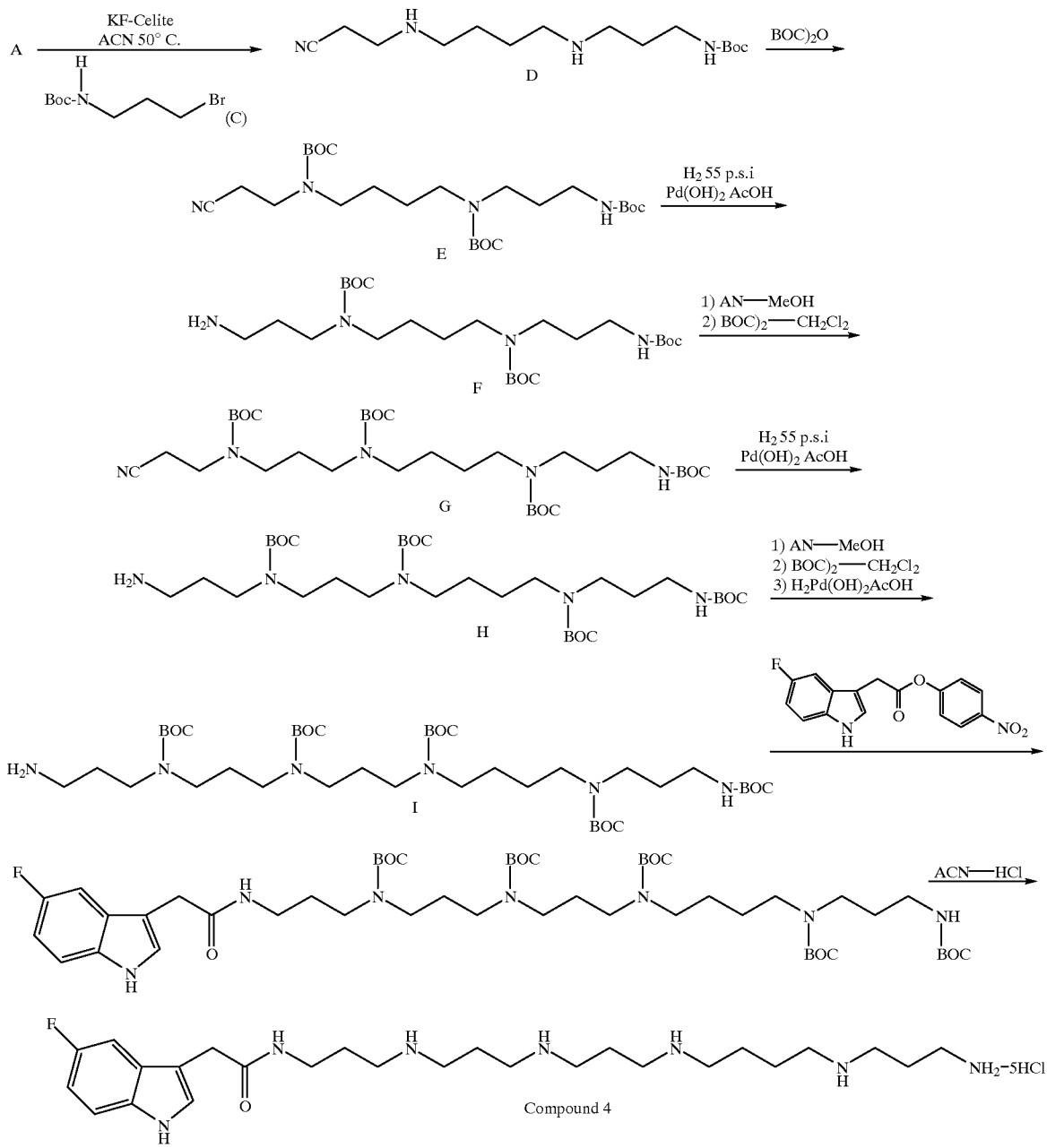

Compound 4

Synthesis of Compound 5 was accomplished as follows. Compound 6, 7, 8 and 10 were prepared in an analogous manner except as described below.

To a solution of diaminopentane (49 g, 0.48 moles) and triethylamine (48 g, 0.43 moles) in 200 ml of dioxane was added a solution of di-tert-butyl dicarbonate (53.4 g, 0.24 moles in 200 ml of dichloromethane) over a period of 30 minutes. The reaction was stirred for another 2 hours, followed by removal of the solvents in vacuo. The resulting solid was taken up in ether, washed 3 x with 50 mM sodium hydroxide, 1 x with brine, dried over sodium sulfate and concentrated in vacuo. The resulting oil was issolved in 20% ethyl acetate/hexane and applied to a 9 cm×20 cm silica column. The column was eluted with 20% to 35% ethyl acetate/hexane followed by 5% ethanol/chloroform, and finally by 5% ethanol/5% isopropylamine/chloroform. The fractions (eluted with the final solvent) which contained product (identified by GC/MS) were pooled and concentrated in vacuo to yield 20.1 g of compound A.

Benzaldehyde (11 g, 0.104 moles) and compound A (20.1 g, 0.099 moles) were mixed together and swirled. After 20 minutes 20 ml of absolute ethanol were added and stirred for another 10 minutes followed by removal of the ethanol and water in vacuo. The oil was taken up in 50 ml of dry ethanol to which sodium borohydride (3.74 g, 0.099 moles) was added. The reaction was stirred overnight at room temperature. The solvent was removed in vacuo, and the residue was taken up in ether and 50 mM sodium hydroxide. The water layer was separated and the ether layer was washed 2 x with 50 mM sodium hydroxide, 1 x with brine, dried over sodium sulfate, and concentrated in vacuo to yield 28.8 g (99%) of compound B.

Compound B (28.8 g, 0.0985 moles) was dissolved in 400 ml of acetonitrile followed by addition of potassium fluoride/Celite (22.9 g, 0.197 moles) and N-(3-bromopropyl) phthalimide (39.61 g, 0.147 moles). The reaction was heated to reflux under argon for 10.5 hours. After cooling, the reaction was filtered and the solid washed with acetonitrile. The combined acetonitrile solutions were concentrated in vacuo to yield a thick yellow oil. The oil was taken up in 1 L of ethanol to which 9.3 ml of hydrazine were added. The solution was heated to reflux under argon for 2.25 hours. The solvent was removed in vacuo, and the residue was taken up in ether and 50 mM sodium hydroxide. The ether layer was separated, dried over sodium sulfate and stripped in vacuo to yield 33.4 g of crude compound C. The crude material was chromatographed on a 9 cm×30 cm silica column eluted with dichloromethane/methanol/isopropylamine (94:5:1) to give 26.9 g of compound C.

Benzaldehyde (8.54 g, 0.081 moles) and compound C (26.9 g, 0.0767 moles) were mixed together and swirled. After 30 minutes 20 ml of absolute ethanol were added and stirred for another 45 minutes followed by removal of the ethanol and water in vacuo. The oil was taken up in 80 ml of dry ethanol to which sodium borohydride (2.9 g, 0.0767 moles) was added. The reaction was stirred overnight at room temperature. The solvent was removed in vacuo, and the residue was taken up in ether and 50 mM sodium hydroxide. The water layer was separated and the ether layer was washed 2 x with 50 mM sodium hydroxide, 1 x with brine, dried over potassium carbonate, and concentrated in vacuo to yield 32.6 g (96%) of compound D.

Compound D (32.6 g, 0.0742 moles) was dissolved in 300 ml of acetonitrile followed by addition of potassium fluoride/Celite (17.24 g, 0.148 moles) and N-(3-bromopropyl)phthalimide (29.83 g, 0.111 moles). The reaction was heated to reflux under argon for 15.25 hours. After cooling, the reaction was filtered and the solid washed with acetonitrile. The combined acetonitrile solutions were stripped in vacuo. The oil was taken up in 750 ml of ethanol to which 7 ml of hydrazine were added. The solution was heated to reflux under argon for 2 hours. The solvent was removed in vacuo, and the residue was taken up in ether and 50 mM sodium hydroxide. The ether layer was separated, dried over sodium sulfate and stripped in vacuo. The crude material was chromatographed on a 9 cm×30 cm silica column eluted with dichloromethane/methanol/isopropylamine (94:5:1) to give 31.9 g of compound E.

Compound E (18.22 g, 36.7 mmoles) and tri-CBZ-arginine N-hydroxysuccinimde ester (25 g, 37.1 mmoles) were dissolved in 100 ml of dichloromethane and stirred for 2 days at room temperature. The reaction mixture was diluted with chloroform and extracted with 50 mM sodium hydroxide. The organic layer was dried over sodium sulfate and the solvent removed in vacuo to give 40.4 g of compound F. This material was used in the next step without further purification.

Compound F was dissolved in 400 ml of 50% trifluroacetic acid/dichloromethane and stirred for 2 hours. The solvents were removed in vacuo, and the residue was taken up in chloroform/100 mM sodium hydroxide. The chloroform layer was separated, dried over sodium sulfate, and stripped in vacuo. The crude compound G was used in the next step without purification.

All of compound G from step G, (approximately 36 mmoles) was dissolved in 175 ml of dichloromethane along with Boc-asparagine p-nitrophenyl ester (12.72 g, 36 mmoles). The reaction was stirred for 2 days at room temperature, then diluted up in chloroform and extracted 5 x with 50 mM sodium hydroxide, 1 x with brine, dried over sodium sulfate and stripped in vacuo. The crude oil was chromatographed on a 9 cm×30 cm silica column eluted with dichloromethane/methanol/isopropylamine (94:5:1) to give 29.3 g of compound H.

Compound H (7.29 g, 6.3 mmoles) was dissolved in 50 ml of 50% trifluroacetic acid/dichloromethane and stirred under argon for 1 hour. The solvent was removed in vacuo and the residue dissolved in chloroform and 50 mM sodium hydroxide. The layers were separated and the water layer was extracted once more with chloroform. The combined chloroform extracts-were washed with brine, dried over potassium carbonate, and stripped in vacuo. The residual solid was dissolved in a small amount of chloroform and precipitated with either. The solid was filtered off, washed with ether and dried under vacuum to give 5.61 g of compound I.

Compound I (214 mg, 0.2 mmoles) was dissolved in 2 ml of chloroform. To this solution was added 2-methoxyphenylacetic acid N-hydroxysuccinimide ester (58 mg, 0.22 mmoles), and the solution was stirred overnight at room temperature. The reaction mixture was diluted with chloroform and washed with dilute sodium hydroxide. The chloroform layer was separated, dried over sodium sulfate, and stripped in vacuo to give compound J which was used directly in the next step.

All of compound J from step J was dissolved in 5 ml of acetic acid. Palladium hydroxide on carbon (100 mg) was added, and the reaction was put under hydrogen (from a hydrogen filled balloon) and stirred overnight. The reaction was filtered through a 0.2 micron syringe filter to remove the catalyst, and the resulting solution was lyophilized. The residue was dissolved in 0.1% trifluoroacetic acid and chromatographed on a C-18 column (10 mm×250 mm Vydac C-18) eluted with acetonitrile. The fraction containing product was lyophilized to give 90 mg of Compound 5 as the TFA salt.

The synthesis of Compound 6 was carried out in a manner analogous to that for Compound 5 except that in step H, compound G was reacted with Boc-phenylalanine N-hydroxysuccinimide ester instead of Boc-asparagine p-nitrophenyl ester.

The synthesis of Compound 7 was carried out in a manner analogous to that for Compound 5 except than in step H, compound G was reacted with Boc-leucine N-hydroxysuccinimide ester instead of Boc-asparagine p-nitrophenyl ester.

The synthesis of Compound 8 was carried out in a manner analogous to that for Compound 5 except that in step F, compound E was reacted with CBZ-lysine N-hydroxysuccinimide ester instead of tri-CBZ-arginine N-hydroxysuccinimide ester.

The synthesis of Compound 10 was carried out in a manner analogous to that for Compound 5 except that in step J, compound I was coupled to 2-benzyloxyphenylacetic acid N-hydroxysuccinimide ester instead of 2-methoxyphenylacetic acid N-hydroxysuccinimide ester.

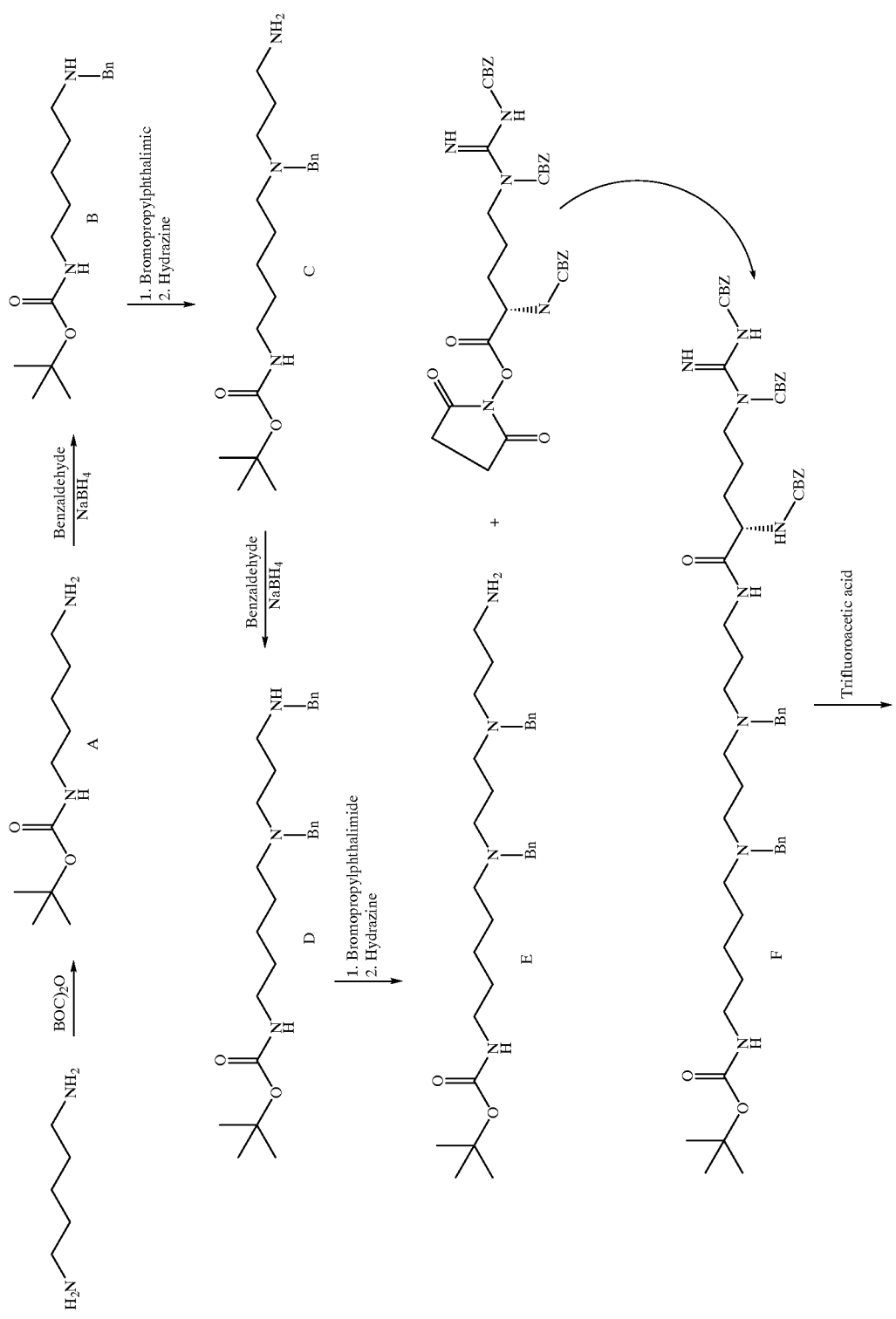

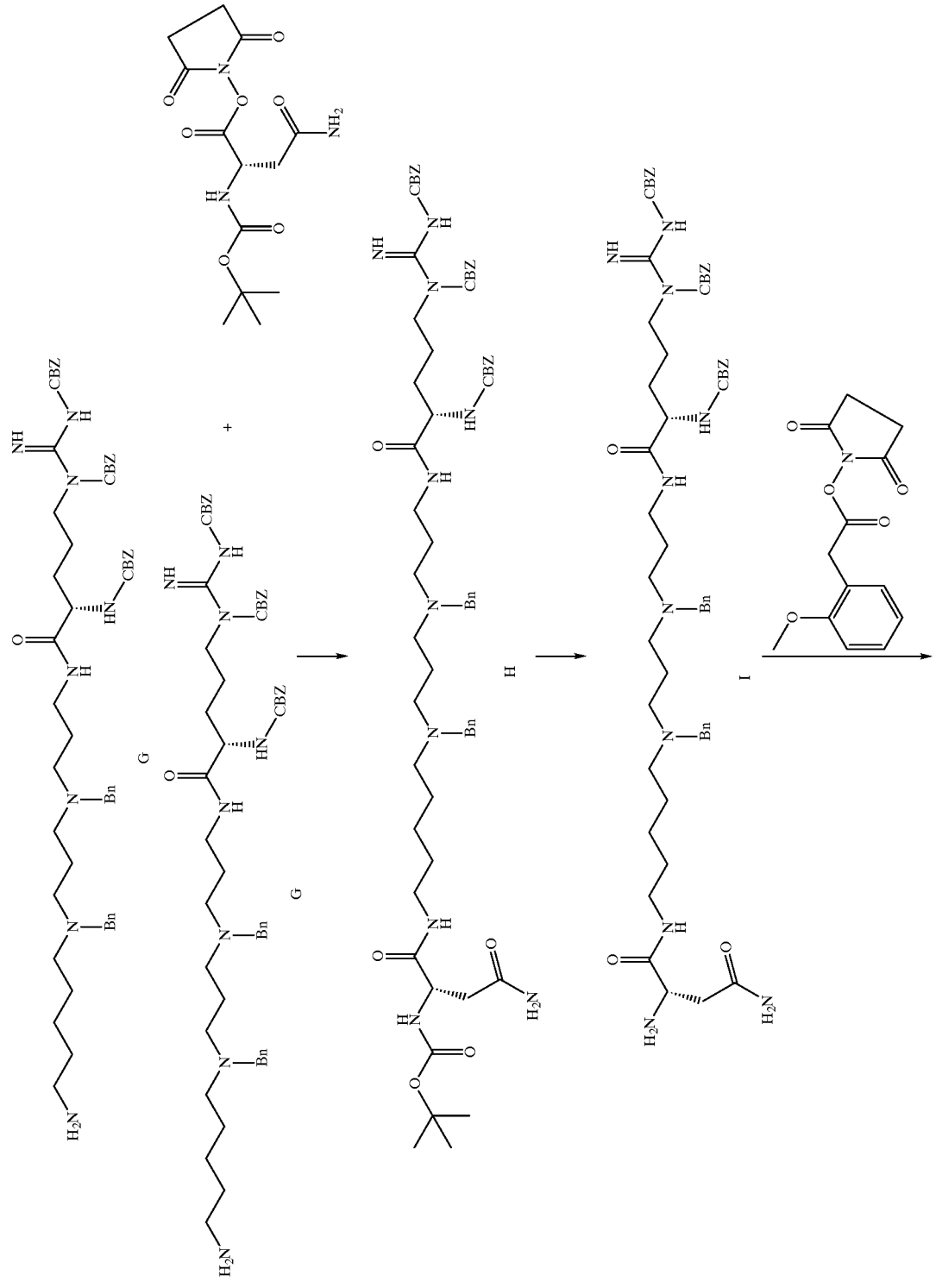

-continued
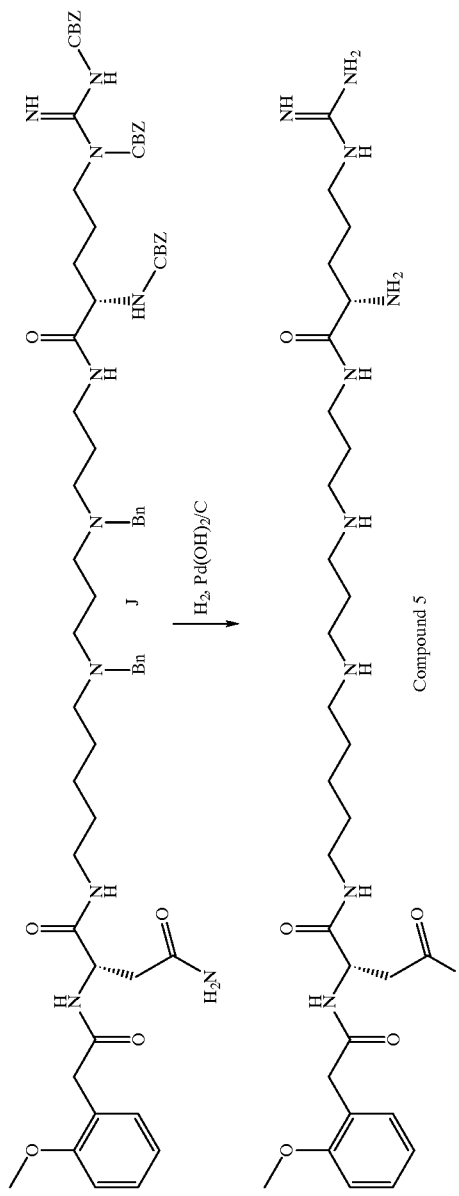

Synthesis of Compound 9 was accomplished as follows:

To a solution of 1,3-diaminopropane (100 g, 1.35 mol) in methanol (100 ml) was added acrylonitrile (79 g, 1.48 mol) dropwise over a 10 min period. The reaction was stirred 4 hr at room temperature and concentrated to an oil. This material was distilled under reduced pressure and 66 g (39%) N-cyanoethyl-1,3-diaminopropane, A, was collected at a boiling range of 95–115° C.

To a solution of A (66 g, 520 mmol) in dichloromethane (1 L) was added di-tert-butyl dicarbonate (250 g, 1.14 mol). The reaction was stirred for 16 hr at room temperature. After this time the reaction was washed with 1.0 N NaOH (1x), dried with anhydrous potassium carbonate, and concentrated to an oil. Chromatography (silica) using a gradient of hexane to ethyl acetate-hexane (1:1) afforded 73 g (43%) of the product B.

A solution of B (73 g, 222 mmol) and palladium dihydroxide (10 g, 20% Pd) in acetic acid (750 ml) was hydrogenated under 55 psi hydrogen for 4 hr at room temperature. The reaction mixture was filtered and the catalyst washed with acetic acid (3×100 ml). The filtrate and acetic acid washes were combined and concentrated to a thick oil. This material was equilibrated between dichloromethane (1 L) and 1 N NaOH (1 L). The organic layer was separated, dried over anhydrous $K_2CO_3$, and concentrated to afford 73.5 g (100%) of the product C.

A solution of C (69.6 g, 210 mmol) in methanol (300 ml) was treated dropwise over a 10 min period with acrylonitrile (11.2 g, 211 mmol) and the reaction stirred 16 hr at room temperature. After this time the reaction was concentrated to an oil. A solution of this material in dichloromethane (300 ml) was treated with di-tert-butyl dicarbonate (46.1 g, 211 mmol) and the reaction stirred 16 hr at room temperature. After this time the reaction mixture was concentrated to an oil. Chromatography (silica) using a gradient of hexane to ethyl acetate-hexane (1:1) gave 79.5 g (77%) of the product D.

A solution of D (79.5 g, 162 mmol) and palladium dihydroxide (4 g, 20% Pd) in acetic acid (800 ml) was hydrogenated at 55 psi hydrogen for 4 hr at room temperature. After this time the reaction mixture was filtered and the catalyst washed with acetic acid (3×100 ml). The filtrate and the acetic acid washes were combined and concentrated to a thick oil. This material was equilibrated between dichloromethane (1 L) and 1 N NaOH (1 L). The organic layer was separated, dried over anhydrous potassium carbonate, and concentrated to afford 79 g (100%) of the product E.

A solution of E (1.4 g, 2.87 mmol), 5-fluoro-indole-3-acetic acid (507 mg, 2.62 mmol), and 1-trihydroxybenztriazole (858 mg, 6.35 mol) were mixed in DMF (5 ml) and treated with DCC (594 mg, 2.88 mmol) in chloroform (5 ml). The reaction mixture was stirred 4 hr at room temperature after which it was filtered and concentrated. Chromatography (silica) using a gradient of dichloromethane to methanol-dichloromethane (1:9) afforded 1.1 g (58%) of the product F.

A solution of the amide F (1.1 g, 1.66 mmol) in acetonitrile (36 ml) was treated dropwise over a 1 min period with concentrated HCl (4 ml). The reaction was stirred 4 hr at room temperature. The acetonitrile was evaporated, in vacuo, and the crude product dissolved in water to a total volume of 10 ml. This material was chromatographed through Vyadac RP ($C_{18}$, 20×2.5 cm i.d.) in ten aliquots (1 ml) using a gradient (0.6%/min) of 0.1% HCl to acetonitrile at 10 ml/min measuring optical density at 280 nm to afford 483 mg. (80%) of Compound 9. FABMS observed ($M^+$ H) m/z=364.

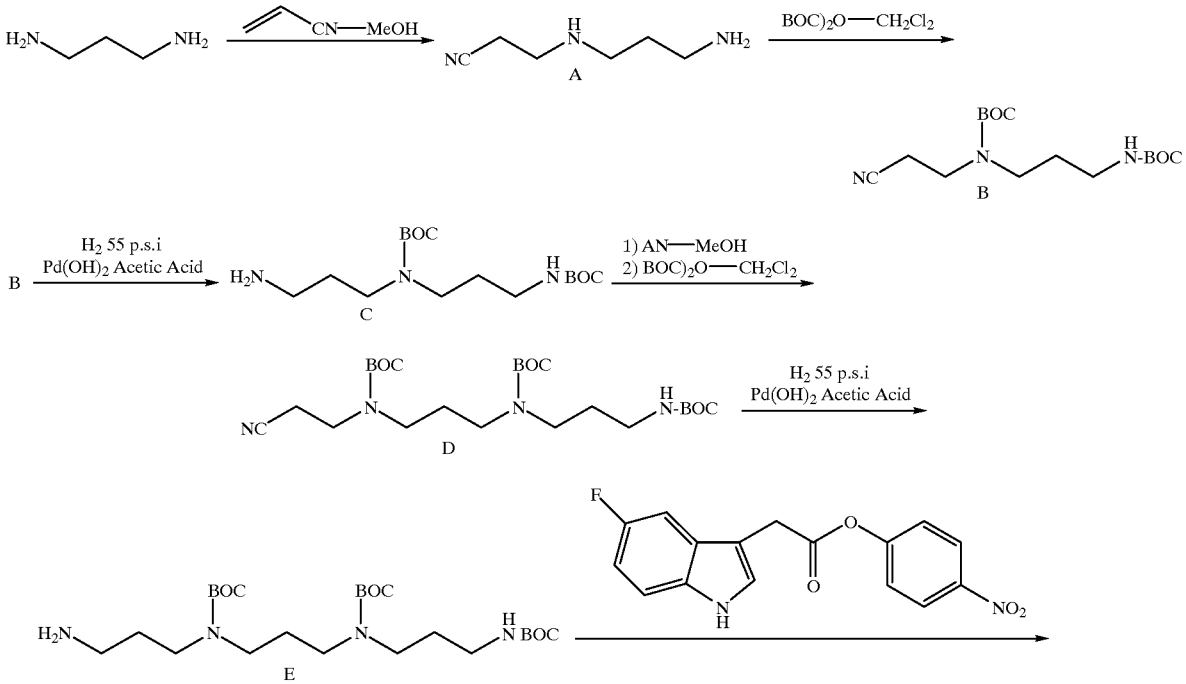

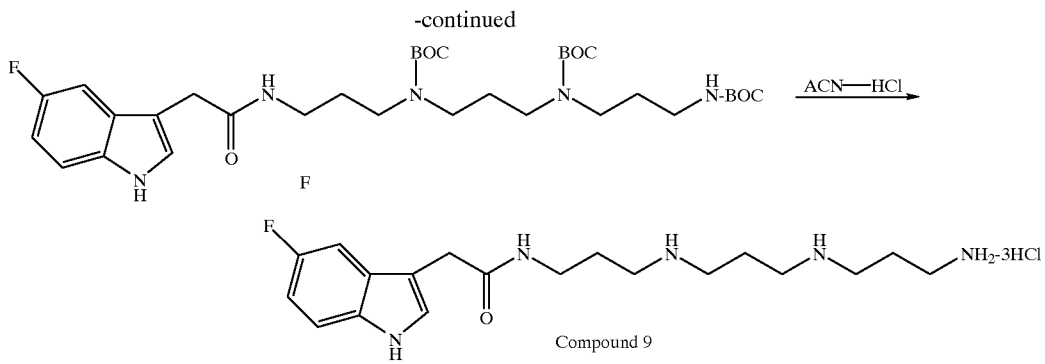

Compound 9

Synthesis of Compound 11 was accomplished as follows:

A solution of ethylamine hydrochloride (100 g, 1.23 mol) in methanol (500 ml) was cooled to 0° C. and treated with triethylamine (130 g, 1.29 mol) followed by acrylonitrile (65.2 g, 1.23 mol). The reaction was then warmed to room temperature and stirred for 16 hr. To this was added di-tert-butyl dicarbonate (268 g, 1.23 mol) in dichloromethane (300 ml). The reaction was stirred 4 hr at room temperature, concentrated and dissolved in diethyl ether. This was washed with 10% HCl (3x), 0.1 N NaOH (3x) and brine (1x). The ether fraction was dried over $K_2CO_3$ and concentrated to afford 220 g (91%) of the product A, as an oil. GC/MS ($R_t$=3.964 min) m/z (relative intensity) 198 ($M^+$, 2), 143 (7), 125 (27), 97 (31), 57 (100).

A solution of A (50 g, 253 mmol) and palladium dihydroxide (5 g) in acetic acid (300 ml) was hydrogenated at 70 psi hydrogen for 16 hr at room temperature. The reaction was filtered and the catalyst washed with acetic acid (3x). The filtrate and acetic acid washes were combined and concentrated to a thick oil. This material was dissolved in dichloromethane (500 ml) and treated with 1 N NaOH until the pH of the equilibrated phases was basic (pH 14). The organic layer was removed, dried over $K_2CO_3$ and concentrated to afford, 39.06 g (76%) of the product B, as an oil.

A solution of B (39.06 g, 193.4 mmol) in methanol (50 ml) was treated with benzaldehyde (20.5 g, 193.4 mmol) and anhydrous $MgSO_4$. The reaction was stirred 8 hr at room temperature and poured directly into a solution of sodium borohydride (7.3 g, 193 mmol) in ethanol (300 ml). The reaction was stirred 4 hr at room temperature, quenched with dilute HCl and concentrated in vacuo. The acidic solution was basified with 1 N NaOH and the product extracted into ether. The ether layer was dried and concentrated to afford 19.5 g (35%) of the product C as an oil.

A solution of C (19.5 g, 66.8 mmol) in acetonitile (100 ml) was treated with N-(3-bromopropyl)phthalimide (19.7 g, 73 mmol), KF-Celite (8.5 g, 50% KF) and set to reflux for 16 hr. The reaction was then filtered and concentrated to afford intermediate D. A solution of this material in methanol (500 ml) was treated with hydrazine (15 ml) and refluxed for 4 hr. After this time the reaction was concentrated to a white solid and dissolved in ether-1 N NaOH. The aqueous layer was removed and the remaining ether washed with 1 N NaOH (3x), brine, and concentrated to an oil. Chromatography (silica) using a gradient of chloroform to chloroform-methanol (9:1) afforded 6.47 g (28%) of the product E as a clear oil.

A solution of E (6.47 g, 18.5 mmol) in methanol (50 ml) was treated with benzaldehyde (2.06 g, 19.5 mmol) and anhydrous $MgSO_4$ and stirred 8 hr at room temperature.

After this the reaction was poured directly into a solution of sodium borohydride (1 g, 26 mmol) in ethanol (300 ml) and stirred for 4 hr at room temperature. The reaction was quenched with dilute HCl and concentrated. This material was suspended in ether and treated with 1 N NaOH until pH 14. The ether layer was separated, dried over $K_2CO_3$ and concentrated to afford the intermediate F (6.23 g) as an oil.

A solution of this material in acetonitrile (50 ml) was treated with N-(3-bromopropyl)phthalimide (5.4 g, 20 mmol), KF-Celite (2.3 g) and set to reflux for 16 hr. The reaction was filtered and concentrated. This material, containing intermediate G, in methanol (300 ml) was treated with hydrazine (10 ml) and refluxed for 4 hr. After this time the reaction was concentrated to a white solid and dissolved in ether-1 N NaOH. The aqueous layer was removed and the remaining ether washed with 1 N NaOH (3x), brine, and concentrated to an oil. Chromatography (silica) through silica using a gradient of chloroform to chloroform-methanol (9:1) afforded 4.5 g (49%) of the product H as a clear oil.

A solution of 5-fluoro-3-indole acetic acid (2 g, 10.4 mmol) and p-nitrophenol (1.6 g, 11.6 mmol) in chloroform-DMF (100:1, 200 ml) was treated with DCC (2.18 g, 10.6 mmol) and the reaction stirred at 16 hr at room temperature. The reaction mixture containing the active ester I was filtered directly into a stirred solution of H (4.5 g g, 9 mmol). This reaction was stirred 4 hr at room temperature and poured into 300 ml ether. The ether layer was washed with 1 N NaOH (6x), brine, dried, and concentrated to an oily solid. This material was chromatographed through a small silica plug using chloroform-methanol to afford the intermediate J. A solution of this material, and a catalytic amount of palladium dihydroxide in acetic acid (200 ml) was hydrogenated under 60 psi hydrogen for 2 hr at room temperature. The reaction was filtered and the catalyst washed with acetic acid (3x). The filtrate and washes were combined and concentrated to afford K as a thick oil. A solution of this material in acetonitrile (20 ml) was treated with concentrated HCl (2 ml) and the reaction stirred under nitrogen for 2 hr at room temperature. The reaction was filtered and the precipitate (crude Compound 11) dissolved in 5 ml $H_2O$. The concentration of product was determined as 233 mM by UV. Analytic RP HPLC showed the product to be 91% pure. Chromatography of a portion of this material (in 100 µl aliquots) through Vydac RP ($C_{18}$, 25×2 cm) using a gradient (1%/min) of 0.1% HCl to acetonitrile, at 10 ml/min monitoring optical density at 280 nm, gave pure Compound 11. $UV_{max}$ (0.1% TFA) 284 nm (e 6140).

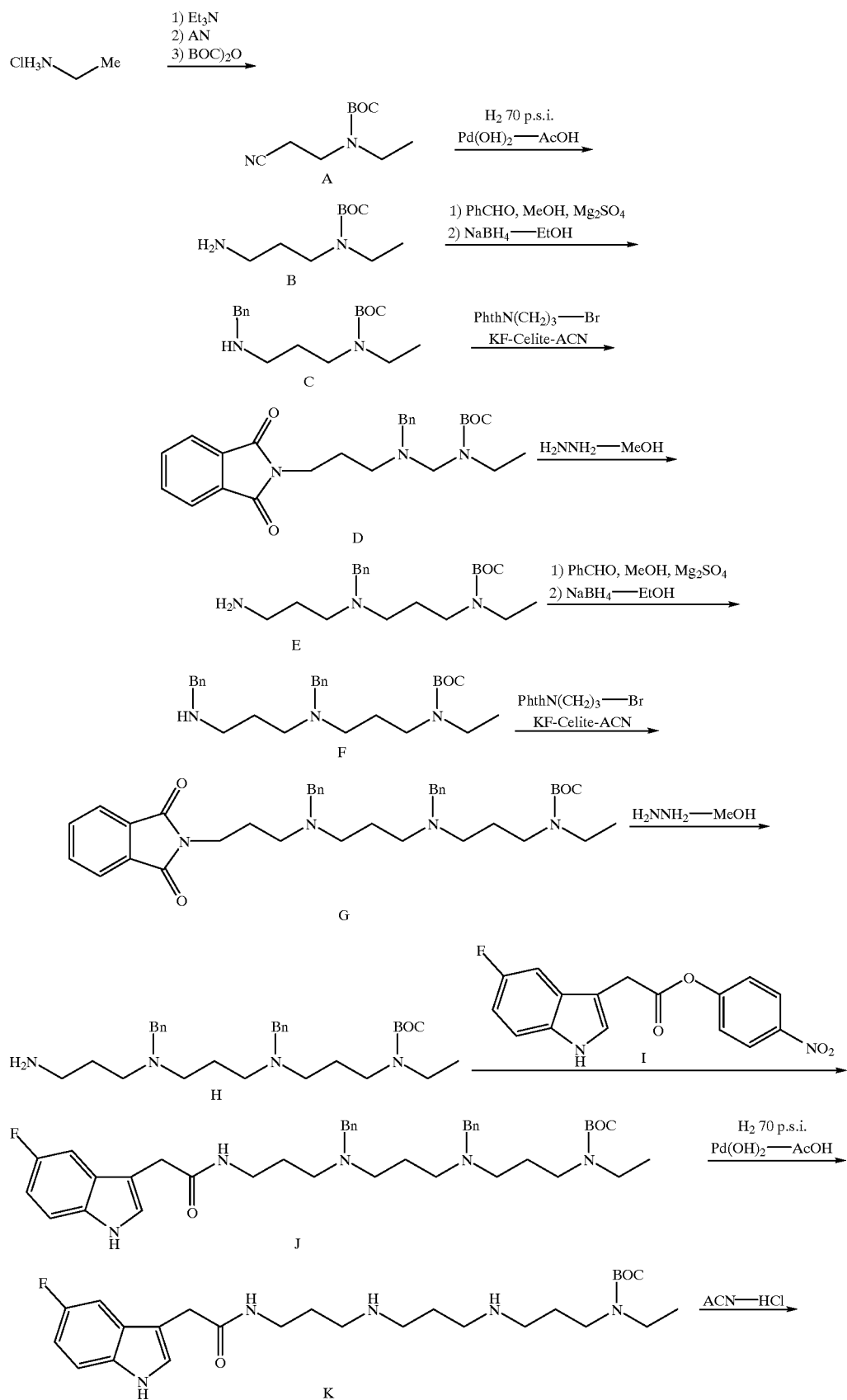

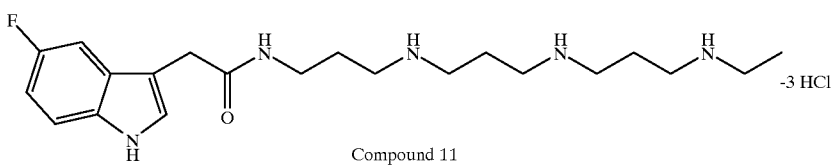

Compound 11

Synthesis of Compound 12 was accomplished as follows:

A solution of 4,9-dioxa-1,12-dodecanediamine (50 g, 245 mmol) in dioxane (500 ml) was treated dropwise over 60 min with a solution of di-tert-butyl dicarbonate (5.88 g, 27 mmol) in dioxane (300 ml). The reaction was stirred 24 hr at room temperature and reduced to a white solid. This material was partitioned between water-hexane. GC/MS of the organic and aqueous fractions showed di-addition product in the hexane fraction with the product A and starting diamine in the aqueous fraction. The aqueous layer was separated and washed with ether. GC/MS analysis showed the product A in the ether layer and starting diamine in the aqueous layer. The ether layer was separated, dried over sodium sulfate and concentrated to afford 10.2 g (14%) of the product A, as a clear oil. GC/EI-MS ($R_t$=8.86 min), m/z (relative intensity) 205 ($M^+1$, 5), 148 (59), 130 (16), 114 (17), 100 (16), 74 (61), 58 (100).

A solution of 5-fluoro-indole-3-acetic acid (2 g, 10.4 mmol) and p-nitrophenol (1.73 g, 12.4 mmol) in chloroform-DMF (75:1, 125 ml) was treated with DCC (2.25 g, 10.9 mmol) and the reaction stirred 24 hr at room temperature. This was then filtered (removing DCU) directly into a stirred solution of A (5.2 g, 17.1 mmol) in chloroform (100 ml). After this addition triethylamine was added (2 g, 20 mmol) and the reaction stirred 4 hr at room temperature. The solution was added to ether (600 ml) and washed with 1N NaOH (6×100 ml), 10% HCl (1×100 ml) and brine. The organic layer was dried (sodium sulfate) and concentrated to a clear oil. Chromatography (silica) using chloroform-methanol (50:1) afforded 4.93 g (99% from the indole) of the product B, as a clear oil.

A solution of compound B (4.93 g, 10.3 mmol) in acetonitrile (50 ml) was treated with concentrated HCl (5 ml) and the solution stirred 4 hr at room temperature. Evaporation of the solvent in vacuo, and lyophilization from water afforded (5.26 g, 99%) of Compound 12, as a thick oil. $^1$H-NMR (CDCl$_3$, free base) d 9.92 (1H, br s), 7.30 (1H, dd, J=9 Hz, J=4 Hz), 7.20 (1H, dd, J=9 Hz, J=2 Hz), 7.19 (1H, s), 6.94 (1H, dt, J=9 Hz, J=2), 6.30 (1H br t), 3.67 (2H, s), 3.56 (2H, t, J=6 Hz), 3.40 (2H, t, J=6 Hz), 3.32 (4H, br t, J=6 Hz), 3.10 (2H, t, J=7 Hz), 2.88 (2H, t, J=7 Hz), 1.79 (2H, p, J=6 Hz), 1.72 (2H, br m), 1.64 (2H, p, J=6 Hz), 1.44 (2H, m), 1.36 (2H, m); $^{13}$C-NMR (CDCl$_3$, free base) d 171.2, 125.7, 112.1, 112.0, 110.8, 110.4, 104.4, 103.8, 103.5, 71.0, 70.9, 70.0, 69.4, 39.9, 38.5, 33.4, 32.9, 28.8, 26.5, 26.4.

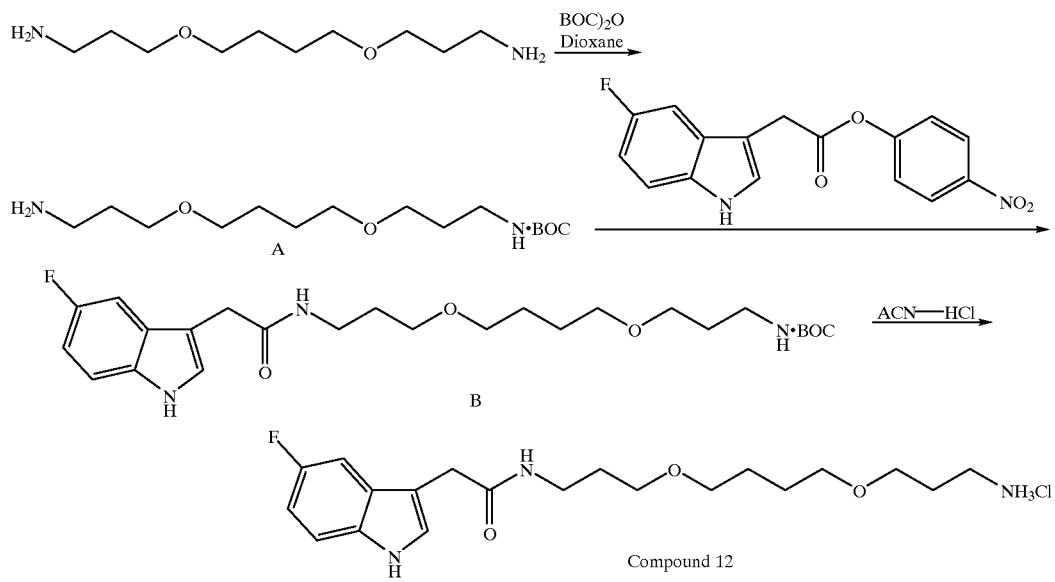

Compound 12

Compounds 13–18 were synthesized by standard procedures as described above.

Example 29

Synthesis of Simplified Arylalkylamines

Synthesis of Compound 20 was accomplished as follows.

A solution of sodium hydride (1.21 g, 50 mmol) in dimethoxyethane was treated with diethyl cyanomethylphosphonate (8.86 g, 50 mmol) and the reaction stirred 4 hr at room temperature. To this was added 3,3'-difluorobenzophenone (10 g, 46 mmol) in DME. The reaction was stirred 24 hr at room temperature, quenched with H$_2$O, and partitioned between diethyl ether and water. The ether fraction was dried over Na$_2$SO$_4$ and concentrated. GC/MS of this material showed 90% of the product A and 10% starting benzophenone.

A solution of this material in ethanol with a catalytic amount of Pd(OH)$_2$ was hydrogenated at 55 psi hydrogen for 4 hr at room temperature. The reaction was filtered and the catalyst washed with ethanol (3x). The filtrate and ethanol washes were combined and concentrated. GC/MS of this material showed 90% of the product B and 10% of the starting benzophenone.

A solution of this material in THF was treated with 70 ml 1 M B$_2$H$_6$ (70 mmol) in THF and refluxed 1 hr. After cooling the reaction was treated with 6 N HCl (50 ml) and refluxed an additional hour. After cooling the reaction was basified to pH 14 with 10 N NaOH and equilibrated with ether. The ether layer was removed and washed with 10% HCl (3x). The acidic washes were combined, basified to pH 14 with 10 N NaOH and extracted with dichloromethane (3x). The organic washes were combined, dried over Na$_2$SO$_4$, and concentrated to yield an oil. GC/MS of this material showed 100% Compound 20. GC/EI-MS (R$_t$=7.11 min) m/z (relative intensity) 247 (M$^+$, 31), 230 (100), 215 (30), 201 (52), 183 (63), 134 (23), 121 (16), 101 (21), 95 (15), 77 (15). This material in diethyl ether was filtered and treated with 35 ml 1 M HCl in ether. The precipitate was collected, dried, and recrystallized from water-ethanol to afford 1.045 g of Compound 20, as the hydrochloride salt. $^1$H-NMR (CDCl$_3$) δ8.28 (3H, br s), 7.28–7.17 (2 H, m), 7.02–6.86 (6 H, m), 4.11 (1H, t, J=8 Hz), 2.89 (2H, br t, J=8 Hz), 2.48 (2H, br t, J=7 Hz); $^{13}$C-NMR (CDCl$_3$) δ164.6, 161.3, 144.8, 144.7, 130.4, 130.3, 123.3, 123.2, 114.7, 114.5, 114.1, 113.8, 47.4, 38.4, 32.7.

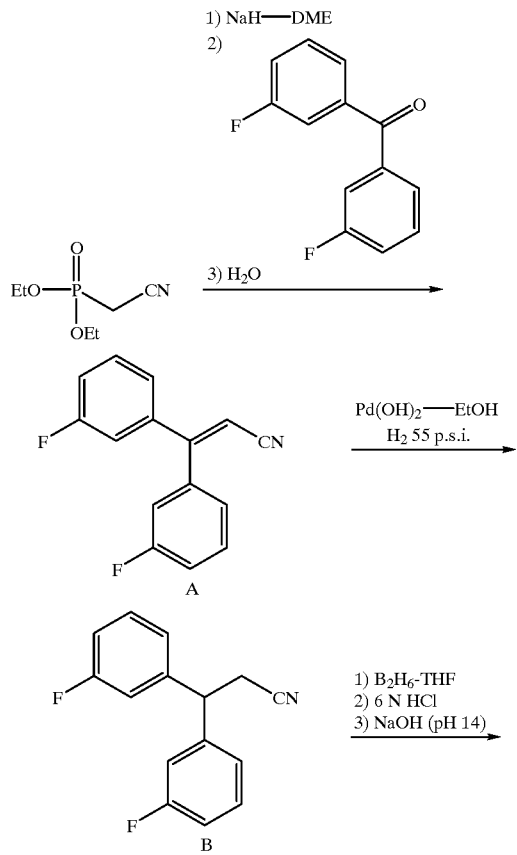

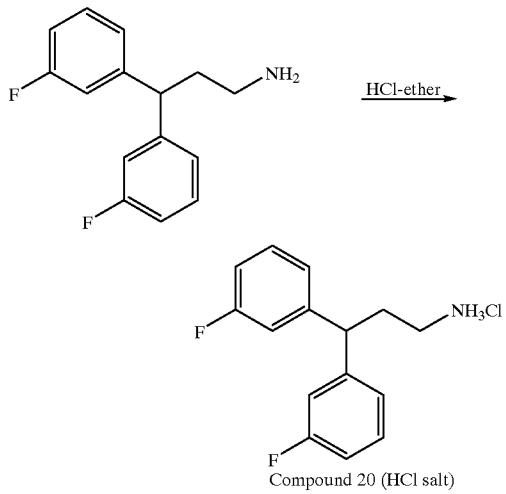

Compound 20 (HCl salt)

Alternatively, the synthesis of Compound 20 was accomplished as follows.

To a solution of butyl lithium (22.9 ml, 57.3 mmol, 2.5 M in hexane) in dry THF (100 ml) at −78° C. was added a solution of acetonitrile (2.35 g, 57.3 mmol) in THF (30 ml) dropwise over a period of 5 min. The mixture was stirred at −78° C. for 30 min. A solution of 3,3-difluorobenzophenone (10.0 g, 45.8 mmol) in THF (50 ml) was added dropwise over a period of 20 min. The reaction was then stirred at −78° C for 1 h. A saturated NH$_4$Cl solution (100 ml) was added, the layers were separated, and the aqueous layer was extracted with ether (2×50 ml). The combined organic layers were washed with brine (2×20 ml) and H$_2$O (20 ml), dried (Na$_2$SO$_4$), and evaporated under vacuum. The residue was further dried by azeotroping the residual water with absolute EtOH (2×25 ml) followed by vacuum drying (0.1 mm Hg, 18 h). The crude product was dissolved in hot CHCl$_3$ (50 ml). Hexane (100 ml) was added and the solution was slowly evaporated under vacuum. The material crystallized during the evaporation after approximately 75 ml of solvent was removed. The product was collected and washed with ice cold hexane (2×20 ml) and dried to provide 10.7 g, 90.2% yield of colorless crystals, product A.

The γ-aminonitrile was dissolved in absolute EtOH (250 ml). NaOH (11.6 ml, 10 N) and nickel-aluminum catalyst (5 g, 50% slurry, Fluka Chemika) were added and the mixture was hydrogenated at 25° C., 50 psi for 3 hr. The catalyst was removed by filtration and the solvent was reduced under vacuum to a volume of approximately 20 ml at which time the product crystallized. Ice cold H$_2$O (4×50 ml) was used to transfer the crystalline mass to a filter. This material was dried (over blotter paper) to provide 8.9 g, 87.7% yield of a white crystalline solid, product B.

The tetiary alcohol (3.7 g, 14.1 mmol) was dissolved in hot absolute EtOH (2 ml). Hot concentrated HCl (75 ml) was added and the resulting solution was refluxed gently for 5 min. The alkene crystallized from the reaction mixture during heating. The resulting mixture was then cooled in an ice bath for 15 min. Ice cold H$_2$O (75 ml) was added and the product was collected on a funnel, washed with ice cold H$_2$O (3×20 ml), and dried to yield 3.6 g, 90.1% yield of the colorless crystalline hydrochoride salt, product C.

The substituted diphenylpropenamine hydrochloride (22.0 g, 78.2 mmol) was dissolved in absolute EtOH (250 ml). 10% Pd/C (2 g) was added and the reaction mixture was hydrogenated on a Parr apparatus at 25° C. and 50 psi for 1 hr the catalyst was removed by filtration through Celite® and washed with EtOH (3×20 ml). The solvent was then removed under vacuum to provide a white solid. This material was then recrystallized twice from acetonitrile (145 ml) to give 16.3 g, 74% yield of tiny colorless needles, Compound 20 as the hydrochloride salt; mp 207.5–208.0° C.

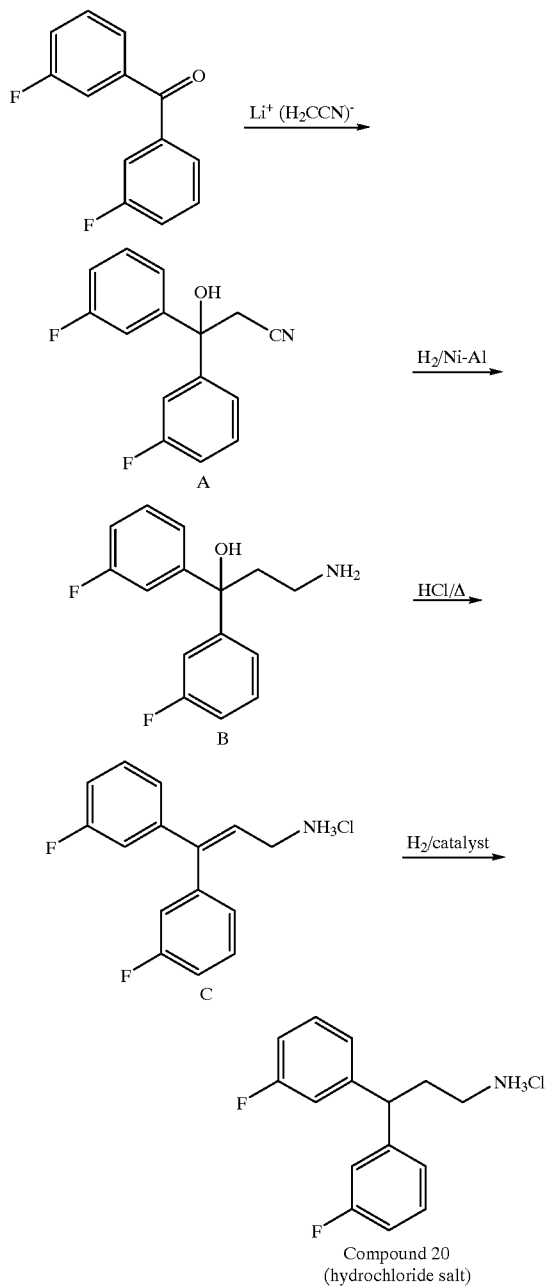

Synthesis of Compound 21, Compound 33 and Compound 34 was accomplished as follows.

A 100 ml round-bottomed flask equipped with stir bar, septa, and argon source was charged with compound 1 (2.43 g, 10 mmol) in 30 ml THF. The solution was cooled to −78° C. and treated dropwise with 11 ml lithium bis (trimethylsilyl)amide (1M in THF) (11 mmol). The reaction was stirred at −78° C. for 30 min and treated dropwise with excess iodomethane (3.1 ml, 50 mmol). The reaction was stirred 30 min at −58° C. GC/EI-MS analysis of an aliquot from the reaction showed consumption of the starting nitrile 1. The reaction was quenched with water, diluted with diethyl ether and transferred to a separatory funnel. The ether layer was washed with 10% HCl (3X), brine (1X), dried with anhydrous $MgSO_4$, and concentrated to a brown oil. This material was distilled (Kugelrohr, 100° C.) at reduced pressure to afford 1.5 g of a clear oil. GC/EI-MS of this material showed it to contain the desired product 2, ($R_t$=7.35 min) m/z (rel. int.) 257 ($M^+$, 3), 203 (100), 183 (59), 170 (5), 133 (4), 109 (3); $^1$H-NMR ($CDCl_3$) δ7.4–6.9 (8H, m), 4.01 (1H, d, J=10 Hz), 3.38 (1H, dq, J=7, 10 Hz), 1.32 (3H, d, J=7 Hz); $^{13}$C-NMR ($CDCl_3$) δ19.4, 30.5, 54.2, 114.5, 114.6, 114.7, 114.9, 115.0, 115.3, 123.3, 123.4, 123.6, 123.7, 130.5, 130.6, 131.7.

Product 3 was synthesized by the catalytic reduction of 2 using Raney nickel in 95:5 EtOH:aqueous sodium hydroxide (2 Eq.) under 60 psi hydrogen. GC/EI-MS ($R_t$=7.25 min) m/z (rel. int.) 261 ($M^+$, 20), 244 (35), 229 (16), 215 (17), 201 (80), 183 (100), 133 (42), 115 (27), 109 (47), 95 (20); $^1$H-NMR ($CDCl_3$) δ7.3–6.8 (8H, m), 3.62 (1H, d, J=10 Hz), 2.70 (1H, M), 2.40 (2H, m), 1.73 (2H, m), 0.91 (3H, d, J=7 Hz). Note that product 3 in this reaction sequence corresponds to Compound 21.

Product 2 in 10% IPA-hexane (100 mg/ml) was chromatographed, in 500 μl aliquots, through Chiral Cel OD (2.0×25 cm) using 10% IPA-hexane at 10 ml/min measuring optical density at 254 nm. This afforded the two optically pure enantiomers 4 and 5 (as determined by analytical chiral HPLC; Note, the stereochemistry of these two compounds has not been assigned at this time). These two compounds were identical in their GC/EI-MS and $^1$H-NMR spectra as product 2 (data above).

Each of the enantiomers 4 and 5 was reduced separately using dimethyl sulfideborane complex in the following manner. A solution of compound (4 or 5) in THF was heated to reflux and treated with excess (2 Eq.) 1M (in THF) dimethyl sulfideborane complex and the reaction refluxed 30 min. After this time the reaction was cooled to 0° C. and treated with 6 N HCl. The reaction was set to reflux for 30 min. After this time the reaction was transferred to a separatory funnel, basified to pH>12 with 10N NaOH, and the product (6 or 7) extracted into ether. The ether layer was washed with brine, dried over anhydrous $MgSO_4$ and concentrated to an oil. The product was purified by prep-TLC using 5% methanol-chlorform. Each of the individual enantiomers (6 and 7) were found to be identical in their GC/EI-MS and $^1$H-NMR spectra as product 3 (data above). Note that products 6 and 7 in this scheme correspond to Compounds 33 and 34.

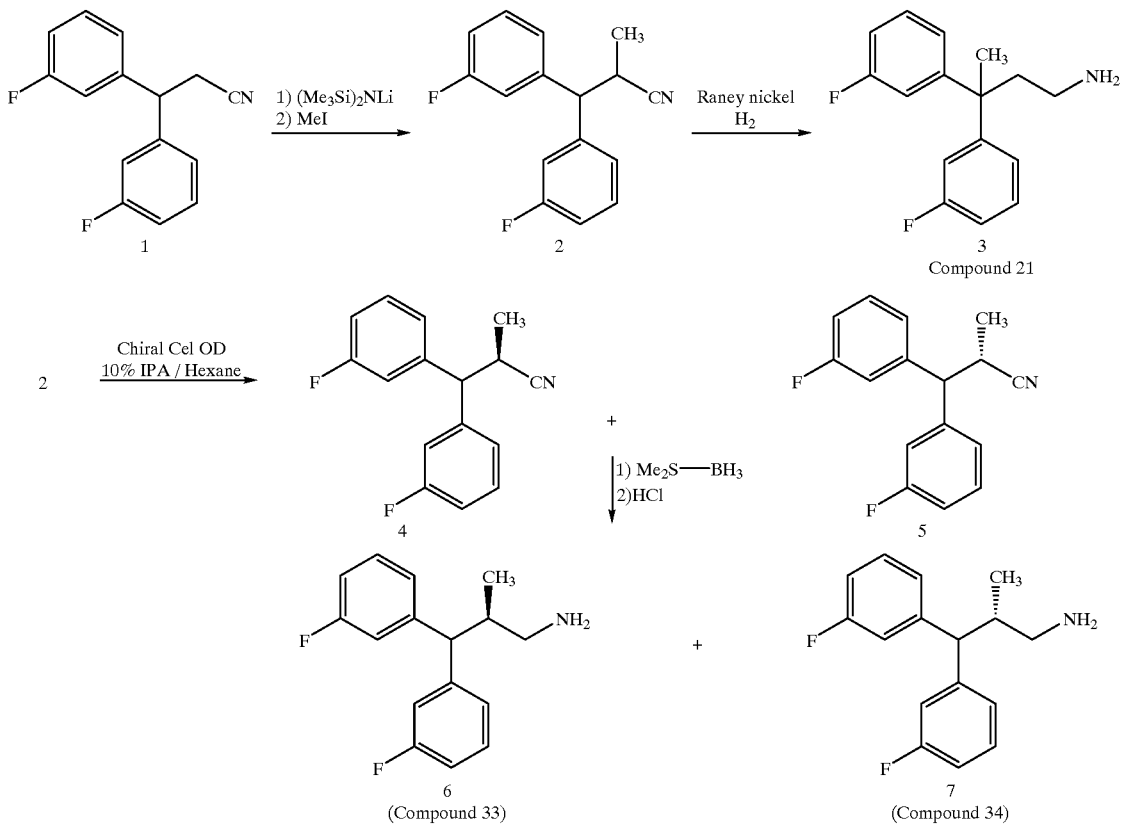

Synthesis of Compound 22 was accomplished as described below. Compound 23 was synthesized in a similar manner.

Triethyl phosphonoacetate (17.2 g, 76.8 mmol) was slowly added to a suspension of sodium hydride (3.07 g, 76.8 mmol) in N,N-dimethylformamide (350 ml). After 15 minutes 3,3'-difluorobenzophenone (15.2 g, 69.8 mmol) was added to the solution and stirred an additional 18 hr. The reaction mixture was quenched with water and partitioned between water and ether. The combined organic layers were washed with brine and dried over anhydrous magnesium sulfate. The solvent was evaporated in vacuo to give 19.7 g of ethyl 3,3-bis(3-fluorophenyl)acrylate as a yellow oil.

To a solution of ethyl 3,3-bis(3-fluorophenyl)-acrylate (19.7 g, 68.4 mmol) in 200 ml of ethanol was added palladium hydroxide on carbon (3.5 g). The mixture was shaken under 60 psi of hydrogen for 3 hours, then filtered and evaporated in vacuo to give 19.5 g of product A as a colorless oil.

The ethyl ester A (19.2 g) was hydrolyzed by stirring for 6 days with 50 ml of 10 N sodium hydroxide. The reaction mixture was then diluted with 50 ml of water and acidified to pH 0 with concentrated HCl. The aqueous mixture was extracted 3 times with ether and the ether extracts dried over magnesium sulfate and evaporated to give 3,3-bis(3-fluorophenyl)propionic acid as a white powder.

3,3-bis(3-fluorophenyl)propionic acid (13 g, 49.6 mmol) was dissolved in 50 ml (685 mmol) of thionyl chloride and stirred overnight at room temperature. The excess thionyl chloride was removed in vacuo on a rotary evaporator to give 13.7 g of product B as a yellow oil.

To acid chloride B (13.7 g, 49 mmol) dissolved in 100 ml of dry THF was added iron(III) acetylacetonate (0.52 g, 1.47 mmol). Methylmagnesium chloride (16.3 ml, 49 mmol) was then added over a period of 1 hr by syringe pump. The reaction was stirred for an additional hour, then quenched by pouring into ether/5% HCl. The ether layer was separated, washed with 5% HCl and saturated NaCl, and dried over sodium sulfate. The solvent was evaporated in vacuo to give 4,4-bis($^3$-fluorophenyl)-2-butanone as a yellow oil. The crude oil was purified on silica gel using heptane/ethyl acetate as the elutant.

To 4,4-bis(3-fluorophenyl)-2-butanone (5.7 g, 21.9 mmol) in 25 ml of ethanol was added pyridine (1.91 g, 24.1 mmol) and methoxylamine hydrochloride (2.01 g, 24.1 mmol). The reaction was stirred overnight at room temperature, then poured into ether/5% HCl. The ether layer was separated, washed with 5% HCl and saturated NaCl, and dried over sodium sulfate. The solvent was evaporated in vacuo to give 6.26 g of the O-methyl oxime of 4,4-bis(3-fluorophenyl)-2-butanone. To sodium borohydride (4.1 g, 108.3 mmol) in 15 ml of THF was slowly added zirconium tetrachloride (6.31 g, 27.1 mmol). This mixture was stirred for 15 min, then the oxime (6.26 g, 21.7 mmol) in 6 ml of THF was added over 5 min. After 3 hours of stirring at room temperature, the reaction was worked up by slowly adding 50 mM sodium hydroxide followed by ether. The aqueous layer was extracted 4 times with ether, and the combined ether extracts were dried over sodium sulfate. The solvent was evaporated in vacuo to give 5.3 g of Compound 22.

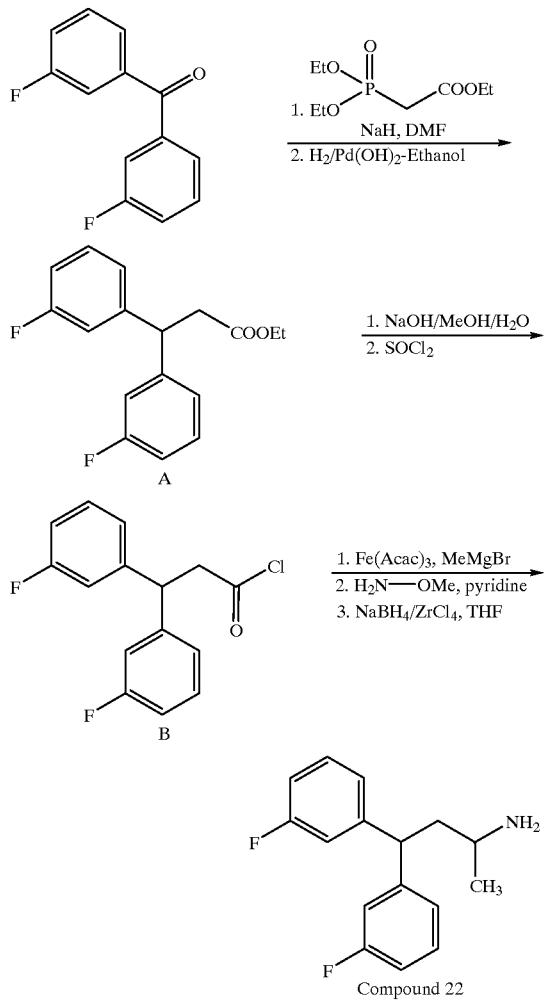

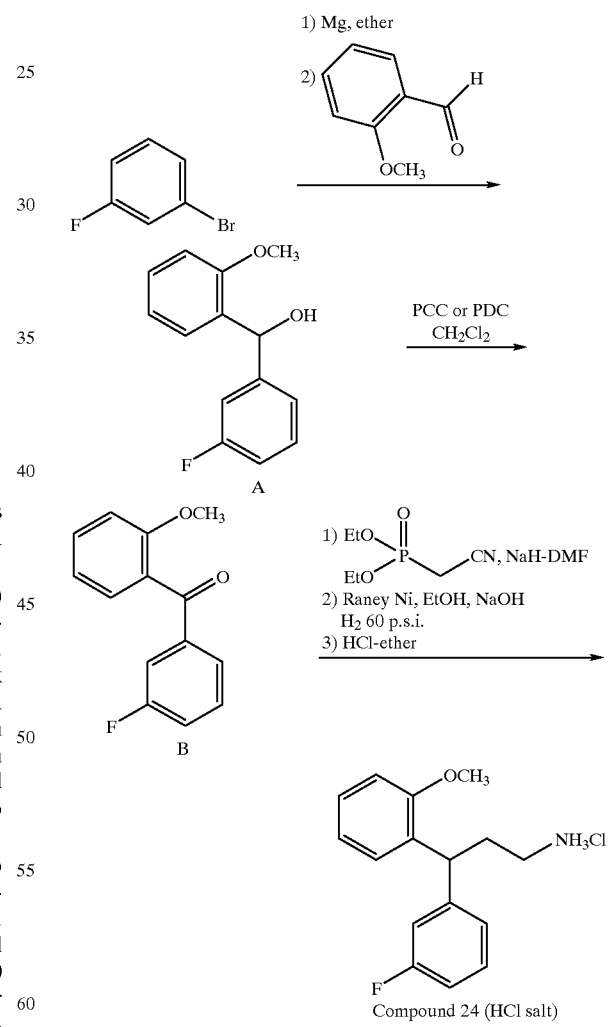

Compound 24 (HCl salt)

an additional 2 hr. The reaction mixture was quenched with water, and partitioned between water and ether. The combined organic layers were washed with brine and dried over anhydrous magnesium sulfate. The solvent was evaporated in vacuo to give a pale yellow oil.

In a glass bomb, the oil was dissolved in 100 ml ethanol and 20 ml 10N NaOH. A catalytic amount of Raney Nickel suspened in water (ca. 15 mol percent) was added to the solution. The reaction mixture was shaken under 60 psi $H_2$ for 12 hr on a Parr Hydrogenator. After filtering off excess Raney Nickel, the solution was extracted with chloroform. The combined organic layers were washed with brine and dried over anhydrous magnesium sulfate. After filtration, the oil was run through a silica gel column in chloroform and methanol. The solvent was evaporated in vacuo to give a pale yellow oil. GC/EI-MS ($R_t$=8.10 min) m/z (rel. intensity) 259 (100), 242 (44), 213 (48), 183 (42), 136 (50), 109 (94), 91 (60), 77 (25). The oil was then acidified with hydrogen chloride in diethyl ether. Evaporation of the ether afforded a pale yellow solid that was recrystallized in hot acetonitrile to afford 3.45 g (42.1% yield) white needles of Compound 24, as the hydrochloride salt.

Synthesis of Compound 24 was accomplished as described below. Compounds 25–29 were prepared in a similar manner.

A suspension of magnesium turnings (0.95 g, 39.2 mmol) in 150 ml anhydrous diethyl ether was treated with 1-bromo-3-fluorobenzene (6.83 g, 39.2 mmol) dropwise via syringe. After 1.5 hr the solution was transfered via cannula to a flask containing o-anisaldehyde (5.0 g, 36.7 mmol) in 100 ml anhydrous diethyl ether at 0° C. and stirred 2 hr. The reaction mixture was quenched with water and partitioned between water and ether. The combined organic layers were washed with brine and dried over anhydrous magnesium sulfate to afford 7.90 g (93% yield) of product A.

Pyridinium dichromate (16.0 g, 42.5 mmol) was added to a solution of the alcohol A (7.90 g, 34.0 mmol) in dichloromethane (100 ml), and the reaction was stirred 12 hr. Diethyl ether (300 ml) was added to the reaction mixture and the black solution was filtered through a silica gel plug (30 cm) and washed with an additional 500 ml ether. After evaporation of the solvent in vacuo, the solid was recrystallized from acetone to give 7.45 g (95% yield) of product B.

Diethyl cyanomethylphosphonate (7.0 g, 39.5 mmol) was slowly added to a suspension of sodium hydride (1.58 g, 39.5 mmol) in 100 ml N,N-dimethylformamide. After 30 minutes the ketone B was added to the solution and stirred Synthesis of Compound 30 was accomplished as described below. Compound 31 was prepared in a similar manner.

A suspension containing magnesium turnings (0.95 g, 39.1 mmol) in 150 ml anhydrous diethyl ether was treated with 1-bromo-3-fluorobenzene (6.85 g, 39.1 mmol) dropwise via syringe. After 1.5 hr the solution was transfered via cannula to a flask containing 3-chlorobenzaldehyde (5.0 g, 35.6 mmol) in 100 ml anhydrous diethyl ether at 0° C. and stirred 2 hr. The reaction mixture was quenched with water and partitioned between water and ether. The combined organic layers were washed with brine and dried over anyhydrous magnesium sulfate to afford 8.40 g (>99% yield) of product A.

Pyridinium chlorochromate (15.0 g, 39.8 mmol) was added to a solution of the alcohol A (8.40 g, 35.5 mmol) in 100 ml dichloromethane and stirred 18 hr. Diethyl ether (300 ml) was added to the reaction mixture and the black solution was filtered through a silica gel plug (30 cm), and washed with an additional 500 ml ether. After evaporation of the solvent the solid was recrystallized from acetone to give 6.31 g (76% yield) of product B.

Diethyl cyanomethylphosphonate (5.2 g, 29.6 mmol) was slowly added to a suspension of sodium hydride (1.2 g, 29.6 mmol) in N,N-dimethylformamide (100 ml). After 30 minutes the ketone B was added to the solution and stirred an additional 6 hr. The reaction mixture was quenched with water and partitioned between water and ether. The combined organic layers were washed with brine and dried over anhydrous magnesium sulfate. The solvent was evaporated in vacuo to give a yellow oil.

In a glass bomb, the oil was dissolved in ethanol (100 ml) and 10N NaOH (20 ml). A catalytic amount of rhodium suspended on alumina (ca. 35 mol percent) was added to the solution. The reaction mixture was shaken under 60 psi $H_2$ for 24 hr on a Parr Hydrogenator. After filtering off excess catalyst, the solution was extracted with chloroform. The combined organic layers were washed with brine and dried over anhydrous magnesium sulfate. After filtration and evaporation of the solvent in vacuo, the oil was taken up in tetrahydrofuran (100 ml). Diborane (23.4 ml, 1.0M) was added and the solution was refluxed for 1.5 hr. The solvent was evaporated in vacuo and 6N HCl (50 ml) was added carefully. The solution was refluxed for 1 hr. After cooling, the mixture was basified with 10N NaOH to pH 14 and partitioned between dichloromethane and water. The combined organic layers were dried over anhydrous magnesium sulfate and filtered. After evaporation of the solvent, the yellow oil was run through a silica gel column in chloroform and methanol. The solvent was evaporated in vacuo to give a yellow oil. GC/EI-MS ($R_t$=8.15 min) m/z (rel. intensity) 263 (17), 246 (21), 211 (84), 196 (33), 183 (100), 165 (19), 133 (19). The oil was then acidified with hydrogen chloride in diethyl ether. Evaporation of the ether afforded 0.96 g of a white solid, Compound 30, as the hydrochloride salt.

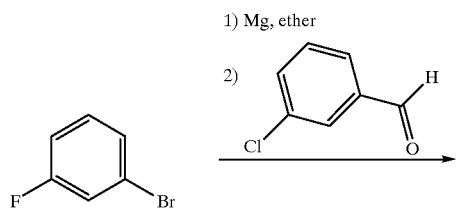

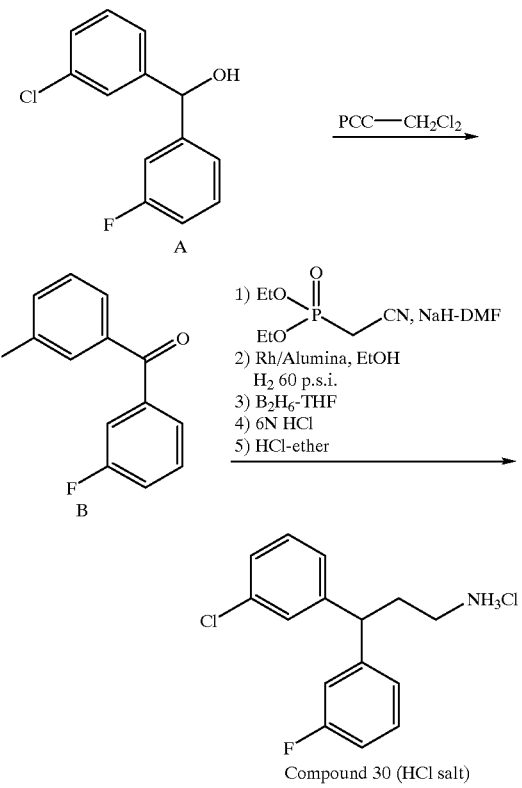

Synthesis of Compound 35 was accomplished as described below. Compounds 36–37 were prepared in a similar manner.

A solution of 3-fluorobenzaldehyde (3.0 g, 24.2 mmol) at 0° C. in 150 ml diethyl ether was treated with 3.0 M ethyl magnesium chloride (12.7 ml, 25.4 mmol) in tetrahydofuran (THF) via syringe. After 4 hr, the reaction mixture was quenched with water and partitioned between water and ether. The combined organic layers were washed with brine and dried over anyhydrous magnesium sulfate to afford 4.25 g of product A.

Pyridinium chlorochromate (6.53 g, 30.3 mmol) was added to a solution of A in dichloromethane (100 ml) and stirred 18 hr. Diethyl ether (300 ml) was added to the reaction mixture and the black solution was filtered through a silica gel plug (30 cm) and washed with an additional 500 ml ether. After evaporation of the solvent the solid was recrystallized from acetone to give 3.05 g of product B. The solvent was evaporated in vacuo to give a pale yellow oil.

Diethyl cyanomethylphosphonate (4.7 g, 26.4 mmol) was slowly added to a suspension of sodium hydride (1.1 g, 26.4 mmol) in 100 ml N,N-dimethylformamide. After 30 minutes the ketone B was added to the solution and stirred an additional 6 hr. The reaction mixture was quenched with water and partitioned between water and ether. The combined organic layers were washed with brine and dried over anhydrous magnesium sulfate. The solvent was evaporated in vacuo to give a yellow oil.

In a glass bomb, the oil was dissolved in 100 ml ethanol and 20 ml 10N NaOH. A catalytic amount of Raney Nickel suspended in water (ca. 15 mol percent) was added to the solution. The reaction mixture was shaken under 60 psi $H_2$ for 24 hr on a Parr Hydrogenator. After filtering off excess catalyst, the solution was extracted with chloroform. The combined organic layers were washed with brine and dried over anhydrous magnesium sulfate. After filtration, the oil was run through a silica gel column in chloroform and methanol. The solvent was evaporated in vacuo to give a pale yellow oil. GC/EI-MS (R$_t$=3.45 min) m/z (rel. intensity) 167 (4), 150 (63), 135 (58), 109 (100), 96 (53), 75 (48). The oil was then acidified with hydrogen chloride in diethyl ether. Evaporation of the ether left a pale yellow solid that was recrystallized in hot acetonitrile to afford 2.2 g of Compound 35, as the hydrochloride salt.

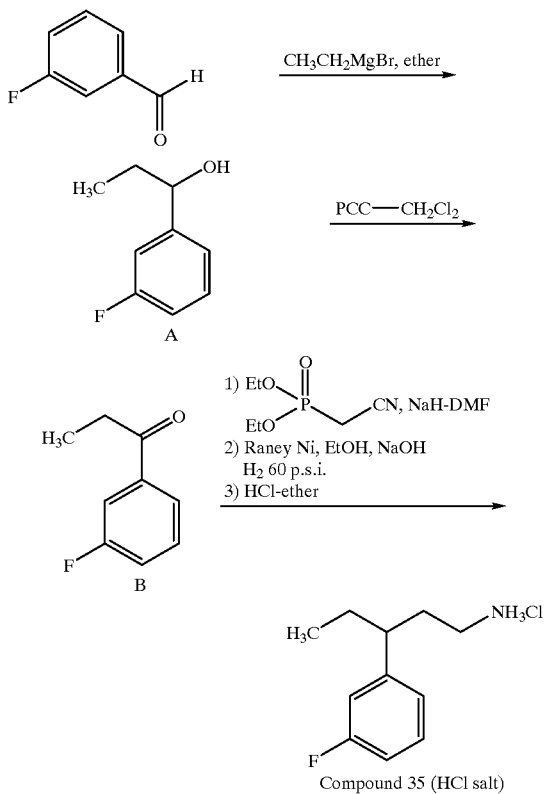

Compound 35 (HCl salt)

Synthesis of Compound 38 was accomplished as described below.

To a solution of 3,3-bis(3-fluorophenyl)-propionitrile (1.5 g, 6.17 mmol) in 250 ml of THF at −70° C. was added butyl lithium (4.25 ml in hexanes, 6.8 mmol) by syringe over 5 minutes. The solution was stirred for 5 min then methyl iodide (1.75 g, 12.3 mmol) was added over 1 min. The reaction mixture was then allowed to warm up to room temperature. Worked up by diluting with ether and washing with 5% HCl and water. The ether layer was dried over sodium sulfate and evaporated to give 1.5 g of the methylated nitrile as a yellow oil.

To the 3,3-bis(3-fluorophenyl)-2-methyl-propionitrile (1.46 g, 5.7 mmol) in 50 ml of dichloromethane at 0° C. was added diisobutylaluminum hydride (1.02 ml, 5.7 mmol) by syringe over a 10 min period. The reaction was stirred for 30 min at 0° C. followed by 2 additional hours at room temperature. The reaction was worked up by adding 200 ml of 10% HCl and stirring at 40° C. for 30 min followed by extraction of the product with dichloromethane. The organic layer was dried over sodium sulfate and evaporated to give 1.36 g of the product A.

To a solution of the aldehyde A (1.36 g, 5.23 mmol) in 40 ml of ether at 0° C. was added methylmagnesium bromide (5.23 ml in ether, 5.23 mmol). The reaction was stirred for 3 hr at room temperature, and then quenched with dilute HCl. The ether layer was separated, dried over sodium sulfate and evaporated to give 1.48 g of 4,4-bis(3-fluorophenyl)-3-methylbutan-2-ol.

To a solution of the alcohol (1.4 g, 5.07 mmol) in 300 ml of dichloromethane was added pyridinium chlorochromate (1.2 g, 5.58 mmol), and the mixture was stirred overnight. The reaction was then diluted with 100 ml of ether and filtered through a silica plug. The solvent was evaporated to give 1.39 g of product B.

The ketone B (1.3 g, 4.9 mmol) was added to a solution of methoxylamine hydrochloride (0.45 g, 5.38 mmol) and pyridine (0.44 ml, 5.38 mmol) in 30 ml of ethanol, and stirred overnight. The ethanol was then evaporated, and the residue taken up in ether and 10% HCl. The ether layer was separated, washed once with 10% HCl, dried over sodium sulfate and evaporated to give 1.4 g of the O-methyl oxime.

To a suspension of sodium borohydride (0.87 g, 23.1 mmol) in 5 ml of THF was added zirconium tetrachloride (1.35 g, 5.8 mmol), and the solution was stirred for 15 min followed by the addition of another 5 ml of THF. The O-methyl oxime (1.4 g, 4.6 mmol) in 5 ml of THF was then added, and the mixture stirred overnight. The THF was removed by evaporation in vacuo, and the residue treated with 10% sodium hydroxide. After the bubbling ceased ether was added and the layers separated. The aqueous layer was extracted four times with ether, and the combined ether extracts were dried over sodium sulfate. The ether was evaporated to give 1.25 g of Compound 38.

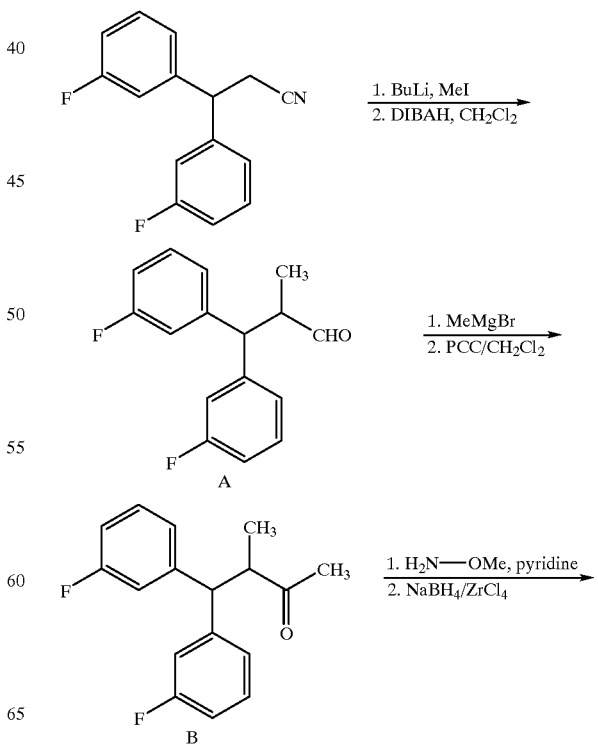

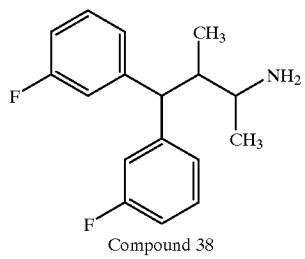

Compound 38

Compound 32 and Compounds 39–53 were synthesized according to standard procedures as described above.

Compound 50 was also prepared using the chiral synthesis described below.

To an ice cold solution of N-benzyl-(S)-α-methylbenzylamine (18.0 g, 85.2 mmol) in THF (75 ml) was added butyl lithium (2.5 M in hexane) (37.5 ml, 93.8 mmol) via a syringe over a period of 10 min at such a rate as to keep the reaction temperature below 10° C. during the addition. The reaction was then stirred at 0° C. for 15 min. The reaction was cooled to −78° C. in a dry ice/isopropanol bath and then a solution of benzyl crotonate (15.0 g, 85.2 mmol) in THF (100 ml) was added dropwise over a period of 45 min. The reaction was stirred at −78° C. for 15 min, and then saturated NH$_4$Cl (50 ml) was added. The reaction mixture was then quickly transferred to a separatory funnel containing saturated NaCl (500 ml) and ether (200 ml). The layers were separated and the aqueous layer extracted with ether (200 ml). The combined organic layers were dried, evaporated, and chromatographed on silica gel (50 mm×30 cm) (hexane/ethyl acetate [20:1]) to yield 21.0 g, 63.7% of product A. $^1$H-NMR showed that the diastereoselectivity of the reaction is >90%.

A mixture of magnesium (2.58 g, 106 mmol), THF (200 ml), and 1-bromo-3-fluorobenzene (18.60 g, 106.3 mmol) was refluxed for 45 min. While still under reflux, product A (16.45 g, 42.45 mmol) was added via syringe with THF (25 ml) over a 2 min period. The reaction was refluxed for 1 hr, and then allowed to cool to room temperature. Saturated NH$_4$Cl(aq) (200 ml) was added. The reaction mixture was then transferred to a separatory funnel containing saturated NaCl(aq) (500 ml) and diethyl ether (200 ml). The layers were separated and the aqueous layer extracted with ether (200 ml). The combined organic layers were dried over sodium sulfate and evaporated to give 21.41 g of product B as a yellow liquid.

Product B (20.02 g, 42.45 mmol, theoretical) was dissolved in acetic acid (120 ml) and sulfuric acid (30 ml). The reaction was stirred at 90° C. for 1 hr. The acetic acid was rotary evaporated giving a brown sludge. This material was placed in an ice bath and cold water (400 ml) was added. The product immediately precipitated. To the reaction was slowly added 10 N NaOH (150 ml) to neutral pH. Diethyl ether (200 ml) was added to this mixture. The mixture was shaken until there was no undissolved material. The ether layer was separated, washed with water (2×100 ml), dried over sodium sulfate, and rotary evaporated yielding 13.14 g (68.2% based on ester) of a thick brown oil. This oil was taken up in ether and converted to the hydrochloride salt with hydrogen chloride in diethyl ether to give product C as a yellow-white solid.

Product C (7.17 g, 14.6 mmol) was taken up in absolute ethanol (200 ml). Pearlman's catalyst (Pd(OH)$_2$/C; 2.00 g) was added. The reaction was shaken under 70 psi hydrogen gas at 70° C. for 20 hr, and the reaction mixture was filtered through Celite. The filtrate was rotary evaporated to give 3.54 g of a light yellow glass. This material was taken up in diethyl ether (100 ml) and was basified with 1 N NaOH (25 ml). The ether layer was washed with water (1×25 ml), dried over sodium sulfate, and rotary evaporated to give 2.45 g of a light yellow oil. This material was Kugelrohr distilled (90–100° C., 1 mm Hg) to give 1.17 g of a colorless liquid. This material was taken up in diethyl ether and converted to the hydrochloride salt with ethereal hydrogen chloride. After rotary evaporation, the salt was recrystallized from 0.12 N HCl (200 mg/ml). The crystals were filtered off and were washed with cold 0.12 N HCl yielding 0.77 g (18%) of Compound 50 as silvery white crystals (as the hydrochloride salt).

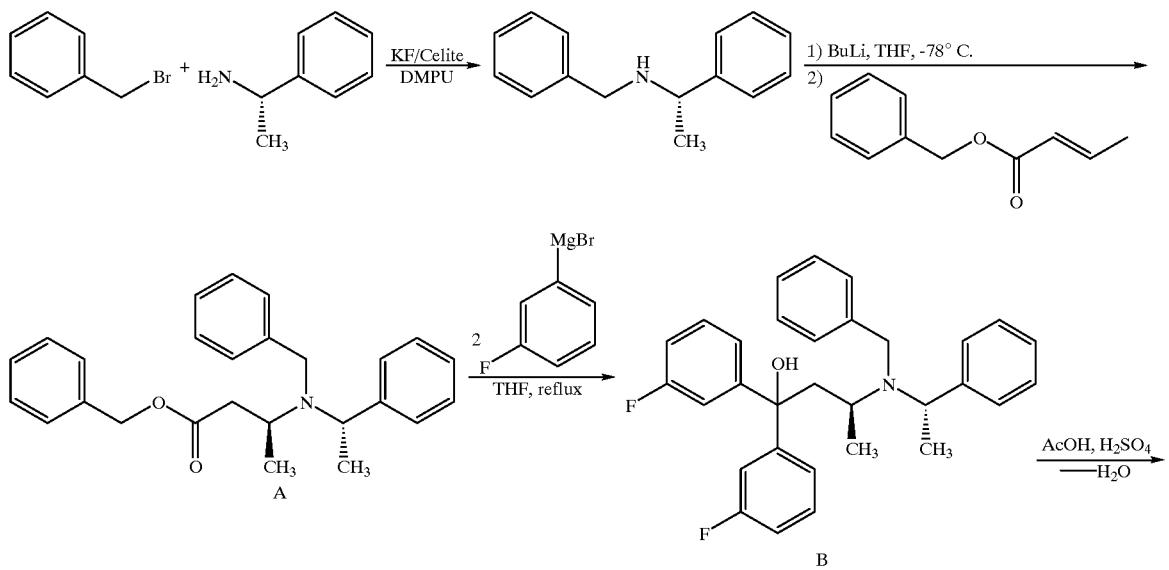

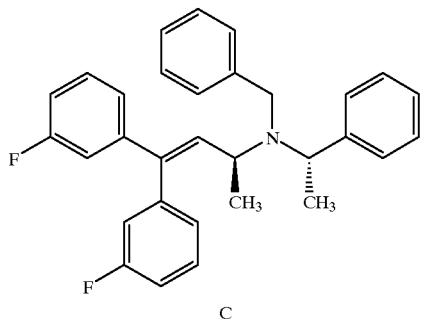

Synthesis of Compound 54 was accomplished as described below.

To a solution of 3,3'-difluorobenzophenone (5 g, 22.9 mmol) and methyl cyanoacetate (3.4 g, 34.4 mmol) in 15 ml of ether was added titanium isopropoxide (16.9 ml, 57.25 mmol). This solution was stirred for 6 days at room temperature then quenched with 0.5 mol of HCl in 300 ml of water. The mixture was diluted with 100 ml of ether, and the layers separated. The ether layer was washed with 5% HCl and saturated brine, then dried over sodium sulfate. The solvents were evaporated in vacuo to give 8 g of product A.

Compound A was dissolved in 50 ml of isopropanol, followed by the addition of a small amount of bromocresol green. Sodium cyanoborohydride (1.52 g, 24.2 mmol) was added all at once followed immediately with the dropwise addition of concentrated HCl, added at such a rate as to keep the solution yellow. After 2 hours the reaction was worked up by partitioning between ether and water. The ether layer was washed with water and saturated brine, dried over sodium sulfate, and concentrated to give the product B.

To a solution of lithium aluminum hydride (30.4 ml, 30.4 mmol) in THF was added product B (1 g, 3.04 mmol) in 2 ml of THF over a period of 30 seconds. This solution was stirred overnight at room temperature, then quenched with the addition of 20 ml of ethyl acetate. The solvents were then removed in vacuo, and the resulting oil was dissolved in aqueous HCl and acetonitrile. The product was then purified on a C-18 column with a gradient of 0.1% HCl to acetonitrile to give 82 mg of Compound 54, as the hydrochloride salt. EI-MS m/z (relative intensity) 277 (M$^+$, 100), 260 (2.4), 242 (8.6), 229 (28), 215 (11.7), 204 (16), 183 (12), 133 (9.5), 124 (14), 109 (6.8), 30 (22).

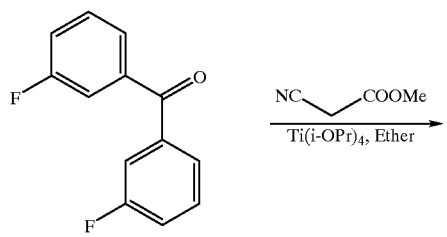

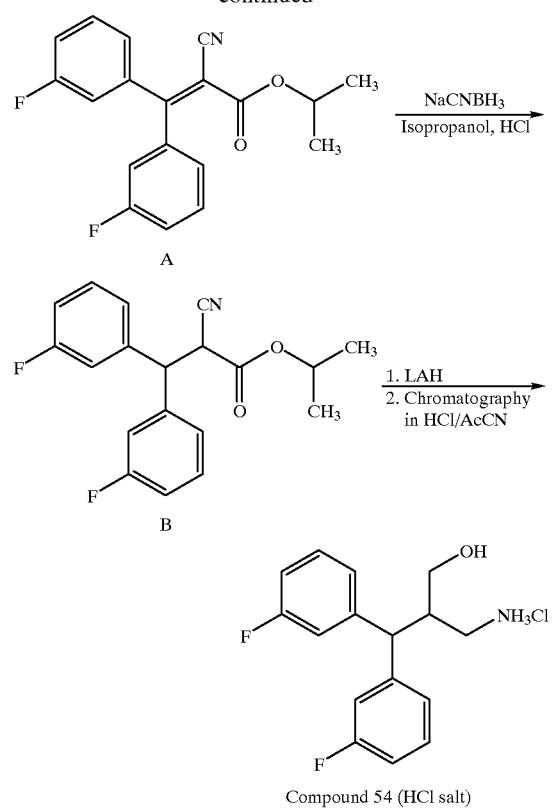

Compound 55 was synthesized analogously to Compound 21 except that ethyl iodide was used in the alkylation step. GC/EI-MS (R$_t$=7.43 min) m/z (relative intensity) 275 (M$^+$, 100), 258 (66), 229 (63), 204 (57), 201 (72), 183 (84), 134 (57), 124 (68), 109 (98), 72 (72).

The synthesis of Compound 56 was accomplished as follows.

The alcohol A was synthesized from 3-fluorobromobenzene and 3-fluoro-2-methylbenzaldehyde as described for product A in the synthesis of Compound 24.

The alcohol A (8.4 g, 36.2 mmol) was stirred with manganese dioxide (12.6 g, 144.8 mmol) in 100 ml of dichloromethane for 4 days. The reaction mixture was then diluted with ether and filtered through a 0.2 micron teflon membrane filter. The filtrate was concentrated to give 7.6 g of the ketone B.

The substituted acrylonitrile C was synthesized as described for product A in the Compound 20 synthesis.

To the nitrile C (4 g, 15.7 mmol) in 240 ml of ethanol was added 2 g of 10% palladium dihydroxide on carbon. This mixture was hydrogenated at 60–40 psi for 3 days. The reaction mixture was then filtered and concentrated. The resulting oil was dissolved in chloroform and chromatographed on silica gel (30% methanol/5% isopropylamine in chloroform) to give the amine. This amine was dissolved in aqueous HCl/acetonitrile and purified via HPLC on C-18 (10% acetonitrile/0.1% HCl to 50% acetonitrile/0.1% HCl over 60 min) then lyophilized to give 800 mg of Compound 56, as the hydrochloride salt. GC/EI-MS ($R_t$=7.39 min) m/z (relative intensity) 261 ($M^+$, 64), 244 (56), 229 (57), 215 (100), 203 (53), 183 (21), 133 (39), 122 (31), 109 (32).

To a solution of 5-fluoro-2-methylbenzonitrile (5 g, 37 mmol) in 50 ml of THF was added 3-fluorophenylmagnesium bromide (46 ml, 40 mmol) and copper (I) cyanide (0.072 g, 0.8 mmol). This solution was refluxed for 4 hours, then poured into ether/20% HCl and stirred for a further 2 hours. The layers were separated, and the ether layer washed with water and saturated brine. The solution was dried over sodium sulfate and concentrated. The crude oil was purified on silica (hexane to 50% dichloromethane in hexane over 60 min) to give 6.7 g of the ketone A.

The ketone A was converted to Compound 57 as described for Compound 56. GC/EI-MS ($R_t$=7.35 min) m/z (relative intensity) 261 ($M^+$, 52), 244 (41), 229 (67), 215 (100), 203 (42), 201 (42), 183 (21), 133 (45), 122 (28), 109 (26).

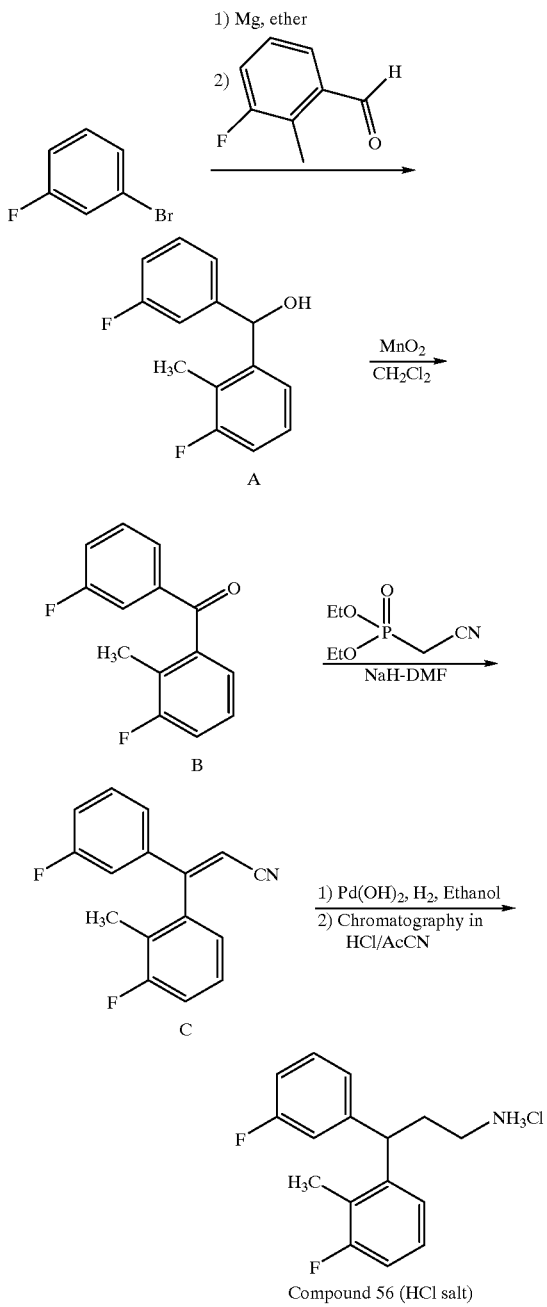

Compound 56 (HCl salt)

The synthesis of Compound 57 was accomplished as follows.

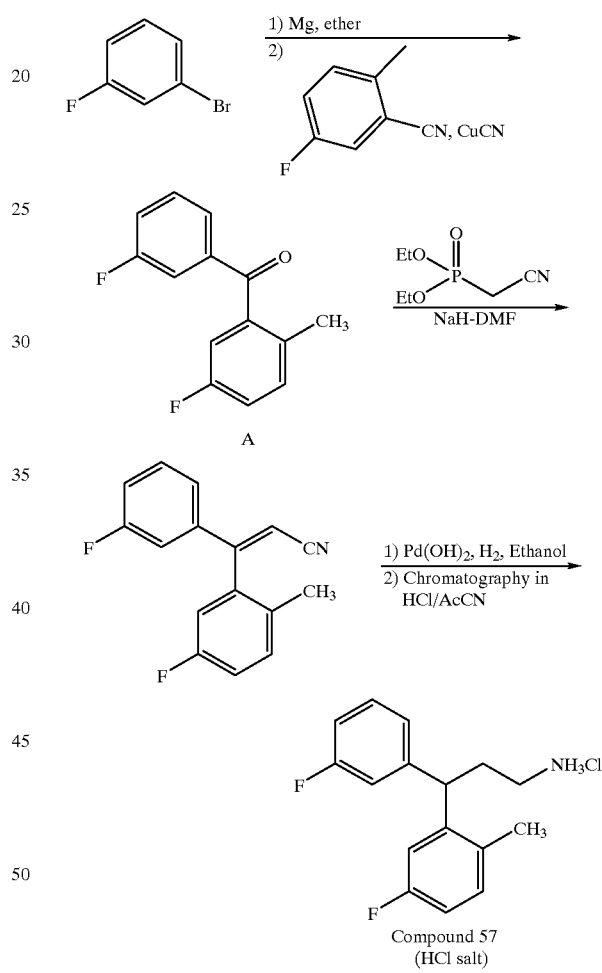

Compound 57 (HCl salt)

The synthesis of Compound 58 was accomplished as follows.

To a solution of 5-fluoro-2-methylbenzoyl chloride (2.24 g, 13 mmol) in 10 ml of dry THF was added iron III acetylacetonate (0.16 g, 0.44 mmol). The solution was cooled to 0° C., and a THF solution of 5-fluoro-2-methylphenylmagnesium bromide (20 ml, 15.5 mmol) was added by syringe over a period of 30 min. The reaction was stirred for another 30 min, then poured slowly into ether/5% HCl. The ether layer was separated, washed with saturated brine, dried over sodium sulfate, and concentrated to give 3.2 g of ketone A.

Dry THF (30 ml) was cooled to −78° C. followed by the addition of butyl lithium (5.85 ml, 14.6 mmol, 2.5 M solution in hexanes). Acetonitrile (0.76 ml, 14.62 mmol) was then added over a period of 2 min, then allowed to stir at −78° C. for 15 min. To this solution was added ketone A (3 g, 12.2 mmol) in 5 ml of THF. The solution was stirred for 30 min at −78° C. then allowed to warm to room temperature and stirred overnight. The reaction mixture was partitioned between ether and 5% HCl. The ether layer was separated, washed with saturated brine, dried over sodium sulfate, and concentrated to give 2.2 g of the nitrile B.

The nitrile B (1 g, 3.48 mmol) was dissolved in 30 ml of ethanol and 3 ml of 10 N sodium hydroxide. To this solution was added 1 g of a 50% aqueous slurry of Raney nickel, and the mixture was hydrogenated at 60 psi for 20 hours. The reaction was filtered and concentrated to a white solid. This residue was taken up in ether/water and the ether layer separated. The ether solution was dried over sodium sulfate and concentrated to give 0.96 g of the hydroxy amine C.

The hydroxy amine C (0.96 g, 3.3 mmol) was taken up in concentrated HCl and heated to 70° C. which caused brief solution, and then precipitation of the alkene D. The alkene was collected by filtration and dissolved in 30 ml of ethanol and 1 ml of conc. HCl. Palladium dihydroxide on carbon (0.4 g) was added to the solution, and the mixture hydrogenated at 60 psi for 24 hours. The product was isolated by filtering off the catalyst and evaporating the solvent. The residue was dissolved in 0.1% HCl and acetonitrile, and purified on C-18 (15% acetonitrile/0.1% HCl to acetonitrile) to give 0.6 g of Compound 58, as the hydrochloride salt. GC/EI-MS ($R_t$=7.82 min) m/z (relative intensity) 275 ($M^+$, 100), 258 (20), 243 (74), 229 (38), 214 (65), 201 (31), 196 (32), 183 (20), 148 (35), 138 (42), 133 (48), 122 (69), 109 (41).

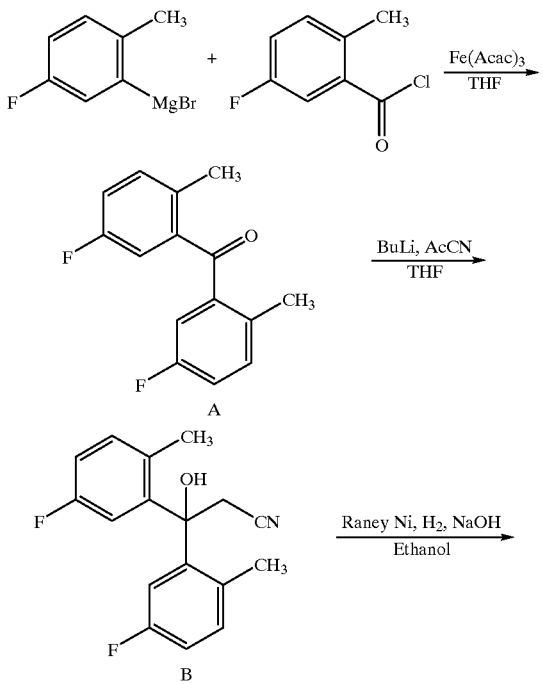

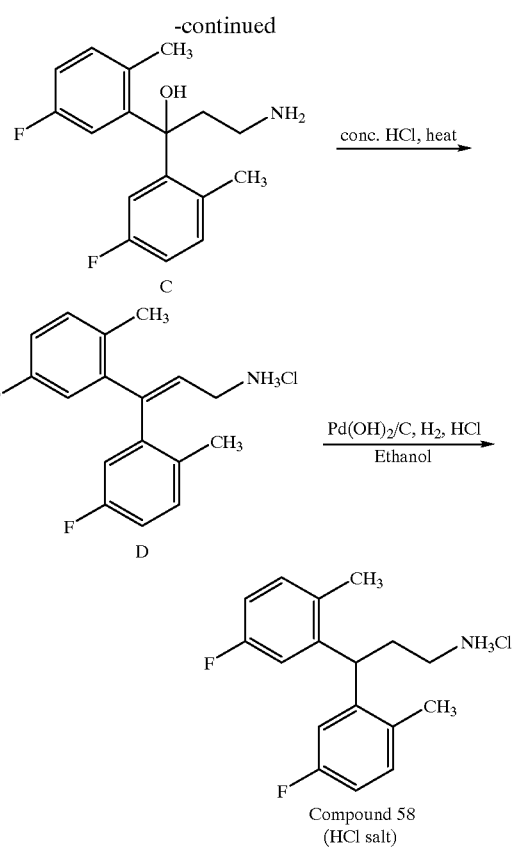

Synthesis of Compound 59 was accomplished as follows.

Compound 20 (2.0 g, 7.05 mmol) was dissolved in abs. EtOH (200 ml) and cooled to 5–10° C. in an ice bath. Acetaldehyde (0.395 ml, 7.05 mmol, cooled to −4° C.) was added followed by nickel-aluminum alloy (200 mg, Fluka Chemika), and the reaction was hydrogenated on a Parr apparatus at 50 psi for 2 hr. GC/MS showed 75% yield of the product and 2% of the N,N-diethyl side-reaction product. The reaction mixture was filtered through diatomaceous earth and the filtrate was evaporated under reduced pressure. The crude product was dissolved in isopropanol (5 ml)/ether (60 ml)/ethereal HCl (1 M), and then hexane (5 ml) was added to the cloud point. The cloudy mixture was filtered through paper, then hexane (10 ml) was added to the cloud point, and the solution was filtered again. The filtrate was stoppered and the product was allowed to crystallize at room temperature. The crystals were collected and dried to provide 0.325 g (14.8% yield) of Compound 59, as the hydrochloride salt (colorless needles).

The synthesis of Compound 60 was accomplished as follows. Compound 66 was synthesized in a similar manner starting from Compound 33 or 34 (the more active isomer was used; the chirality is unknown at this time).

Compound 20 (as the free base) (1.0 g, 4.0 mmol) was refluxed in ethyl formate (150 ml) for 2 hr. The solvent was then removed under reduced pressure to provide 1.1 g, 99% yield of formamide A as a colorless oil. GC/MS showed the product to be 100.0% pure and was used in the following step without further purification.

The formamide A (1.1 g, 4.0 mmol) was dissolved in dry THF (100 ml) and heated to reflux (no condenser). Borane-methyl sulfide complex (1.2 ml, 12 mmol, 10.5 M) was added dropwise over a period of 3 min to the refluxing solution. Reflux was maintained for approximately 15 min, open to the air, until the reaction volume was reduced to approximately 30 ml. The reaction was then cooled in an ice bath, and ice (5 g, small pieces) was carefully added followed by H₂O (25 ml) and conc. HCl (25 ml). The acidic solution was refluxed for 30 min. The reaction mixture was then cooled in an ice bath, basified with NaOH (10N), extracted with ether (3×100 ml), dried (Na₂SO₄, anhydrous), and evaporated under reduced pressure. The crude product was dissolved in ether (10 ml)/hexane (50 ml) and ethereal HCL (1 M) was added dropwise to precipitate the hydrochloride salt. The salt was collected and recrystallized from isopropanol (3 ml)/ether (40 ml) to provide 0.5 g of Compound 60, as the hydrochloride salt.

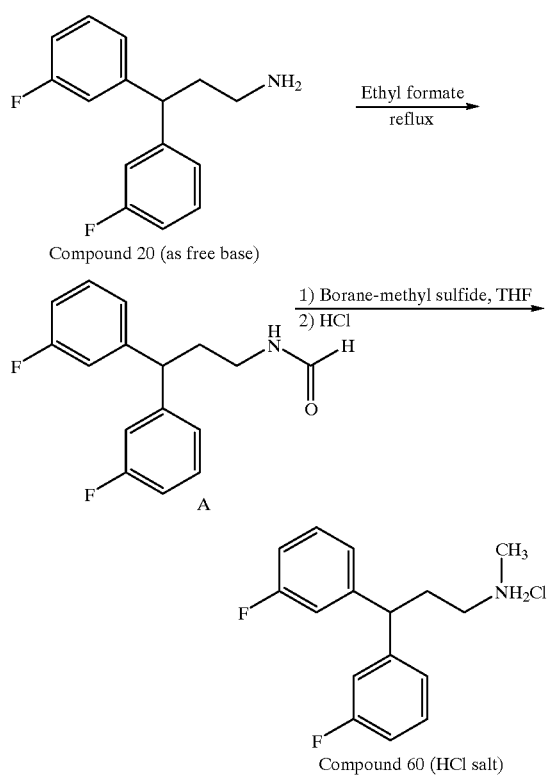

Compound 61 was prepared from 2-bromo-4-fluoroanisole and 3-fluorobenzaldehyde as described for Compound 24. GC/EI-MS ($R_t$=9.22 min) m/z (relative intensity) 277 (M⁺, 74), 260 (46), 245 (35), 231 (44), 229 (34), 217 (24), 203 (28), 201 (31), 183 (28), 154 (24), 133 (19), 109 (100).

Compound 62 was prepared from 2-bromoanisole and 2-methoxybenzaldehyde as described for Compound 24. GC/EI-MS ($R_t$=9.30 min) m/z (relative intensity) 271 (M⁺, 100), 254 (17), 240 (23), 225 (40), 223 (45), 207 (22), 181 (32), 165 (31), 136 (48), 121 (98), 91 (83).

The synthesis of Compound 63 was accomplished as follows.

Alcohol A was obtained from 3-fluorobenzaldehyde as described for product A of the Compound 24 synthesis.

To alcohol A (10.275 g, 47 mmol) in 200 ml of ethanol was added 1.6 g of 10% Pd/C and 1 ml of concentrated HCl. This mixture was hydrogenated for 3 hr at 60 psi, then filtered and concentrated to give the diphenylmethane B.

Product B (2.01 g, 9.86 mmol) was dissolved in 20 ml of THF and cooled to −78° C. Butyl lithium (4.4 ml, 10.8 mmol, 2.5 M in hexanes) was added slowly by syringe, and then the reaction stirred for another 30 min at −78° C. To this orange solution was added cyclopentene oxide (0.9 ml, 10.3 mmol) . The reaction was allowed to stir 3 hours while warming slowly to room temperature. The reaction was quenched with 150 ml of 10% HCl and extracted 3 times with ether. The ether layer was dried over sodium sulfate and concentrated to give 2.5 g of the alcohol C.

To the alcohol C (1 g, 3.5 mmol) in 10 ml of dry THF was added triphenylphosphine (1.37 g, 5.2 mmol) in 5 ml of THF and p-nitrobenzoic acid (0.87 g, 5.2 mmol) in 5 ml of THF. This solution was cooled to 0° C. followed by the addition of DEAD (0.82 ml, 5.2 mmol), and allowed to stir overnight. The reaction was partitioned between water and ether. The ether was removed in vacuo and the resulting oil was chromatographed on silica gel in hexane/ethyl acetate to yield 365 mg of the cis-ester. This ester was hydrolyzed in methanol with potassium carbonate by stirring overnight. After removal of the methanol, the residue was taken up in ether, washed with water, dried over sodium sulfate and concentrated to give 250 mg of the cis alcohol D.

To the alcohol D (0.25 g, 0.9 mmol) in 5 ml of dry THF was added triphenylphosphine (342 mg, 1.3 mmol) in 5 ml of THF and phthalimide (191.3 mg, 1.3 mmol) in 5 ml of THF. This solution was cooled to 0° C. followed by the addition of DEAD (0.205 ml, 1.3 mmol), and allowed to stir overnight. The reaction was partitioned between water and ether. The ether was removed in vacuo and the resulting oil was chromatographed on silica gel in hexane/ethyl acetate to yield 100 mg of the phthalimide E.

To a solution of the phthalimide E (100 mg) in 20 ml of ethanol was added 8.8 mg of hydrazine hydrate. The solution was refluxed for 5 hours then stirred at room temperature overnight. The reaction was worked up by adding 1 ml of conc. HCl and filtering off the white solid. The resulting solution was concentrated to dryness and the solid taken up in ether and aqueous sodium hydroxide. The ether layer was dried over sodium sulfate and concentrated to a white solid. This was taken up in a small amount of ether and treated with 10 drops of 1M HCl in ether. After stirring overnight, the white solid was collected by filtration and dried to give 50 mg of Compound 63, as the hydrochloride salt. GC/EI-MS ($R_t$=9.22 min) m/z (relative intensity) 287 (M⁺, 45), 270 (12), 201 (63), 183 (81), 133 (38), 109 (43), 83 (44), 56 (100), 43 (37).

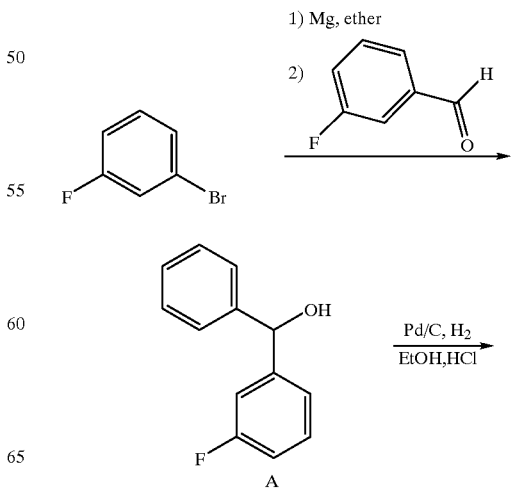

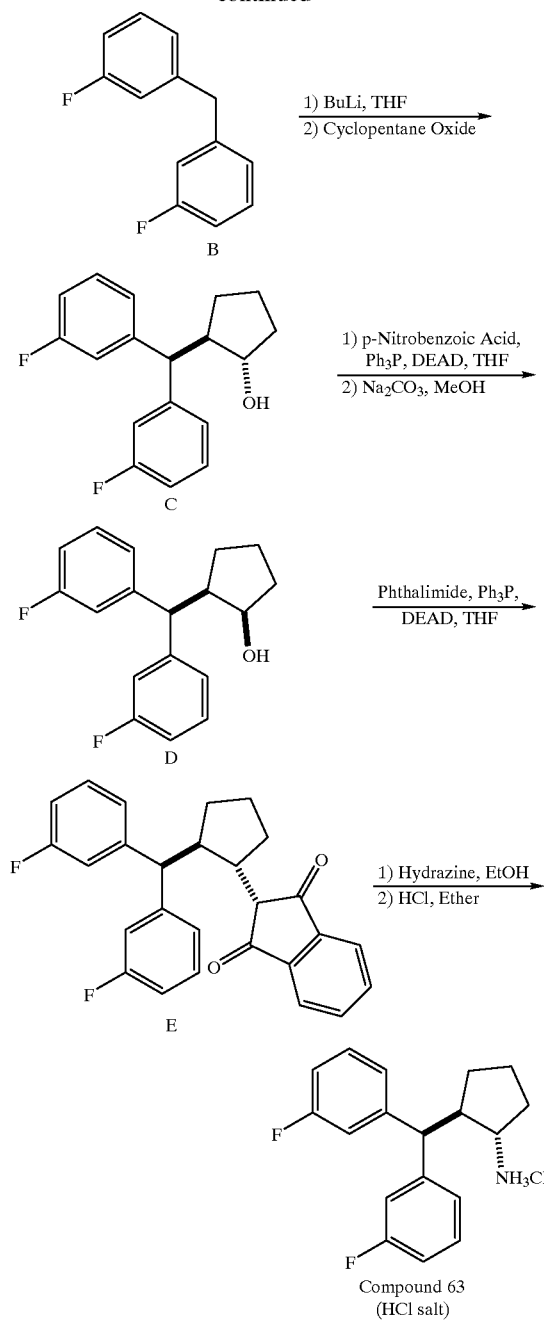

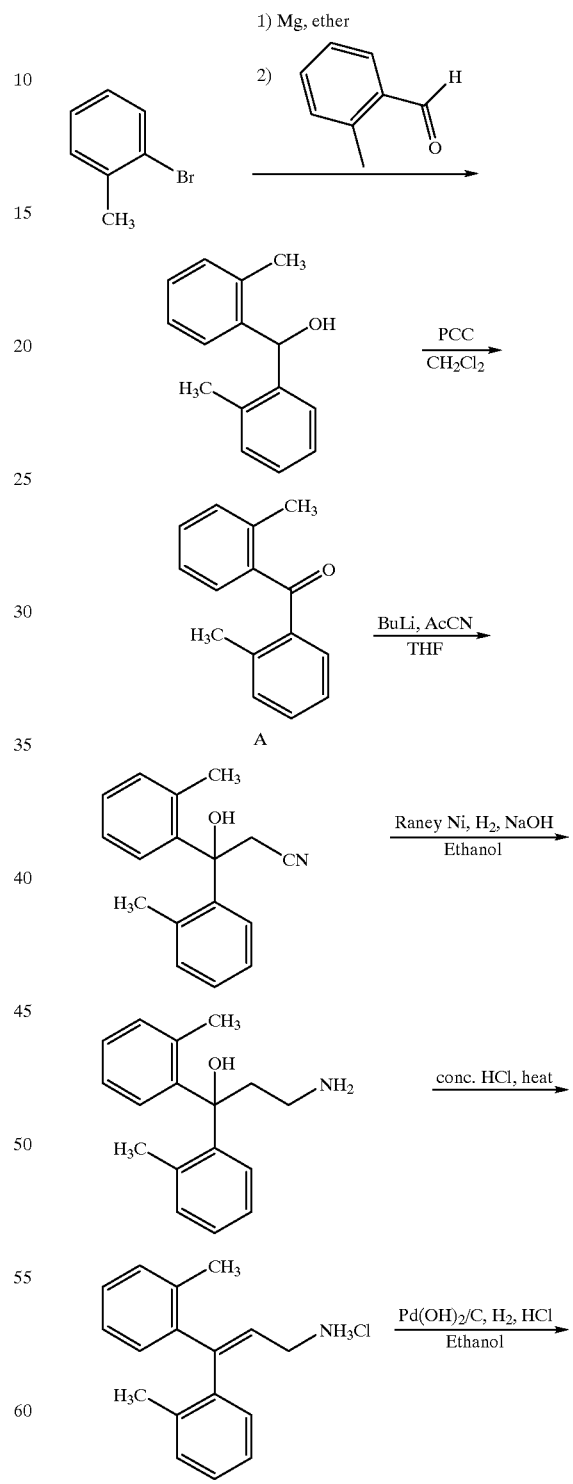

This ketone was converted to the final product using the procedure outlined for Compound 58. GC/EI-MS ($R_t$=7.84 min) m/z (relative intensity) 239 ($M^+$, 88), 222 (14), 207 (100), 193 (46), 178 (71), 165 (60), 130 (39), 120 (40), 115 (51), 104 (40), 91 (38), 77 (21).

The synthesis of Compound 64 was done as described for Compound 63 except that the inversion step (product C to D) was omitted in order to obtain the cis amine as the final product. GC/EI-MS ($R_t$=8.28 min) m/z (relative intensity) 287 ($M^+$, 15), 270 (4), 201 (13), 183 (15), 133 (11), 109 (16), 84 (43), 56 (100), 43 (32).

The synthesis of Compound 65 was accomplished as follows.

The ketone A was synthesized similarly to ketone B in the Compound 24 synthesis using 2-methylphenylmagnesium bromide and 2-methylbenzaldehyde as starting materials.

-continued

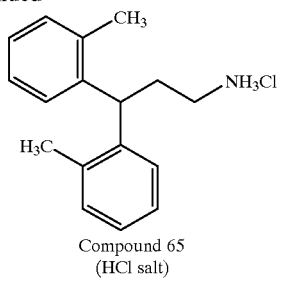

Compound 65
(HCl salt)

Example 30

Biological Properties of Synthesized Arylalkylamines

Compounds synthesized as described in Example 28 and Example 29 were tested for various biological properties detailed in the examples.

TABLE 1

| Compound | $IC_{50}$ ($\mu$M) vs. NMDA[a] | $IC_{50}$ ($\mu$M) vs. [$^3$H]MK-801[c] |
|---|---|---|
| Compound 1 | 0.102 (7) | 126 (4) |
| Compound 2 | 0.192 (4) | not tested |
| Compound 3 | 0.003 (7) | not tested |
| Compound 4 | 0.184 (5) | 89 (1) |
| Compound 5 | 0.102 (1) | 15.2 (2) |
|  | 0.070 (3)[b] |  |
| Compound 6 | 0.129 (1) | >100 (1) |
|  |  | (0% at 100 $\mu$M)[d] |
| Compound 7 | 0.163 (2) | 129 (1) |
| Compound 8 | 0.099 (2) | 219 (1) |
| Compound 9 | 1.2 (5) | >100 (2) |
|  |  | (10% at 100 $\mu$M)[d] |
| Compound 10 | 0.082 (2) | ~80 (1) |
|  |  | (57% at 80 $\mu$M)[d] |
| Compound 11 | 4.0 (2) | not tested |
| Compound 12 | 6.0 (11) | 98 (1) |
| Compound 13 | not tested | not tested |
| Compound 14 | 8.8 (2) | ~100 $\mu$M |
| Compound 15 | 4.9 (3) | ~100 $\mu$M |
| Compound 16 | 5.1 (1) | 28.8 (1) |
| Compound 17 | 9.6 (1) | 36.3 (1) |
| Compound 19 | 5.1 (3) | 34 (1) |
| Compound 19 | 0.435 (11) | 2.1 (5) |
| Compound 20 | 0.057 (9) | 0.385 (4) |
| Compound 21 | 0.029 (2) | 0.602 (1) |
|  | 0.037 (7)[e] | 0.380 (1)[e] |
|  | 0.430 (5)[e] | 4.1 (1)[e] |
| Compound 22 | 0.145 (6) | 1.2 (1) |
| Compound 23 | 0.267 (3) | 5.4 (1) |
| Compound 24 | 0.222 (4) | 0.742 (4) |
| Compound 25 | 0.279 (2) | 0.871 (2) |
| Compound 26 | 27 (2) | 34 (2) |
| Compound 27 | 0.071 (1) | 0.180 (2) |
| Compound 28 | 0.380 (1) | 2.3 (3) |
| Compound 29 | 1.9 (2) | 5.8 (3) |
| Compound 30 | 0.035 (2) | 0.407 (2) |
| Compound 31 | 0.042 (7) | 1.7 (1) |
| Compound 32 | 0.297 (4) | 1.1 (2) |
| Compound 33 | not tested | not tested |
| Compound 34 | not tested | not tested |
| Compound 35 | 6.2 (1) | 25.1 (1) |
| Compound 36 | not tested | not tested |
| Compound 37 | 0.944 (2) | 11.1 (2) |
| Compound 38 | 0.468 (1) | 2.8 (1) |
| Compound 39 | not tested | not tested |
| Compound 40 | not tested | not tested |
| Compound 41 | 0.724 (1) | 14.0 (3) |
| Compound 42 | not tested | not tested |
| Compound 43 | 0.232 (4) | 7.5 (2) |

TABLE 1-continued

| Compound | $IC_{50}$ ($\mu$M) vs. NMDA[a] | $IC_{50}$ ($\mu$M) vs. [$^3$H]MK-801[c] |
|---|---|---|
| Compound 44 | not tested | not tested |
| Compound 45 | not tested | not tested |
| Compound 46 | 0.013 (3) | 5.2 (2) |
| Compound 47 | not tested | not tested |
| Compound 48 | not tested | not tested |
| Compound 49 | not tested | not tested |
| Compound 50 | 0.089 (6) | 0.871 (2) |
| Compound 51 | 1.1 (4) | 4.5 (2) |
| Compound 52 | 0.102 (3) | 0.380 (2) |
| Compounds 53 | 0.217 (3) | 4.2 (2) |
| Compound 54 | 0.036 (4) | 0.046 (3) |
| Compound 55 | 0.035 (3) | 0.153 (2) |
| Compound 56 | 0.218 (4) | 0.955 (2) |
| Compound 57 | 0.028 (4) | 0.063 (2) |
| Compound 58 | 0.028 (2) | 0.203 (3) |
| Compound 59 | 0.272 (2) | 0.453 (3) |
| Compound 60 | 0.724 (3) | 0.923 (2) |
| Compound 61 | 0.134 (4) | 0.324 (2) |
| Compound 62 | 0.177 (5) | 0.617 (1) |
| Compound 63 | 0.093 (6) | 0.245 (3) |
| Compound 64 | 0.309 (3) | 0.851 (2) |
| Compound 65 | 0.167 (3) | 2.0 (1) |
| Compound 66 | 0.236 (4) | not tested |
| Compound 67 | 4.6 (1) | not tested |
| Compound 68 | 2.9 (1) | not tested |
| Compound 69 | not tested | not tested |

[a]: Inhibition of NMDA/glycine-induced increases in intracellular calcium in cultured rat cerebellar granule cells (RCGC's) (see Example 1). (# in parentheses indicates the number of experiments).
[b]: TFA salt.
[c]: Inhibition of [$^3$H]MK-801 binding in rat cortical/hippocanpal washed membrane preparations (see Example 4).
[d]: $IC_{50}$ study incomplete. % inhibition at the stated concentration.
[e]: Enantiomers of Compound 21 (Compounds 33 and 34) whose absolute stereochemistry has not been assigned at this time.

A comparison of the $IC_{50}$ values in the RCGC assay with the $IC_{50}$ values in the [$^3$H]MK-801 binding assay (Table 1) illustrates that the arylalkylamines of the invention inhibit NMDA receptor activity by a mechanism different than that of binding to the MK-801 binding site; the concentration of the compound that inhibits NMDA receptor function is several orders of magnitude less than the concentration that competes at the site labeled by [$^3$H]MK-801. This is not the case, however, with the simplified arylalkylamines exemplified by Compounds 19–69. Such compounds bind to the site labeled by [$^3$H]MK-801 at concentrations ranging approximately 1 to 400-fold higher than those which antagonize NMDA receptor-mediated function in the rat cerebellar granule cell assay.

Compounds 19–69 appear similar in structure to other compounds known in the prior art which are utilized as, for example, anticholinergics, antiparkinsonians, antihistamines, antidepressants, calcium channel blockers, coronary vasodilators, opiate analgesics, and antiarrhythmics. Certain of these prior art compounds have been evaluated for NMDA receptor antagonist potency (Example 1); the results are summarized in Table 2. As can be seen in Table 2, none of the prior art compounds tested, with the exception of (R)- and (S)-fendiline, had $IC_{50}$ values less than 1 $\mu$M.

TABLE 2

| Compound and Therapeutic Utility | Structure | IC$_{50}$ ($\mu$M) vs. NMDA[a] |
|---|---|---|
| (R)-fendiline (calcium channel blocker; coronary vasodilator) | 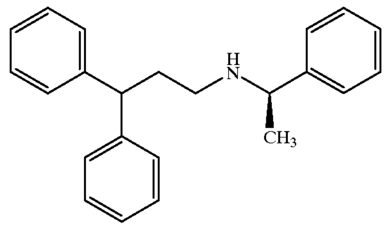 | 0.719 |
| (S)-fendiline (calcium channel blocker; coronary vasodilator) | 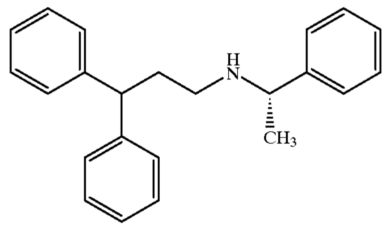 | 0.686 |
| prenylamine (calcium channel blocker; coronary vasodilator) | 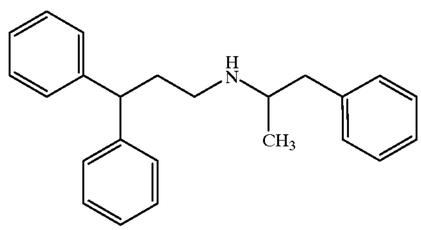 | ~10 |
| pheniramine (antihistamine) | 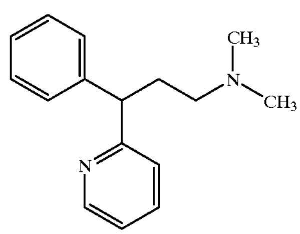 | 22 |
| chlorpheniramine (antihistamine) | 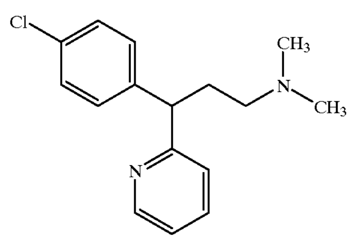 | >100 |
| brompheniramine (antihistamine) | 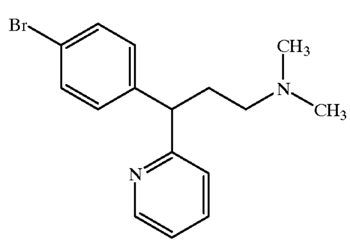 | 138 |

TABLE 2-continued

| Compound and Therapeutic Utility | Structure | IC$_{50}$ ($\mu$M) vs. NMDA[a] |
|---|---|---|
| diphenhydramine (antihistamine) | | 26 |
| doxylamine (antihistamine; hypnotic) | 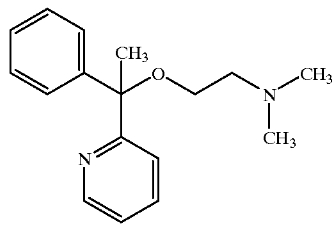 | 62 |
| chlorcyclizine (antihistamine) | 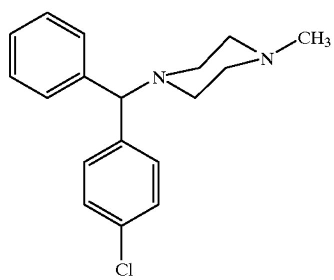 | ~10 |
| cyclizine (antiemetic) | 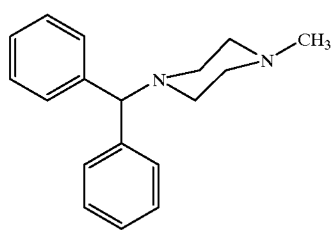 | 28 |
| nor-cyclizine (pharmaceutical intermediate) | 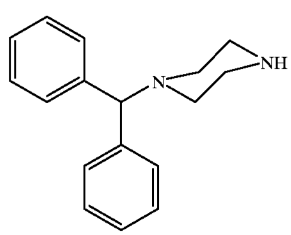 | 23 |
| desipramine (antidepressant) | 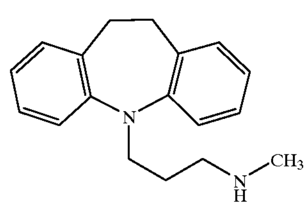 | 2.3 |

TABLE 2-continued
| Compound and Therapeutic Utility | Structure | IC$_{50}$ ($\mu$M) vs. NMDA[a] |
|---|---|---|
| protriptyline (antidepressant) | 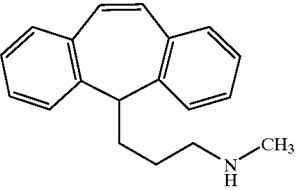 | ≦10 |
| lidoflazine (calcium channel blocker; coronary vasodilator) | 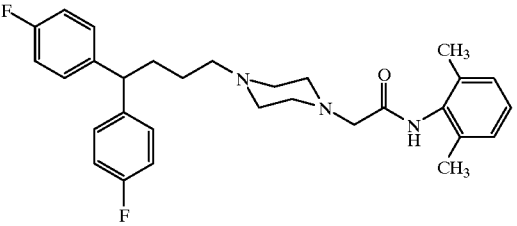 | >30 |
| pimozide (antipsychotic) | 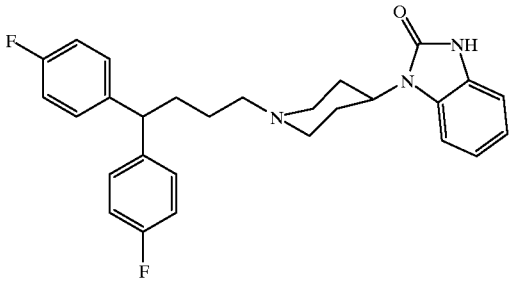 | >10 |
| disopyramide (antiarrhythmic) | 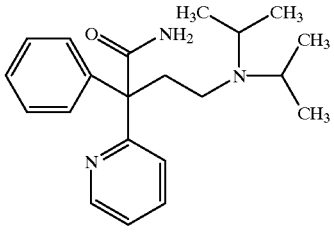 | >100 |
| isopropamide (anticholinergic) | 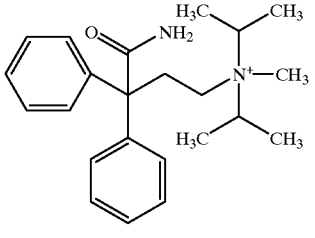 | 87 |
| pridinol (anticholinergic; antiparkinsonian) | 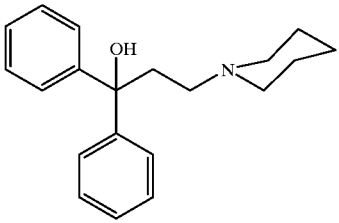 | 10.7 |

TABLE 2-continued
| Compound and Therapeutic Utility | Structure | IC$_{50}$ ($\mu$M) vs. NMDA[a] |
|---|---|---|
| chloropyramine (antihistamine) | 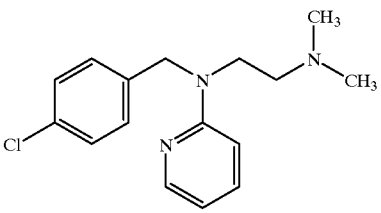 | 76 |
| trihexyphenidyl (anticholinergic; antiparkinsonian) | 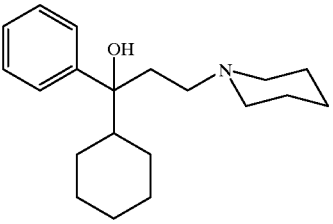 | not tested |
| fluoxetine (antidepressant) | 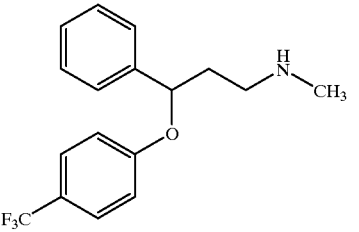 | not tested |
| zimeldine (antidepressant) | 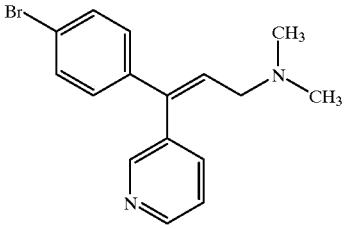 | not tested |
| methadone (opiate analgesic) | 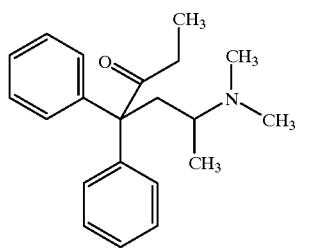 | not tested |
| Astra compound[b] (antidepressant) | 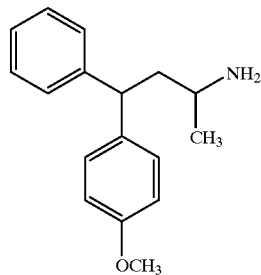 | not tested |

TABLE 2-continued

| Compound and Therapeutic Utility | Structure | IC$_{50}$ ($\mu$M) vs. NMDA[a] |
|---|---|---|
| Novo-Nordisk compound[c] (calcium channel blocker; neuroprotectant) | 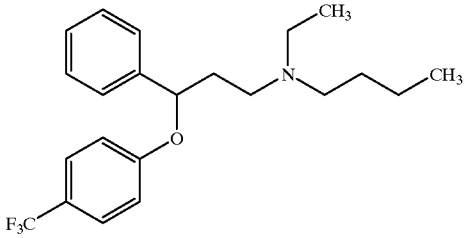 | not tested |

[a]: Inhibition of NMDA/glycine-induced increases in intracellular calcium in cultured rat cerebellar granule cells (RCGC's) (see Example 1).
[b]: Disclosed as compound 2 in Table 4 in Marcusson et al., Inhibition of [³H]paroxetine binding by various serotonin uptake inhibitors: structure-activity relationships. Europ. J. Pharmacol. 215: 191–198, 1992.
[c]: Disclosed as compound 17 in Jakobsen et al., Aryloxyphenylpropylamines and their calcium overload blocking compositions and methods of use. U.S. Pat. No. 5,310,756, May 10, 1994.

Structure-activity relationship studies were initiated using Compound 19 as the lead structure. An examination of the side chain demonstrated that the propyl side chain was optimal for NMDA receptor antagonist potency (Table 3).

TABLE 3

| Compound | Structure | IC$_{50}$ ($\mu$M) vs. NMDA[a] |
|---|---|---|
| 2,2-di-phenyl-ethylamine | 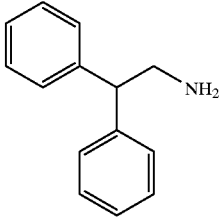 | 24.5 |
| 3,3-di-phenyl-propylamine (Compound 19) | 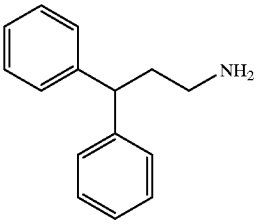 | 0.435 |
| 4,4-di-phenyl-butylamine | 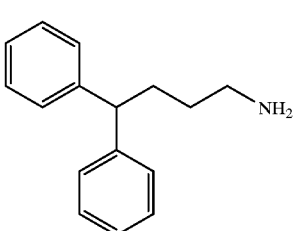 | 1.7 |

TABLE 3-continued

| Compound | Structure | IC$_{50}$ ($\mu$M) vs. NMDA[a] |
|---|---|---|
| 5,5-di-phenyl-pentylamine | 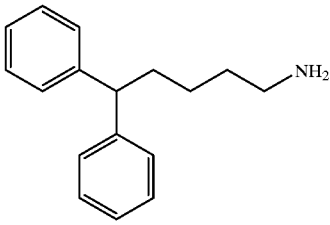 | 6.4 |

[a]: Inhibition of NMDA/glycine-induced increases in intracellular calcium in cultured rat cerebellar granule cells (RCGC's) (see Example 1).

Further SAR studies examined the optimal pattern of phenyl ring substitution. Initial studies demonstrated that substitution of a halogen group (fluoro or chloro) at the meta position was optimal for NMDA receptor antagonist potency (Table 4).

TABLE 4

| Compound | Structure | IC$_{50}$ ($\mu$M) vs. NMDA[a] |
|---|---|---|
| 3-diphenyl-1-propylamine (Compound 19) | 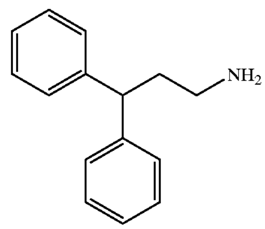 | 0.435 |
| 3-(2-fluorophenyl)-3-(4-fluorophenyl)-1-propylamine | 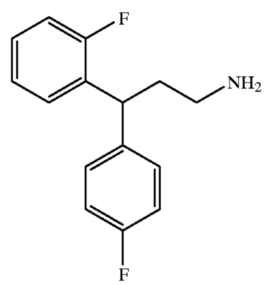 | 0.730 |
| 3,3-bis(4-fluorophenyl)-1-propylamine | 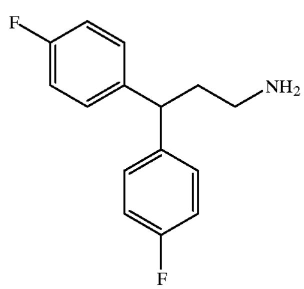 | 5.5 |
| 3,3-bis(3-fluorophenyl)-1-propylamine (Compound 20) | 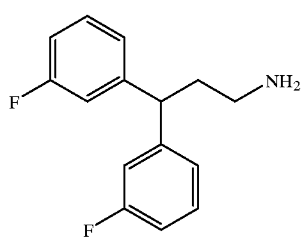 | 0.057 |
| 3-(2-fluorophenyl)-3-(3-fluorophenyl)-1-propylamine (Compound 52) | 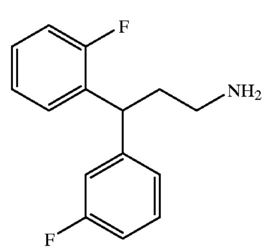 | 0.102 |

TABLE 4-continued

| Compound | Structure | IC$_{50}$ ($\mu$M) vs. NMDA[a] |
|---|---|---|
| 3,3-bis(2-fluorophenyl)-1-propylamine (Compound 53) | 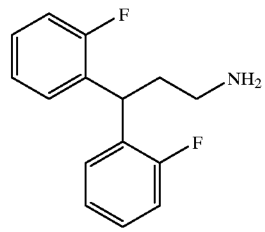 | 0.217 |
| 3,3-bis(3-chlorophenyl)-1-propylamine (Compound 31) | 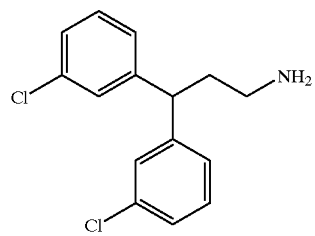 | 0.042 |
| 3-(3-fluorophenyl)-3-(3-chlorophenyl)-1-propylamine (Compound 30) | 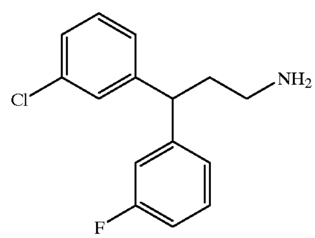 | 0.035 |
| 3,3-bis[3-(trifluoromethyl)phenyl]-1-propylamine | 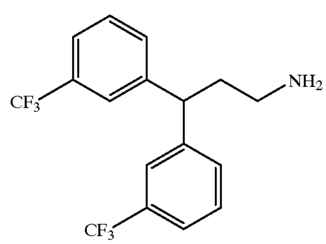 | 10.2 |

[a]: Inhibition of NMDA/glycine-induced increases in intracellular calcium in cultured rat cerebellar granule cells (RCGC's) (see Example 1).

Replacement of one of the fluoro groups on one phenyl ring with a methyl or methoxy group led to a decrease in the in vitro NMDA receptor antagonist potency; the ortho position was optimal for this methyl or methoxy group (Table 5). Also illustrated in Table 5 are those compounds possessing the 3,3-bis(3-fluorophenyl) moiety with additional methyl or methoxy substitutions on the phenyl rings, often leading to an increase in NMDA receptor antagonist potency. Table 6 also illustrates those compounds possessing the 3,3-bis(2-methylphenyl) or 3,3-bis(2-methoxyphenyl) moiety in place of the 3,3-bis(3-fluorophenyl) moiety; these substitutions are acceptable, although a loss of potency is noted.

TABLE 5

| Compound | Structure | IC$_{50}$ ($\mu$M) vs. NMDA[a] |
|---|---|---|
| 3,3-bis(3-fluorophenyl)-1-propylamine (Compound 20) | 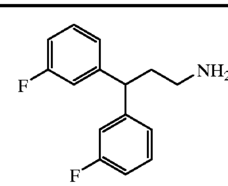 | 0.057 |

TABLE 5-continued

| Compound | Structure | IC$_{50}$ ($\mu$M) vs. NMDA[a] |
|---|---|---|
| 3-(3-fluorophenyl)-3-(2-methylphenyl)-1-propylamine (Compound 27) | 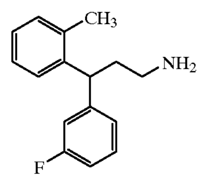 | 0.071 |
| 3-(3-fluorophenyl)-3-(3-methylphenyl)-1-propylamine (Compound 28) | 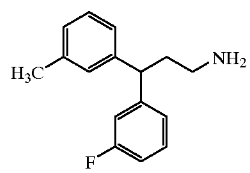 | 0.380 |
| 3-(3-fluorophenyl)-3-(4-methylphenyl-1-propylamine (Compound 29) | 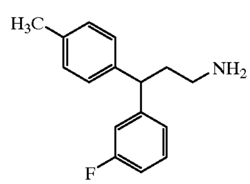 | 1.9 |
| 3-(3-fluorophenyl)-3-(2-methoxyphenyl)-1-propylamine (Compound 24) | 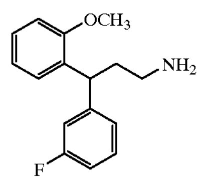 | 0.222 |
| 3-(3-fluorophenyl)-3-(3-methoxyphenyl)-1-propylamine (Compound 25) | 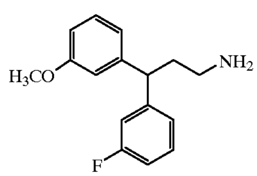 | 0.279 |
| 3-(3-fluorophenyl)-3-(4-methoxyphenyl)-1-propylamine (Compound 26) | 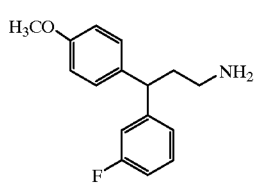 | 27 |
| 3-(3-fluorophenyl)-3-(2-methyl-3-fluorophenyl)-1-propylamine Compound 56 | 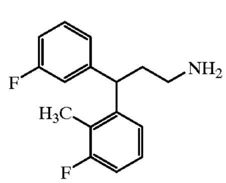 | 0.218 |
| 3-(3-fluorophenyl)-3-(3-fluoro-6-methylphenyl)-1-propylamine Compound 57 | 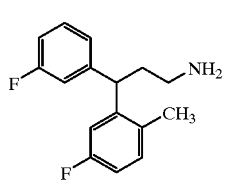 | 0.028 |
| 3,3-bis(3-fluoro-6-methylphenyl)-1-propylamine Compound 58 | | 0.028 |
| 3-(3-fluorophenyl)-3-(3-fluoro-6-methoxyphenyl)-1-propylamine Compound 61 | | 0.134 |
| 3,3-bis(2-methoxyphenyl)-1-propylamine Compound 62 | | 0.177 |
| 3,3-bis(2-methylphenyl)-1-propylamine Compound 65 | | 0.167 |

[a]Inhibition of NMDA/glycine-induced increases in intracellular calcium in cultured rat cerebellar granule cells (RCGC's) (see Example 1).

The next series of SAR experiments investigated the effect of alkyl chain substitutions (branching patterns) on NMDA receptor antagonist potency in vitro. The addition of a methyl group on either the α or β carbon on the propyl side chain led to a decrease or an increase in potency, respectively (Table 6).

TABLE 6

| Compound | Structure | IC$_{50}$ ($\mu$M) vs. NMDA[a] |
|---|---|---|
| 3,3-bis(3-fluorophenyl)-1-propylamine (Compound 20) | 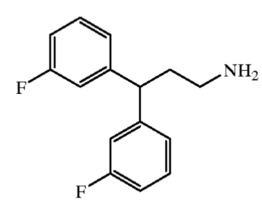 | 0.057 |
| 3,3-bis(3-fluorophenyl)-2-methyl-1-propylamine (Compound 21) | 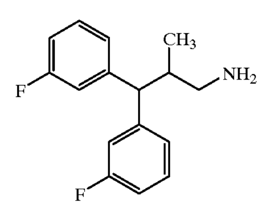 | 0.029<br>0.037[b]<br>0.430[b] |

TABLE 6-continued

| Compound | Structure | IC$_{50}$ ($\mu$M) vs. NMDA[a] |
|---|---|---|
| 3,3-bis(3-fluorophenyl)-2-methyl-1-propylamine (Compound 33) | 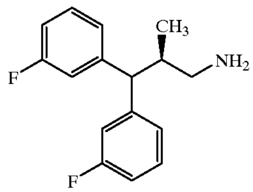 | not tested |
| 3,3-bis(3-fluorophenyl)-2-methyl-1-propylamine (Compound 34) | 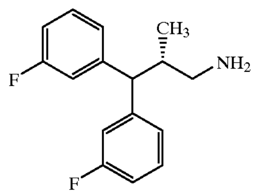 | not tested |
| 3,3-bis(3-fluorophenyl)-1-methyl-1-propylamine (Compound 22) | 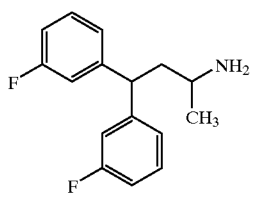 | 0.145 |
| 3,3-bis(3-fluorophenyl)-1-methyl-1-propylamine (Compound 50) | 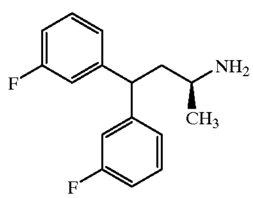 | 0.089 |
| 3,3-bis(3-fluorophenyl)-1-methyl-1-propylamine (Compound 51) | 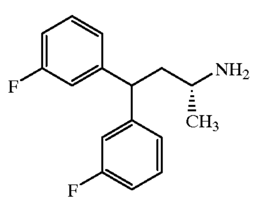 | 1.1 |
| 3,3-bis(3-fluorophenyl)-1-ethyl-1-propylamine (Compound 23) | 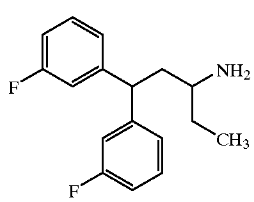 | 0.267 |
| 3,3-bis(3-fluorophenyl)-2,2-dimethyl-1-propylamine (Compound 41) | 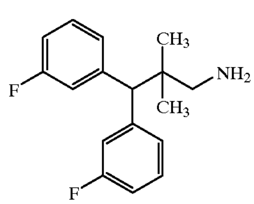 | 0.724 |
| 3,3-bis(3-fluorophenyl)-1,2-dimethyl-1-propylamine (Compound 38) | 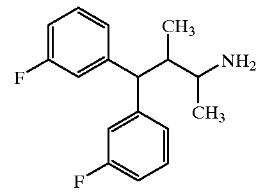 | 0.468 |

[a]Inhibition of NMDA/glycine-induced increases in intracellular calcium in cultured rat cerebellar granule cells (RCGC's) (see Example 1).
[b]Enantiomers of Compound 21 (Compounds 33 and 34) whose absolute stereochemistry has not been assigned at this time.

Certain simplified arylalkylamine compounds were selected for evaluation of activity in a battery of neurotransmitter receptor binding assays, and for activity against the L-type calcium channel and delayed rectifier potassium channel. The compounds were inactive (less than 50% inhibition at concentrations up to 10 $\mu$M) in the following assays: nonselective $\alpha$2 adrenergic receptor ([$^3$H]RX 821002 binding in rat cortex), H1 histamine receptor ([$^3$H] pyrilamine binding in bovine cerebellum), nonselective sigma receptor ([$^3$H]DTG binding in guinea pig brain), nonselective opiate receptor ([$^3$H]naloxone binding in rat forebrain), monoamine oxidase (MAO) activity, both MAO-A ([$^{14}$C]serotonin metabolism in rat liver mitochondria) and MAO-B ([$^{14}$C]phenylethylamine metabolism in rat liver mitochondria).

As can be seen in Table 7, activity was noted for several compounds at concentrations below 10 $\mu$M in the following assays: L-type calcium channel, delayed rectifier potassium channel, central muscarinic cholinergic receptor binding, and monoamine (dopamine, norepinephrine, and serotonin) uptake binding assays. This profile of activity in the central muscarinic cholinergic receptor and monoamine uptake binding assays is not unexpected, given the chemical structures of our simplified arylalkylamines (refer to Table 2 above). With the exceptions, however, of the activity of Compound 19 in the serotonin uptake binding assay, the activity of enantiomer #2 of Compound 20 in the dopamine uptake binding assay, the activity of Compound 50 in the serotonin uptake binding assay, and the activity of Compounds 63 and 64 in the dopamine uptake binding assay, the simplified arylalkylamine compounds were most potent at the NMDA receptor.

TABLE 7

| Compound | IC$_{50}$ ($\mu$M) vs. NMDA[a] | L-type calcium channel[b] | Delayed rectifier potassium channel[c] | Central muscarinic cholinergic receptor[d] | Monoamine uptake binding assays[e] |
|---|---|---|---|---|---|
| 19 | 0.435 | 10.2 | 1–10 | 4% at 0.1<br>74% at 10 | 7% at 0.1[f]<br>75% at 10[f]<br>3% at 0.1[g]<br>53% at 10[g]<br>18% at 0.1[h]<br>89% at 10[h] |
| 20 | 0.057 | 3.2 | 1–10 | 8% at 0.1<br>90% at 10 | 6% at 0.1[f]<br>81% at 10[f]<br>5% at 0.1[g]<br>58% at 10[g]<br>28% at 0.1[h]<br>94% at 10[h] |
| enantiomer #1 of 21[i] | 0.037 | not tested | >10 | 42% at 0.1<br>99% at 10 | 23% at 0.1[f]<br>86% at 10[f]<br>2% at 0.1[g]<br>54% at 10[g]<br>14% at 0.1[h]<br>89% at 10[h] |
| enantiomer #2 of 21[i] | 0.430 | not tested | ~10 | 25% at 0.1<br>99% at 10 | 60% at 0.1[f]<br>99% at 10[f]<br>10% at 0.1[g]<br>64% at 10[g]<br>12% at 0.1[h]<br>79% at 10[h] |
| 50 | 0.089 | not tested | ~10 | 11% at 0.1<br>84% at 10 | 17% at 0.1[f]<br>93% at 10[f]<br>10% at 0.1[g]<br>78% at 10[g]<br>75% at 0.1[h]<br>97% at 10[h] |
| 46 | 0.013 | 0.676 | ~3 | 33% at 0.1<br>89% at 10 | 40% at 0.1[f]<br>97% at 10[f]<br>7% at 0.1[g]<br>64% at 10[g]<br>10% at 0.1[h]<br>75% at 10[h] |
| 63 | 0.093 | 1.9 | not tested | 11% at 0.1<br>81% at 10 | 64% at 0.1[f]<br>98% at 10[f]<br>7% at 0.1[g]<br>76% at 10[g]<br>13% at 0.1[h]<br>85% at 10[h] |
| 64 | 0.309 | not tested | not tested | 11% at 0.1<br>83% at 10 | 50% at 0.1[f]<br>99% at 10[f]<br>8% at 0.1[g]<br>65% at 10[g]<br>29% at 0.1[h]<br>68% at 10[h] |
| 58 | 0.028 | 1.6 | not tested | 1% at 0.1<br>48% at 10 | 0% at 0.1[f]<br>45% at 10[f]<br>1% at 0.1[g]<br>67% at 10[g]<br>27% at 0.1[h]<br>95% at 10[h] |

TABLE 7-continued

| Compound | IC$_{50}$ ($\mu$M) vs. NMDA[a] | L-type calcium channel[b] | Delayed rectifier potassium channel[c] | Central muscarinic cholinergic receptor[d] | Monoamine uptake binding assays[e] |
|---|---|---|---|---|---|
| 59 | 0.272 | not tested | not tested | 9% at 0.1<br>87% at 10 | 2% at 0.1[f]<br>78% at 10[f]<br>7% at 0.1[g]<br>51% at 10[g]<br>14% at 0.1[h]<br>86% at 10[h] |

[a]Inhibition of NMDA/glycine-induced increases in intracellular calcium in cultured rat cerebellar granule cells (RCGC's) (see Example 1).
[b]Inhibition of KCl depolarization-induced increases in intracellular calcium in cultured rat cerebellar granule cells (RCGCs); estimated IC$_{50}$ value in $\mu$M.
[c]Inhibition of delayed rectifier potassium channel in cultured N1E-115 neuroblastoma cells; estimated IC$_{50}$ value in $\mu$M.
[d]Inhibition of the binding of [$^3$H]quinuclidinylbenzilate (QNB) to rat cortical membranes; percent block at indicated concentration in $\mu$M.
[e]Inhibition of the binding of [$^3$H]WIN-35,428 to guinea pig striatal membranes (dopamine uptake binding assay), [$^3$H]desipramine to rat cortical membranes (norepinephrine uptake binding assay), or [$^3$H]citalopram to rat forebrain membranes (serotonin uptake binding assay); percent block at indicated concentration in $\mu$M.
[f]dopamine uptake binding assay
[g]norepinephrine uptake binding assay
[h]serotonin uptake binding assay
[i]enantiomers of Compound 21 (Compounds 33 and 34) whose absolute stereochemistry has not been assigned at this time Advantageous properties of the arylalkylamine compounds of the present invention are illustrated by the fact that concentrations which suppress NMDA receptor-mediated synaptic transmission fail to inhibit LTP. Furthermore, while compounds such as Compound 9, and 11 do produce a hypotensive response following systemic administration in rats, the hypotensive effect produced by these compounds is of a relatively short duration (approximately 30 min). Additionally, Compounds 12 and 14 have no cardiovascular activity at doses up to 37.3 $\mu$moles/kg i.v. and 15 $\mu$moles/kg i.v., respectively.

TABLE 8

| Compound | Suppression of NMDA Receptor-Mediated Synaptic Transmission[a] | LTP Assay[b] | Drop in Mean Arterial Blood Pressure[c] |
|---|---|---|---|
| Compound 1 | 10–30 $\mu$M | no block at 300 $\mu$M | 65 mm Hg at 1.5 $\mu$moles/kg i.v., 60 min duration |
| Compound 2 | 10–30 $\mu$M | no block at 100 $\mu$M | 40 mm Hg at 1.5 $\mu$moles/kg i.v., 120 min duration |
| Compound 3 | 10–30 $\mu$M | not tested | 20 mm Hg at 1 mg/kg s.c., >60 min duration |
| Compound 4 | 10–100 $\mu$M | no block at 100 $\mu$M | 40 mm Hg at 1.5 $\mu$moles/kg i.v., 120 min duration |
| Compound 9 | 10–100 $\mu$M | no block at 300 $\mu$M | 75 mm Hg at 4.5 $\mu$moles/kg i.v., 90 min duration |
| Compound 11 | not tested | not tested | 20 mm Hg at 1 mg/kg i.v., 30 min duration |
| Compound 12 | not tested | not tested | no effect at doses up to 37.3 $\mu$moles/kg i.v. |
| Compound 14 | not tested | not tested | no effect at doses up to 15 $\mu$moles/kg i.v. |
| Compound 19 | 100–300 $\mu$M | block at 100 $\mu$M | not tested |
| Compound 20 | 30–300 $\mu$M | block at 100 $\mu$M | no effect at doses up to 15 $\mu$moles/kg i.v. |
| Compound 22 | not tested | not tested | no effect at doses up to 15 $\mu$moles/kg i.v. |

[a]: Concentration which suppresses NMDA receptor-mediated synaptic transmission (see Example 5).
[b]: Concentration that does not block the induction of LTP (see Example 19).
[c]: Drop in systemic blood pressure produced by administration of compound in rats (see Example 22).

Formulation and Administration

As demonstrated herein, useful compounds of this invention and their pharmaceutically acceptable salts may be used to treat neurological disorders or diseases. While these compounds will typically be used in therapy for human patients, they may also be used to treat similar or identical diseases in other vertebrates such as other primates, farm animals such as swine, cattle and poultry, and sports animals and pets such as horses, dogs and cats.

In therapeutic and/or diagnostic applications, the compounds of the invention can be formulated for a variety of modes of administration, including systemic, topical, or localized administration. Techniques and formulations generally may be found in *Remington's Pharmaceutical Sciences,* Mack Publishing Co., Easton, Pa.

Pharmaceutically acceptable salts are generally well known to those of ordinary skill in the art, and may include, by way of example but not limitation, acetate, benzenesulfonate, besylate, benzoate, bicarbonate, bitartrate, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, mucate, napsylate, nitrate, pamoate (embonate), pantothenate, phosphate/disphosphate, polygalacturonate, salicylate, stearate, subacetate, succinate, sulfate, tannate, tartrate, or teoclate. Other pharmaceutically acceptable salts may be found in, for example, *Remington's Pharmaceutical Sciences,* Mack Publishing Co., Easton, Pa. (18th ed., 1990).

Preferred pharmaceutically acceptable salts include, for example, acetate, benzoate, carbonate, citrate, gluconate, hydrobromide, hydrochloride, maleate, mesylate, napsylate, pamoate (embonate), phosphate, salicylate, succinate, sulfate, or tartrate.

The useful compounds of this invention may also be in the form of pharmaceutically acceptable complexes. Pharmaceutically acceptable complexes are known to those of ordinary skill in the art and include, by way of example but not limitation, 8-chlorotheophyllinate (teoclate).

The exact formulation, route of administration and dosage can be chosen by the individual physician in view of the patient's condition. (See e.g., Fingl et al., in *The Pharmacological Basis of Therapeutics,* 1975, Ch. 1, p. 1).

It should be noted that the attending physician would know how and when to terminate, interrupt, or adjust administration due to toxicity or organ dysfunction. Conversely, the attending physician would also know Lo adjust treatment to higher levels if the clinical responses were not adequate (precluding toxicity). The magnitude of an administered dose in the management of the disorder of interest will vary with the severity of the condition to be treated and to the route of administration. The severity of the condition may, for example, be evaluated in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated into liquid or solid dosage forms and administered systemically or locally. Techniques for formulation and administration may be found in *Remington's Pharmaceutical Sciences,* Mack Publishing Co., Easton, Pa. Suitable routes may include oral, buccal, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. The compounds can be formulated readily using pharmaceutically acceptable carriers well known in the art into dosage forms suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily suspensions for injection. Suitable lipophilic solvents or vehicles include fatty oils such as sesame oil, or synthetic fatty acid esters, such as ethyl oleate or triglycerides, or liposomes. Aqueous suspensions for injection may contain substances which increase the viscosity of the suspension, such as sodium carboxymethylcellulose (CMC), sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropyl methylcellulose, sodium carboxymethylcellulose (CMC), and/or polyvinylpyrrolidone (PVP:povidone). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin, and a plasticizer, such as glycerol or sorbitol. The push-fit capsules can contain the active ingredients in admixture with a filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Other embodiments are within the following claims.

We claim:

1. A compound selected from the group consisting of

Compound 63

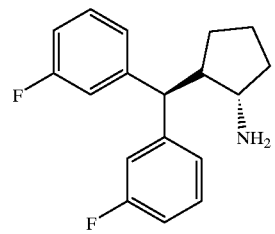

and

Compound 64

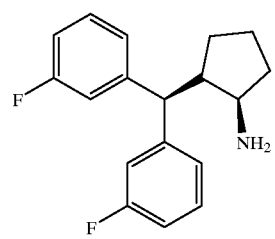

and pharmaceutically acceptable salts and complexes thereof.

2. A compound having the chemical structure

Compound 63

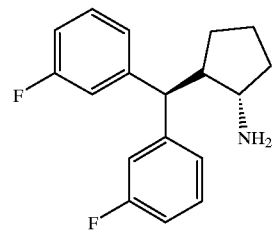

or a pharmaceutically acceptable salt or complex thereof.

3. A compound having the chemical structure

Compound 64

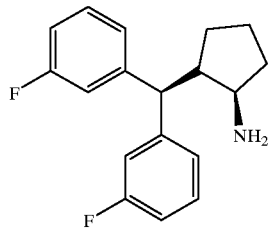

or a pharmaceutically acceptable salt or complex thereof.

4. A pharmaceutical composition comprising a compound which is selected from the group consisting of Compound 63

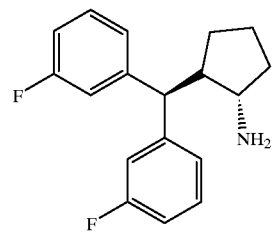

and

Compound 64

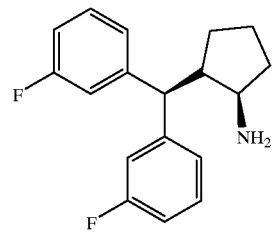

and pharmaceutically acceptable salts and complexes thereof, in a pharmaceutically acceptable carrier.

5. A pharmaceutical composition comprising a compound having the chemical structure Compound 63

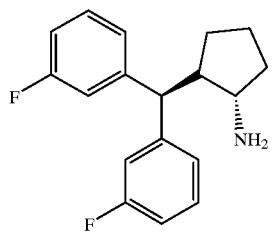

or a pharmaceutically acceptable salt or complex thereof, in a pharmaceutically acceptable carrier.

6. A pharmaceutical composition comprising a compound having the chemical structure

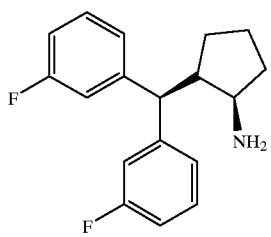

Compound 64 or a pharmaceutically acceptable salt or complex thereof, in a pharmaceutically acceptable carrier.

7. The pharmaceutical composition of claim 5 or 6, adapted for the treatment of a neurological disease or disorder.

8. The pharmaceutical composition of claim 7, wherein said neurological disease or disorder is selected from the group consisting of stroke, head trauma, spinal cord injury, epilepsy, anxiety, Alzheimer's disease, Huntington's disease, Parkinson's disease, or amyotrophic lateral sclerosis.

9. The pharmaceutical composition of claim 5 or 6, wherein said pharmaceutical composition has neuroprotectant activity.

10. The pharmaceutical composition of claim 8, wherein said stroke is global ischemic.

11. The pharmaceutical composition of claim 8, wherein said stroke is hemorrhagic.

12. The pharmaceutical composition of claim 8 wherein said stroke is focal ischemic.

13. The phannaceutical composition of claim 8 wherein said neurological disease or disorder is Parkinson's disease.

14. A method for treating a patient having a neurological disease or disorder, comprising administering a compound which is selected from the group consisting of

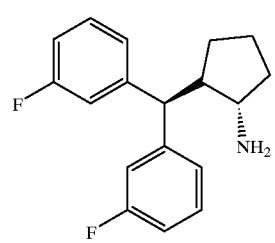

Compound 63 and

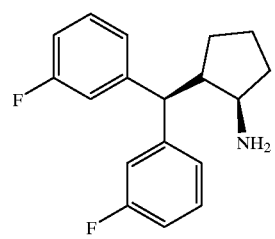

Compound 64 and pharmaceutically acceptable salts and complexes thereof.

15. The method of claim 14, wherein said compound is

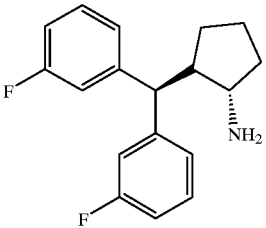

Compound 63 or a pharmaceutically acceptable salt or complex thereof.

16. The method of claim 14, wherein said compound is

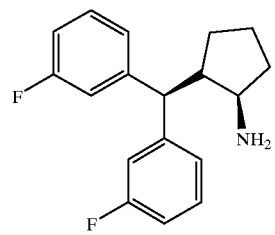

Compound 64 or a pharmaceutically acceptable salt or complex thereof.

17. The method of claim 15 or 16, wherein the neurological disease or disorder comprises stroke, head trauma, spinal cord injury, epilepsy, anxiety, Alzheimer's disease, Huntington's disease, Parkinson's disease, or amyotrophic lateral sclerosis.

18. The method of claim 17 wherein said stroke is global ischemic.

19. The method of claim 17 wherein said stroke is hemorrhagic.

20. The method of claim 17 wherein said stroke is focal ischemic.

21. The method of claim 17 wherein the neurological disease or disorder comprises Parkinson's disease.

22. A method for providing neuroprotection to a patient, comprising administering a compound which is selected from the group consisting of

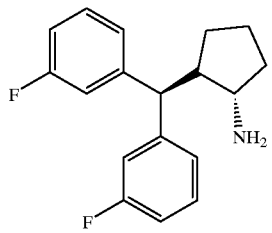

Compound 63 and

-continued
Compound 64
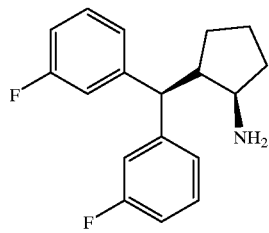
and pharmaceutically acceptable salts and complexes thereof.
23. The method of claim 22 wherein said compound is
Compound 63
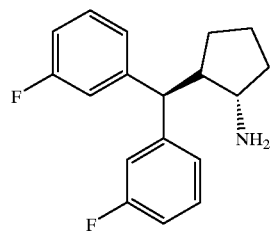
or a pharmaceutically acceptable salt or complex thereof.
24. The method of claim 22 wherein said compound is
Compound 64
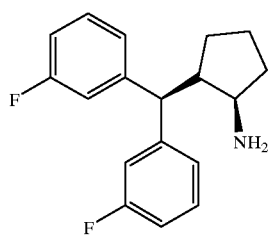
or a pharmaceutically acceptable salt or complex thereof.
* * * * *